United States Patent
Güven et al.

(10) Patent No.: US 10,934,253 B2
(45) Date of Patent: Mar. 2, 2021

(54) THERAPEUTIC COMPOUNDS AND METHODS

(71) Applicant: UNIVERSITY OF TASMANIA, Sandy Bay (AU)

(72) Inventors: Nuri Güven, Fern Tree (AU); Jason Smith, Kingston (AU); Krystel Lee Woolley, Huonville (AU); Monila Nadikudi, Newstead (AU)

(73) Assignee: University of Tasmania, Tasmania (AU)

( * ) Notice: Subject to any disclaimer, the term of this patent is extended or adjusted under 35 U.S.C. 154(b) by 0 days.

(21) Appl. No.: 16/606,842

(22) PCT Filed: Apr. 20, 2018

(86) PCT No.: PCT/AU2018/050360
§ 371 (c)(1),
(2) Date: Oct. 21, 2019

(87) PCT Pub. No.: WO2018/191789
PCT Pub. Date: Oct. 25, 2018

(65) Prior Publication Data
US 2020/0131119 A1    Apr. 30, 2020

(30) Foreign Application Priority Data
Apr. 21, 2017 (AU) .................... 2017901457

(51) Int. Cl.
*C07C 233/51* (2006.01)
*A61P 25/00* (2006.01)

(52) U.S. Cl.
CPC ............ *C07C 233/51* (2013.01); *A61P 25/00* (2018.01); *C07C 2602/10* (2017.05)

(58) Field of Classification Search
CPC ...... C07C 233/51; C07C 2602/10; A61P 25/00
USPC ....................................... 564/123
See application file for complete search history.

(56) References Cited

U.S. PATENT DOCUMENTS

| 4,388,312 | A | 6/1983 | Terao et al. |
| 9,040,713 | B2 | 5/2015 | Ye |
| 2005/0049313 | A1 | 3/2005 | Nishizawa et al. |
| 2006/0058398 | A1 | 3/2006 | Kamei et al. |
| 2008/0200441 | A1 | 8/2008 | Brinton et al. |
| 2009/0118257 | A1 | 5/2009 | Jankowski et al. |
| 2014/0094464 | A1 | 4/2014 | Kelley et al. |

FOREIGN PATENT DOCUMENTS

| EP | 0915696 | A2 | 5/1999 |
| EP | 2620141 | A1 | 7/2013 |
| EP | 2939668 | A1 | 11/2015 |
| GB | 2321455 | A | 7/1998 |
| WO | 1995000157 | A1 | 1/1995 |
| WO | 2000008495 | A2 | 2/2000 |
| WO | 2002076939 | A2 | 10/2002 |
| WO | 2004085421 | A2 | 10/2004 |
| WO | 2006020959 | A2 | 2/2006 |
| WO | 2009118327 | A1 | 10/2009 |
| WO | 2011077158 | A1 | 6/2011 |
| WO | 2011092284 | A1 | 8/2011 |
| WO | 2011098545 | A1 | 8/2011 |
| WO | 2012019029 | A2 | 2/2012 |
| WO | WO-2012019029 | A2 * | 2/2012 | ............. A61P 25/08 |
| WO | 2012064396 | A2 | 5/2012 |
| WO | 2012167122 | A1 | 12/2012 |
| WO | 2013033515 | A1 | 3/2013 |
| WO | 2014063061 | A1 | 4/2014 |
| WO | 2014194292 | A1 | 12/2014 |
| WO | 2015116867 | A1 | 8/2015 |
| WO | 2018194976 | A1 | 10/2018 |
| WO | 2019157163 | A1 | 8/2019 |

OTHER PUBLICATIONS

Biot, Christophe et al., "5-substituted tetrazoles as bioisosteres of carboxylic acids. Bioisosterism and mechanistic studies on glutathione reductase inhibitors as antimalarials," Journal of medicinal chemistry, 2004, 47(24), pp. 5972-5983.
Dhaon, Madhup K. et al., "Derivatives of 2-methyl-1,4-naphthoquinone as substrates and inhibitors of the vitamin kdependent carboxylase," Journal of Medicinal Chemistry, 1984, 27(9), pp. 1196-1201.
Feng, Zikai et al., "Metabolic Stability of New Mito-Protective Short-Chain Naphthoquinones," Pharmaceuticals, 2020, vol. 13, No. 29, pp. 1-12.
Fieser, L. F. et al., "Naphthoquinone acids and ketols," Journal of the American Chemical Society, 1947, 69(10), pp. 2338-2341.
Gupta, M.K., "CP-MLR/PLS-directed QSAR studies on the antimalarial activity and cytotoxicity of substituted 4-aminoquinolines," Medicinal Chemistry Research, 2013, 22(7), pp. 3497-3509.
Johann, Laure et al. "Synthesis and evaluation of 1,4-naphthoquinone ether derivatives as SmTGR inhibitors and new istosomal drugs." The FEBS journal, 2015, 282 (16), pp. 3199-3217.

(Continued)

*Primary Examiner* — Yong L Chu
(74) *Attorney, Agent, or Firm* — Honigman LLP; Fernando Alberdi; Jonathan P. O'Brien

(57) ABSTRACT

The invention relates to compounds of Formula (I) and methods for their preparation. Also described are pharmaceutical compositions comprising a compound of Formula (I) and their use in the treatment or prevention of conditions associated with mitochondrial dysfunction. Formula (I)

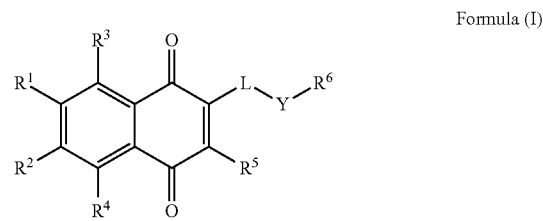

Formula (I)

11 Claims, 11 Drawing Sheets

(56) References Cited

OTHER PUBLICATIONS

Kazemêkaitê, Maryte et al., "2-Methyl-1, 4-naphthoquinones containing 3-[N-(?-mercaptoalkyl) alkanamide] chains: synthesis, self-assembling, and electrochemical properties," Tetrahedron Letters, 2008, 49(43), pp. 6212-6216.
Mecklenburg, Susanne et al., "Exploring synthetic avenues for the effective synthesis of selenium-and tellurium-containing multifunctional redox agents." Organic & Biomolecular chemistry, 2009, 7(22), pp. 4753-4762.
PCT/AU2018/050360 International Search Report dated Jun. 8, 2018, 6 pgs.
Salmon-Chemin, Laurence. et al., "Parallel synthesis of a library of 1, 4-naphthoquinones and automated screening of potential inhibitors of trypanothione reductase from Trypanosoma cruzi," Bioorganic & medicinal chemistry letters, 2000, 10(7), pp. 631-635.
Salmon-Chemin, Laurence et al., "2-and 3-substituted 1, 4-naphthoquinone derivatives as subversive substrates of trypanothione reductase and lipoamide dehydrogenase from trypanosoma cruzi: synthesis and correlation between redox cycling activities and in vitro cytotoxicity." Journal of medicinal chemistry, 2001, 44(4), pp. 548-565.
Thi, Tuyet Anh Dang et al., "Synthesis and anticancer properties of new (dihydro) pyranonaphthoquinones and their epoxy analogs," Bioorganic & Medicinal Chemistry Letters, 2015, 25(16), pp. 3355-3358.
Weerapreeyakul, N. et al., "Reductive and bioreductive activation is controlled by electronic properties of substituents in conformationally-constrained anticancer drug delivery systems," Medicinal Chemistry Research, 2000, 10(3), pp. 149-163.
Woolley, Krystel L. et al., "Amide linked redox-active naphthoquinones for the treatment of mitochondrial dysfunction," Med.Chem. Comm., 2019, vol. 10, pp. 399-412.

* cited by examiner

THERAPEUTIC COMPOUNDS AND METHODS

CROSS-REFERENCE TO RELATED APPLICATIONS

This application is a 35 U.S.C. § 371(c) United States National Phase Application of, and claims priority to International Patent Application No. PCT/AU2018/050360, filed Apr. 20, 2018, which claims priority to Australian Application No. 2017901457, filed Apr. 21, 2017. The entire contents of the aforementioned disclosures are incorporated herein by reference in their entireties.

FIELD

The present invention relates generally to compounds useful in the modulation of mitochondrial activity. The present invention also relates to the use of these compounds in the treatment of diseases and disorders associated with mitochondrial dysfunction.

DESCRIPTION OF RELATED ART

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

Mitochondria are cytoplasmic organelles which carry out a variety of cellular metabolic functions. The primary function of the mitochondria is to produce energy in the form of adenosine triphosphate (ATP) via oxidative phosphorylation. ATP functions as energy "currency" or an energy carrier in a cell, and eukaryotic cells derive the majority of their ATP from biochemical processes carried out by mitochondria. Mitochondria also play a primary role in signalling, cellular differentiation, and regulation of cell death. The biochemical processes carried out by mitochondria include the citric acid cycle (also referred to as the Krebs cycle), which generates reduced nicotinamide adenine dinucleotide (NADH+H+) from oxidized nicotinamide adenine dinucleotide (NAD+), and oxidative phosphorylation, during which NADH+H+ is oxidized back to NAD+. Increasingly, it is recognized that mitochondria have been implicated in a range of both diseases and disorders.

Mitochondrial dysfunction, that is, a reduction in or impairment of typical mitochondrial function, may result from genetic or environmental factors or combinations thereof. Mitochondrial dysfunction is considered to contribute to various disease states and is a hallmark of a number of inherited disorders. It is estimated that up to 1 in 100 newborns will be affected by a mitochondrial disease during their lifetime. In addition, it is considered that mitochondrial dysfunction may form part of the underlying pathophysiology in many common diseases and health conditions, including but not limited to neurodegenerative disorders, diabetes, cancer, blindness, deafness, heart disease, liver disease, kidney disease, gastrointestinal disorders, stoke, seizure, Alzheimer's diseases, Parkinson's disease, autism, bipolar, schizophrenia, depression, asthma, chronic fatigue, myoclonic epilepsy with ragged red fibers (MERRF); mitochondrial myopathy, encephalopathy, lactacidosis; leber's hereditary optic neuropathy (LHON); dominant optic atrophy (DOA); Leigh syndrome; Kearns-Sayre syndrome (KSS); Friedreich's ataxia (FRDA); cardiomyopathy; encephalomyopathy; renal tubular acidosis; amyotrophic lateral sclerosis (ALS); Huntington's Disease, and developmental pervasive disorders.

Identifying therapies that can restore or enhance mitochondrial function has the potential for a wide range of applications. To date, therapeutic approaches for the above indications have typically been directed to the alleviation of symptoms and/or the treatment of secondary or associated conditions rather than addressing underlying mitochondrial dysfunction. A benzoquinone, idebenone, was approved by the European Medicines Agency in 2015 for the treatment of a form of mitochondrial dysfunction-induced vision loss in young men (Leber's hereditary optic neuropathy, LHON). However, idebenone exhibits very poor bioavailability and undergoes excessive first pass metabolism in the liver upon administered.

There is a need for improved and specific therapies for the treatment of diseases and disorders associated with mitochondrial dysfunction.

SUMMARY

The present invention provides compounds of Formula (I) and pharmaceutical compositions thereof. In an embodiment the compounds of Formula (I) have utility in the modulation of mitochondrial activity. In another embodiment, the compounds of Formula (I) have utility in enhancing mitochondrial function. In still another embodiment, the compounds of Formula (I) have utility in restoring mitochondrial function. In still another embodiment, the compounds of Formula (I) have utility in protecting against mitochondrial dysfunction.

It is proposed that the compounds of Formula (I) and pharmaceutical compositions thereof enabled herein are useful in the prophylaxis and/or treatment of diseases and disorders associated with mitochondrial dysfunction.

In one or more aspects, there is provided compounds Formula (I):

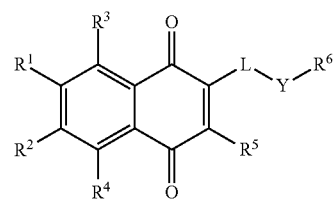

Formula (I)

or a pharmaceutically acceptable salt thereof, wherein $R^1$, $R^2$, $R^3$ and $R^4$ are each independently selected from H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, halogen, optionally substituted $C_1$-$C_6$ alkylhalo; optionally substituted $C_1$-$C_6$ thioalkyl, —SR, —NRR', optionally substituted $C_3$-$C_7$ cycloalkyl, optionally substituted $C_2$-$C_{12}$ heterocyclyl, optionally substituted $C_5$-$C_2$ aryl, and optionally substituted $C_2$-$C_{12}$ heteroaryl, $R^5$ is selected from H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, halogen, optionally substituted $C_1$-$C_6$ alkylhalo; optionally substituted $C_1$-$C_6$ thioalkyl, —SR, —NRR', optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl, L is a divalent linker selected from a bond, optionally substituted $C_1$-$C_{20}$ alkylene, optionally substituted $C_1$-$C_{20}$ alkenylene, optionally substituted $C_1$-$C_{20}$ alkynylene;

Y is absent or is a divalent linker selected from optionally substituted $C_3$-$C_6$ cycloalkylene, optionally substituted $C_2$-$C_{12}$ heterocyclyl, optionally substituted $C_5$-$C_2$ arylene, optionally substituted $C_2$-$C_{12}$ heteroarylene, —C(O)—NR—, —C(O)—NR—(CH$_2$)$_y$—, —C(O)—O—, —C(O)—OR—, —C(O)—O—(CH$_2$)$_y$—, —C(O)—, —C(CX$_3$)—NR—, —CRR'X—NR—, —NR—C(O)—NR'—, —O—C(O)O—, —C=N—O—, —SO$_2$—NR—, —(CH$_2$)$_x$—NR—, —(CH$_2$)$_y$—S—(CH$_2$)$_z$—, —(CH$_2$)$_y$—O—(CH$_2$)$_z$—, wherein y and z are each integers independently selected from 0, 1, 2, 3 and 4;

$R^6$ is selected from H, —COOR, —OR, —NRR', —SR, optionally substituted $C_1$-$C_{20}$ alkyl, optionally substituted $C_2$-$C_{20}$ alkenyl, optionally substituted $C_2$-$C_{20}$ alkynyl; optionally substituted $C_3$-$C_7$ cycloalkyl, optionally substituted $C_5$-$C_{12}$ aryl, optionally substituted $C_2$-$C_{12}$ heteroaryl or optionally substituted $C_2$-$C_{12}$ heterocyclyl, optionally substituted $C_1$-$C_6$ alkanolamino, optionally substituted amino acid, optionally substituted dipeptide, optionally substituted tripeptide, and optionally substituted polypeptide, or Y and $R^6$ taken together form a group selected from

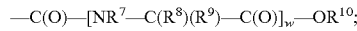

—C(O)—[NR$^7$—C(R$^8$)(R$^9$)—C(O)]$_w$—OR$^{10}$;

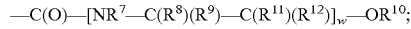

—C(O)—[NR$^7$—C(R$^8$)(R$^9$)—C(R$^{11}$)(R$^{12}$)]$_w$—OR$^{10}$;

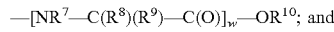

—[NR$^7$—C(R$^8$)(R$^9$)—C(O)]$_w$—OR$^{10}$; and

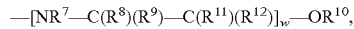

—[NR$^7$—C(R$^8$)(R$^9$)—C(R$^{11}$)(R$^{12}$)]$_w$—OR$^{10}$, wherein $R^7$, $R^8$, $R^{10}$, $R^{11}$ and $R^{12}$ at each occurrence are H or optionally substituted $C_1$-$C_6$-alkyl; $R^9$ at each occurrence is independently selected from H and an amino acid side chain or a derivative thereof; and w is an integer from 0 to 20, R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl, and X is a halogen.

In further aspects, there is provided compounds of Formula (Ia):

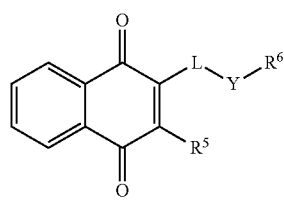

Formula (Ia)

or a pharmaceutically acceptable salt thereof, wherein:
$R^5$ is selected from H and optionally substituted $C_1$-$C_6$ alkyl,
L is an optionally substituted $C_1$-$C_{20}$ alkylene,
Y is a divalent linker selected from optionally substituted —C(O)—NR—, —C(O)—NR—(CH$_2$)$_y$—, —C(O)—O—, —C(O)—, —(CH$_2$)$_y$—S—(CH$_2$)$_z$—, —(CH$_2$)$_y$—O—(CH$_2$)$_z$—, wherein y and z are each integers independently selected from 0, 1, 2, 3 and 4;

$R^6$ is selected from H, —COOR; optionally substituted $C_5$-$C_{12}$ aryl, optionally substituted $C_2$-$C_{12}$ heteroaryl, optionally substituted $C_1$-$C_6$ alkanolamino, optionally substituted amino acid,
or Y and $R^6$ taken together form a group selected from

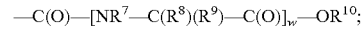

—C(O)—[NR$^7$—C(R$^8$)(R$^9$)—C(O)]$_w$—OR$^{10}$;

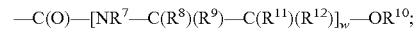

—C(O)—[NR$^7$—C(R$^8$)(R$^9$)—C(R$^{11}$)(R$^{12}$)]$_w$—OR$^{10}$;

wherein $R^7$, $R^8$, $R^{10}$, $R^{11}$ and $R^{12}$ at each occurrence are H or optionally substituted $C_1$-$C_6$-alkyl; $R^9$ at each occurrence is independently selected from H and an amino acid side chain or a derivative thereof; and w is an integer from 0 to 20;

R and R' are independently H, optionally substituted $C_1$-$C_6$ alkyl.

In another aspect, there is provided compounds of Formula (Ib):

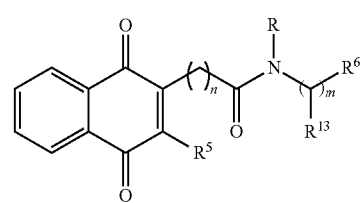

Formula (Ib)

or a pharmaceutically acceptable salt thereof, wherein:
$R^5$ is selected from H and methyl,
$R^6$ is selected from H, —COOR, —OH, optionally substituted $C_5$-$C_{12}$ aryl, optionally substituted $C_2$-$C_{12}$ heteroaryl,
R is H or optionally substituted $C_1$-$C_6$ alkyl;
$R^{13}$ at each occurrence is independently selected from H, optionally substituted phenyl, and optionally substituted benzyl,
n is an integer selected from 1, 2, 3, 4 and 5, and
m is an integer selected from 0, 1, 2, and 3.

Also taught herein are processes for the preparation of compounds of Formula (I), Formula (Ia) and Formula (Ib). These processes advantageously provide for the rapid assembly of compounds of Formula (I), Formula (Ia) and Formula (Ib) in relatively few chemical steps and/or in high purity.

Further contemplated herein is a method for the treatment of a mammalian subject comprising the administration of a compound of Formula (I) as defined herein or a pharmaceutically acceptable salt thereof. As noted above, it is considered that the compounds of Formula (I) and pharmaceutical compositions thereof enabled herein are useful in the prophylaxis and/or treatment of diseases and disorders associated with mitochondrial dysfunction.

In an embodiment, the diseases and disorders associated with mitochondrial dysfunction are primary mitochondrial diseases including but not limited to Leber's hereditary optic neuropathy (LHON), dominant optic neuropathy (DOA), Leigh syndrome, Friedreich's ataxia, mitochondrial myopathy, encephalomyopathy, lactic acidosis, stroke-like symptoms (MELAS), myoclonic epilepsy with ragged red fibers (MERRF), myoneurogenic gastrointestinal encephalomyopathy (MNGIE), Kearns-Sayre syndrome, CoQ.10 deficiency, or mitochondrial complex deficiencies, neuropathy, ataxia, retinitis pigmentosa, and ptosis (NARP).

In an embodiment, the diseases and disorders associated with mitochondrial dysfunction are neurodegenerative or neuromuscular diseases associated with mitochondrial dysfunction including but not limited to spinocerebellar ataxias, ataxia telangiectasia, ataxia oculomotor apraxia 1 and 2 (AOA1 and 2), epileptic seizures, amyotrophic lateral sclerosis (ALS), motor neuron disease (MND), Parkinson's disease, Alzheimer's disease, Huntington's disease, stroke/reperfusion injury, or dementia, Duchenne muscular dystrophy (DMD), Becker muscular dystrophy (BMD), Limb-Girdle muscular dystrophy (LGMD), X-linked dilated cardiomyopathy (XLDCM), pantothenate kinase-associated neurodegeneration (PKAN,), spinal muscular atrophy (SMA), multiple sclerosis and primary progressive multiple sclerosis (PP-MS), Kugelberg-Welander disease, and Werdnig-Hoffmann disease, diabetes mellitus and deafness (DAD).

In an embodiment, the diseases and disorders associated with mitochondrial dysfunction are metabolic disorders associated with mitochondrial dysfunction including but not limited to Wolfram syndrome, non-alcoholic liver disease (i.e. NAFLD, NASH, cirrhosis), ageing-related physical decline, obesity, overweight, diabetes mellitus, type II diabetes, diabetic retinopathy, and metabolic syndrome.

In an embodiment, the diseases and disorders associated with mitochondrial dysfunction are psychiatric disorder associated with mitochondrial dysfunction including but not limited to schizophrenia, major depressive disorder, bipolar disorder, epilepsy, post-traumatic stress disorder (PTSD), and circadian rhythm disorders.

In an embodiment, the diseases and disorders associated with mitochondrial dysfunction are inflammatory disorders associated with mitochondrial including but not limited to ulcerative colitis (UC), Crohn's disease (CD), arthritis, psoriasis or rheumatoid arthritis, migraine, dry eye syndrome, uveitis, allergic conjunctivitis, post-operative inflammation and acute kidney injury. The subject invention further has a role as a means to reduce the effects of gaining. Hence, there are both therapeutic and cosmetic aspects to targeting mitochondrial dysfunction.

In an embodiment, the disease and disorder is caused by drug-induced or environmental-induced mitochondrial dysfunction. For example, factors having a negative effect on mitochondrial activity or function include drug- or environment-induced mitochondrial dysfunction resulting from an antiviral; an anti-cancer agent; an antibiotic; a CNS drug; a hypertensiondrug; an anthracyclines; a non-steroidal anti-inflammatory drug (NSAID); an anestetic; a beta-blocker; an anti-arrhythmic; an anti-diabetic; an anti-inflammatory; or another agent.

Examples of antivirals having a negative effect on mitochondrial activity or function include abacavir, didanosine, emtricitabine, entecavir, emtricitabine, lamivudine, nevirapine, telbivudine, tenofovir, tipranavir, stavudine, zalcitabine, and zidovudine. Examples of anti-cancer agents having a negative effect on mitochondrial activity or function include arsenic trioxide, cetuximab, dacarbazine, denileukin, diftitox, flutamide, gemtuzumab, methotrexate, mitoxantrone, pentostatin, and tamoxifen. Examples of antibiotics having a negative effect on mitochondrial activity or function include antimycin A, isoniazid, chloramphenicol, ethambutol, gentamycin, ketoconazole, linezolid, streptozocin, streptomycin, tobramycin, tetracyclines, and trovafloxacin. Examples of CNS drugs having a negative effect on mitochondrial activity or function include amitriptyline, amphetamines, atomoxetin, chlorpromazine, cocaine, dantrolene, desipramine, divalproex, droperidol, felbamate, fluphenazine, imipramine, methamphetamine, naltrexone, nefazodone, pergolide, and valproic acid. Examples of hypertension drugs having a negative effect on mitochondrial activity or function include bosentan. Examples of anthracyclines having a negative effect on mitochondrial activity or function include daunorubicin, doxorubicin, epirubicin, and idarubicin. Examples of non-steroidal anti-inflammatory drugs (NSAIDs) having a negative effect on mitochondrial activity or function include aspirin, celecoxib, diclofenac, diflunisal, etodolac, fenoprofen, ibuprofen, indomethacin, ketoprofen, mefenamic acid, meloxicam, naproxen, nabumetone, oxaprozin, piroxicam, salsalate, sulindac, thioridazine, and tolmetin. Examples of anestetics having a negative effect on mitochondrial activity or function include bupivacaine and isoflurane. Examples of beta-blockers having a negative effect on mitochondrial activity or function include atenolol. Example of anti-arrhythmics having a negative effect on mitochondrial activity or function include amiodarone, disopyramide, dofetilide, and ibutilide. Examples of anti-diabetics having a negative effect on mitochondrial activity or function include pioglitazone and rosiglitazone. Examples of anti-inflammatory agents having a negative effect on mitochondrial activity or function include prednisolone, dexamethasone, hydrocortisone, and triamcilone. Examples of other agents having a negative effect on mitochondrial activity or function include clioquinol, cyanide, hexachlorophene, rotenone, and statins.

In an embodiment, the mammal is a human.

Further taught herein is a pharmaceutical composition comprising a compound of Formula (I) as defined herein and one or more pharmaceutically acceptable carriers, diluents and/or excipients. Also enabled is a cosmetic composition comprising a compound of Formula (I) as defined herein and one or more cosmetically acceptable carriers, diluents and/or excipients.

Further taught herein is the use of a compound of Formula (I) as defined herein or a pharmaceutically acceptable salt thereof in the manufacture of a medicament for the treatment of a mammalian subject in need of therapy. In a related embodiment enabled herein is a compound of Formula (I) as defined herein or a pharmaceutically acceptable salt thereof for use in the treatment of a mammalian subject in need of therapy. In another embodiment, enabled herein is a compound of Formula (I) as defined herein or a pharmaceutically acceptable salt thereof for use in the cosmetic treatment of a mammal to ameliorate the effects of aging. In an embodiment, the mammal is a human.

BRIEF DESCRIPTION OF FIGURES

FIG. 8: Body weight loss; FIG. 9: Stool consistency; FIG. 10: Bloody stools; FIG. 11: Disease activity index. Colitis was chemically induced in mice by administration of 2.5% dextran sulfate sodium (DSS) over 7 days. UTA77 was formulated with food powder (200 mg/kg of body weight) which was orally administered once daily over a period of 7 days.

DESCRIPTION

Figure 1:
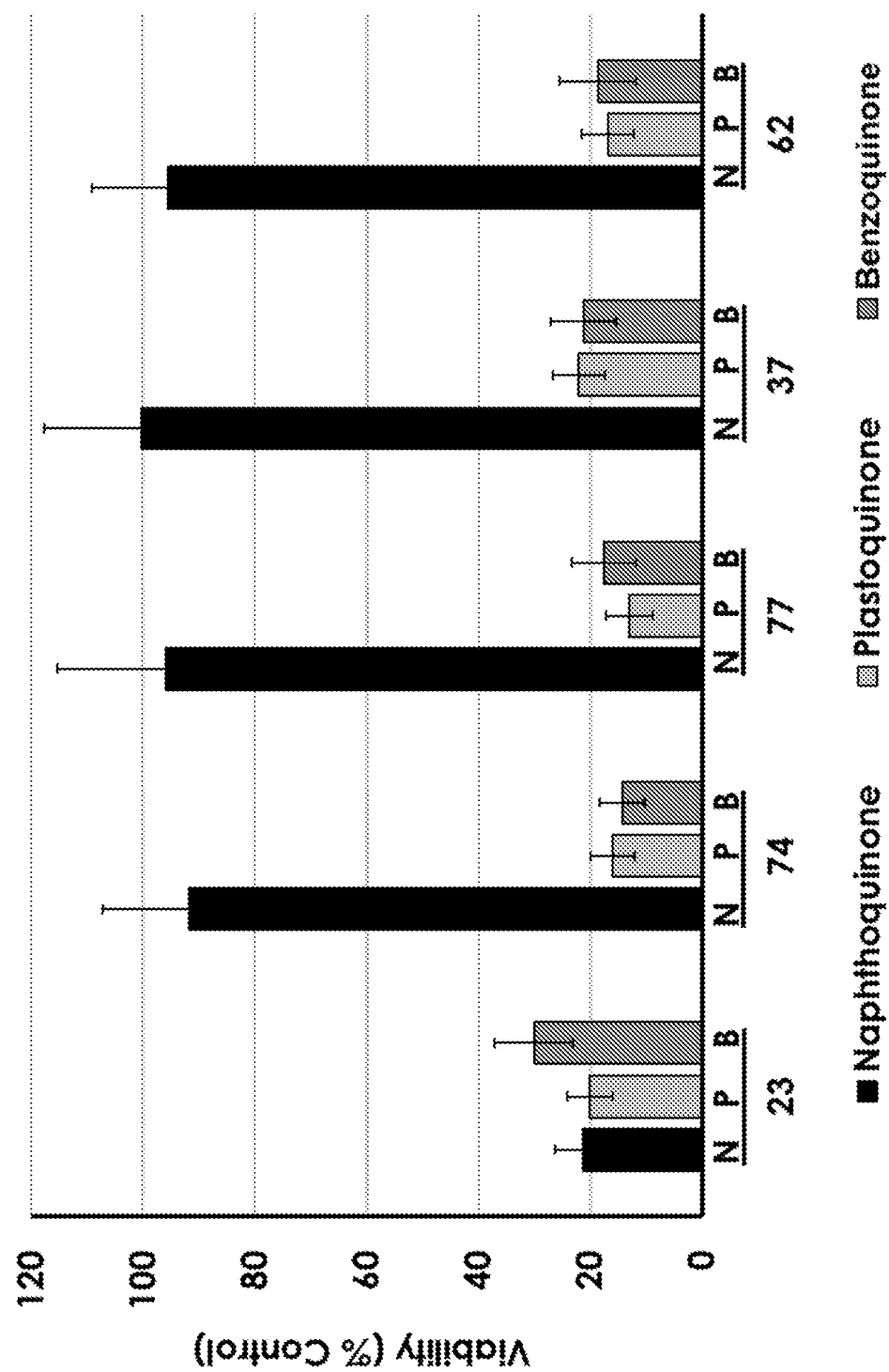
FIG. 1: Cytoprotective effects of compounds of Formula (I) (10 μM) in vitro against rotenone toxicity at 10 M. Representative examples of Formula (I) UTA23, UTA37, UTA62, UTA74, UTA77; control substances were derivatives where the naphthoquinone moiety has been substituted for a benzoquinone or a plastoquinone.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the specification, the singular forms "a", "an" and "the" include plural aspects unless the context clearly dictates otherwise. Thus, for example, reference to "a biological regulator" includes a single biological regulator, as well as two or more biological regulators; reference to "an agent" includes a single agent, as well as two or more agents; reference to "the disclosure" includes a single and multiple aspects taught by the disclosure; and so forth. Aspects taught and enabled herein are encompassed by the term "invention". All such aspects are enabled within the width of the present invention. Any variants and derivatives contemplated herein are encompassed by "forms" of the present invention.

The present invention relates generally to compounds of Formula (I), Formula (Ia) and Formula (Ib) which modulate mitochondrial activity. In an embodiment, the compounds of Formula (I) have utility in enhancing mitochondrial function. In another embodiment, the compounds of Formula (I), Formula (Ia) and Formula (Ib) have utility in restoring mitochondrial dysfunction.

Furthermore, the present invention relates to processes for preparing compounds of Formula (I), Formula (Ia) and Formula (Ib) in relatively few chemical steps and/or in high purity.

As used herein the terms "mitochondrion" and "mitochondria" refer to cytoplasmic organelles which carry out a variety of cellular metabolic functions. The primary function of the mitochondria is to produce energy in the form of adenosine triphosphate (ATP) via oxidative phosphorylation. Mitochondria also play an important role in the process of apoptosis or programmed cell death. Additionally, mitochondria assist in maintaining suitable levels of calcium ions within a cell. In certain cell types, such as the liver cells, mitochondria contribute to detoxification of ammonia. In other contexts, mitochondria contribute to production of blood components as well as hormones, such testosterone and estrogen.

As used herein the term "mitochondrial dysfunction" refers to a reduction in or impairment of typical mitochondrial function in healthy cells, tissues and organs. Mitochondrial dysfunction has been implicated in a wide range of diseases and disorders. In some cases, mitochondrial dysfunction and associated disorders may be caused by acquired or inherited mutations in mitochondrial DNA or in nuclear genes that code for mitochondrial components. In other cases, mitochondrial dysfunction may be due to adverse environmental factors, such as drug use or infection. It is understood that, as used herein, the terms "mitochondrial disease" and "mitochondrial disorder" and related terms may be used interchangeably and encompasses acquired or inherited disorders associated with mitochondrial dysfunction as well as diseases or disorders associated with mitochondrial dysfunction due to adverse environmental factors, unless otherwise specified.

Reference herein to "modulate" or "modulation" extends to and encompasses inhibiting and/or promoting an interaction. Modulation can include, but is not limited to, normalization and enhancement.

Reference herein to "normalization" of or to "normalize" a biomarker refers to changing the level of the biomarker from a pathological value towards a normal value, where the normal value of the energy biomarker can be i) the level of the biomarker in a healthy person or subject, or ii) a level of the energy biomarker that alleviates one or more undesirable symptoms in the person or subject. That is, to normalize an biomarker which is depressed in a disease state means to increase the level of the biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

Reference herein to "enhancement" of or to "enhance" a biomarker refers to changing the level of one or more biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an biomarker may not achieve the optimum outcome for the subject; in such cases, enhancement of one or more biomarkers can be beneficial, for example, higher-than-normal levels of ATP, or lower-than-normal levels of lactic acid (lactate) can be beneficial to such a subject.

The term "amino acid" is used herein in its broadest sense and may refer to compounds having an amino group and a carboxylic acid group. The amino acids incorporated into the peptides of the present invention may be D- or L-forms of proteogenic or naturally occurring amino acids, or may be D- or L-forms of non-proteogenic or non-naturally occurring amino acids. As referred to herein, the term extends to synthetic amino acids and analogues thereof, including salts, isomers, tautomers, esters and N-methylated amino acids.

The term "amino acid side chain" as used herein refers to a group attached to the a carbon, for example, indicated as an R group below:

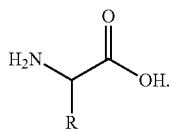

The naturally occurring proteogenic amino acids are shown in Table 1 together with their three letter and one letter codes. L-amino acids are referred to using capital letters or initial capital letters whereas D-amino acids are referred to using lower case letters.

TABLE 1

Codes for conventional amino acids

| Amino acid | L-Three letter code | D-Three letter code | L-One letter code | D-One letter code |
|---|---|---|---|---|
| Alanine | Ala | ala | A | a |
| Arginine | Arg | arg | R | r |
| Asparagine | Asn | asn | N | n |
| Aspartic acid | Asp | asp | D | d |
| Cysteine | Cys | cys | C | c |
| Glutamine | Gln | gln | Q | q |
| Glutamic acid | Glu | glu | E | e |
| Glycine* | Gly | gly | G | g |
| Histidine | His | his | H | h |
| Isoleucine | Ile | ile | I | i |
| Leucine | Leu | leu | L | l |
| Lysine | Lys | lys | K | k |
| Methionine | Met | met | M | m |
| Phenylalanine | Phe | phe | F | f |
| Proline | Pro | pro | P | p |
| Serine | Ser | ser | S | s |
| Threonine | Thr | thr | T | t |
| Tryptophan | Trp | trp | W | w |
| Tyrosine | Tyr | tyr | Y | y |
| Valine | Val | val | V | v |

Examples of unnatural or non-proteogenic amino acids include, but are not limited to, use of ornithine, norleucine, 4-amino butyric acid, 4-amino-3-hydroxy-5-phenylpentanoic acid, 6-aminohexanoic acid, t-butylglycine, norvaline, phenylglycine, sarcosine, 4-amino-3-hydroxy-6-methylheptanoic acid and 2-thienyl alanine. Examples of suitable non-proteogenic or non-naturally occurring amino acids contemplated herein is shown in Table 2.

TABLE 2

Non-conventional amino acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |

TABLE 2-continued

Non-conventional amino acids

| Non-conventional amino acid | Code | Non-conventional amino acid | Code |
|---|---|---|---|
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

The terms "dipeptide" and "tripeptide" as used herein refer to a peptide comprising two and three amino acids residues or derivatives thereof, respectively.

The terms "polypeptide" and "peptide" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "alkyl" as used alone or in combination herein refers to a straight or branched chain saturated hydrocarbon group. The term "$C_{1-12}$ alkyl" refers to such a group containing from one to twelve carbon atoms and "lower alkyl" refers to $C_{1-6}$ alkyl groups containing from one to six carbon atoms, such as methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "$C_{4-9}$ cycloalkyl", for instance, refers to such a group having from 4 to 9 carbon atoms. Examples include cyclobutyl, cyclopentyl and cyclohexyl.

The term "alkenyl" refers to a straight or branched hydrocarbon containing one or more double bonds. The term "$C_{2-12}$ alkenyl", for instance, refers to such a group containing from two to twelve carbon atoms. Examples of alkenyl include allyl, prenyl, geranyl, 1-methylvinyl, butenyl, isobutenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl, and 1,3,5-hexatrienyl.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. The term "$C_{2-12}$ alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The terms "alkanolamino" and "amino alcohol" are used interchangeable in the broadest sense to refer to compounds having an amino group (—NH$_2$, —NHR, and —NR$_2$) and an alcohol or hydroxyl group (—OH). In a preferred embodiment, the compounds of Formula (I), Formula (Ia) and Formula (Ib) or the embodiments mentioned hereinbefore may comprise one or more β-amino alcohols. β-amino alcohols in accordance with the present invention may be a derived from naturally occurring and/or non-conventional amino acids and may thus comprise an "amino acid side chain", for example, indicated as an R group below:

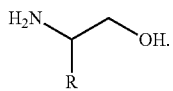

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4-oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3- and 1,3,4-triazolyls), tetrazolyl, thiadiazolyl (including 1,2,3- and 1,3,4-thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The terms "halo" and "halogen" refers to fluoro, chloro, bromo and iodo groups.

The term "halo alkyl" group has one or more of the hydrogen atoms on an alkyl group replaced with halogens. Notable examples are —CF$_3$ or —CF$_2$H.

The term "aryloxy" refers to an aryl group as earlier described linked to the parent structure via an oxygen linkage (—O—). A notable example is phenoxy. Similarly, the term "heteroaryloxy" refers to a heteroaryl group as earlier described linked to the parent structure via an oxygen group. A notable example is a 4, 6 or 7-benzo[b]furanyloxy group.

The term "acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are described herein.

The term "oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

The term "acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl and heterocyclyl are as described herein.

The term "alkylene" refers to a straight or branched divalent alkyl groups preferably having from 1 to 20 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

The term "alkenylene" refers to a straight or branched divalent alkenyl group containing one or more double bonds and preferably having from 2 to 20 carbon atoms. Examples of such alkenylene groups include ethenylene (—CH═CH—), propenylene, prenenylene, geranenylene and isomers thereof.

The term "sulfamoyl" refers to the group —S(O)$_2$NR"R" where each R" is independently hydrogen, alkyl, cycloalkyl, aryl, heteroaryl and heterocyclyl and where each of alkyl, cycloalkyl, aryl, heteroaryl and heterocyclyl are as described herein.

The term "optionally substituted" means that a group may include one or more substituents. One or more hydrogen atoms on the group may be replaced by substituent groups independently selected from halogens (for example halo alkyl such as —CF$_3$ or —CF$_2$H), C$_{1-6}$ alkyl, C$_{2-6}$ alkenyl, C$_{2-6}$ alkynyl, —(CH$_2$)$_v$C$_{3-7}$ cycloalkyl, —(CH$_2$)$_v$C$_{4-7}$ cycloalkenyl, —(CH$_2$)$_v$ aryl, —(CH$_2$)$_v$ heterocyclyl, —(CH$_2$)$_v$ heteroaryl, —C$_6$H$_4$S(O)$_q$C$_{1-6}$ alkyl, —C(Ph)$_3$, —CN, —OR, —O—(CH$_2$)$_{1-6}$—R, —O—(CH$_2$)$_{1-6}$—OR, —OC(O)R, —C(O)R, —C(O)OR, —OC(O)NR'R", —NR'R", —NO$_2$, —NRC(O)R', —NRC(O)NR'R", —NRC(S)NR'R", —NRS(O)$_2$R', —NRC(O)OR', —C(NR)NR'R", —C(═NOR')R, —C(═NOH)NR'R", —C(O)NR'R", —C(═NCN)—NR'R", —C(═NR)NR'R", —C(═NR')SR", —NR'C(═NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$;

where v is 0-6, q is 0-2 and each R, R' and R" is independently selected from H, C$_{1-6}$ alkyl, C$_{2-6}$ alkenyl, C$_{2-6}$ alkynyl, C$_{3-7}$ cycloalkyl, C$_{4-7}$ cycloalkenyl, aryl, heterocyclyl, heteroaryl, C$_{1-6}$ alkylaryl, C$_{1-6}$ alkylheteroaryl, and C$_{1-6}$ alkylheterocyclyl, wherein the alkyl, alkenyl, alkynyl, cycloalkyl, cycloalkenyl, aryl, heterocyclyl, heteroaryl, C$_{1-6}$ alkylaryl, C$_{1-6}$ alkylheteroaryl, or C$_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

In an embodiment the optional substituents may be selected from: halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, silyl, —NH$_2$, —NHC$_{1-4}$ alkyl, —N(C$_{1-4}$ alkyl)$_2$, —CN, —NO$_2$, mercapto, —P═O(OH)(NH$_2$), —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R'" (where R'" is lower alkyl or cycloalkyl) and —S(O)$_2$R'" (where R'" is lower alkyl, cycloalkyl or OH).

Unless otherwise defined and only in respect of the ring atoms of non-aromatic carbocyclic or heterocyclic compounds, the ring atoms of such compounds may also be optionally substituted with one or two ═O groups, instead of or in addition to the above described optional substituents.

When the optional substituent is or contains an alkyl, alkenyl, alkynyl, cycloalkyl, aryl, heteroaryl or heterocyclyl group, the group may itself be optionally substituted with one to six of the same or different substituents selected from halogen, C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —P═O(OH)(NH$_2$), —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R'" (where R'" is lower alkyl or cycloalkyl) and —S(O)$_2$R'" (where R'" is lower alkyl, cycloalkyl or OH).

As described above, in one aspect there is provided compounds of Formula (I):

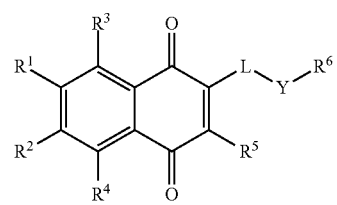

Formula (I)

or a pharmaceutically acceptable salt thereof, wherein

R$^1$, R$^2$, R$^3$ and R$^4$ are each independently selected from H, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, halogen, optionally substituted C$_1$-C$_6$ alkylhalo; optionally substituted C$_1$-C$_6$ thioalkyl, —SR, —NRR', optionally substituted C$_3$-C$_7$ cycloalkyl, optionally substituted C$_2$-C$_{12}$ heterocyclyl, optionally substituted C$_5$-C$_{12}$ aryl, and optionally substituted C$_2$-C$_{12}$ heteroaryl, R$^5$ is selected from H, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, halogen, optionally substituted C$_1$-C$_6$ alkylhalo; optionally substituted C$_1$-C$_6$ thioalkyl, —SR, —NRR', optionally substituted C$_3$-C$_7$ cycloalkyl, optionally substituted C$_2$-C$_{12}$ heterocyclyl, optionally substituted C$_5$-C$_{12}$ aryl, and optionally substituted C$_2$-C$_{12}$ heteroaryl, L is a divalent linker selected from a bond, optionally substituted C$_1$-C$_{20}$ alkylene, optionally substituted C$_1$-C$_{20}$ alkenylene, optionally substituted C$_1$-C$_{20}$ alkynylene;

Y is absent or is a divalent linker selected from optionally substituted C$_3$-C$_6$ cycloalkylene, optionally substituted C$_2$-C$_{12}$ heterocyclyl, optionally substituted C$_5$-C$_{12}$ arylene, optionally substituted C$_2$-C$_{12}$ heteroarylene, —C(O)—NR—, —C(O)—NR—(CH$_2$)$_y$—, —C(O)—O—, —C(O)—OR—, —C(O)—O—(CH$_2$)$_y$—, —C(O)—, —C(CX$_3$)—NR—, —CRR'X—NR—, —NR—C(O)—NR'—, —O—C(O)O—, —C═N—O—, —SO$_2$—NR—, —(CH$_2$)$_x$—NR—, —(CH$_2$)$_y$—S—(CH$_2$)$_z$—, —(CH$_2$)$_y$—O—(CH$_2$)$_z$—, wherein y and z are each integers independently selected from 0, 1, 2, 3 and 4;

R$^6$ is selected from H, —COOR, —OR, —NRR', —SR, optionally substituted C$_1$-C$_{20}$ alkyl, optionally substituted C$_2$-C$_{20}$ alkenyl, optionally substituted C$_2$-C$_{20}$ alkynyl; optionally substituted C$_3$-C$_7$ cycloalkyl, optionally substituted C$_5$-C$_{12}$ aryl, optionally substituted C$_2$-C$_{12}$ heteroaryl or optionally substituted C$_2$-C$_{12}$ heterocyclyl, optionally substituted C$_1$-C$_6$ alkanolamino, optionally substituted amino acid, optionally substituted dipeptide, optionally substituted tripeptide, and optionally substituted polypeptide, or Y and $R^6$ taken together form a group selected from —C(O)—[NR$^7$—C(R$^8$)(R$^9$)—C(O)]$_w$—OR$^{10}$;

—C(O)—[NR$^7$—C(R$^8$)(R$^9$)—C(R$^{11}$)(R$^{12}$)]$_w$—OR$^{10}$;

—[NR$^7$—C(R$^8$)(R$^9$)—C(O)]$_w$—OR$^{10}$; and

—[NR$^7$—C(R$^8$)(R$^9$)—C(R$^{11}$)(R$^{12}$)]$_w$—OR$^{10}$, wherein $R^7$, $R^8$, $R^{10}$, $R^{11}$ and $R^{12}$ at each occurrence are H or optionally substituted $C_1$-$C_6$-alkyl; $R^9$ at each occurrence is independently selected from H and an amino acid side chain or a derivative thereof; and w is an integer from 0 to 20;

R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl, and X is a halogen.

In another aspect, there is provided compounds of Formula (Ia):

Formula (Ia)

[Chemical structure: naphthoquinone with L-Y-R$^6$ substituent and R$^5$ substituent]

or a pharmaceutically acceptable salt thereof, wherein:

$R^5$ is selected from H and optionally substituted $C_1$-$C_6$ alkyl

L is optionally substituted $C_1$-$C_{20}$ alkylene,

Y is a divalent linker selected from optionally substituted —C(O)—NR—, —C(O)—NR—(CH$_2$)$_y$—, —C(O)—O—, —C(O)—, —(CH$_2$)$_y$—S—(CH$_2$)$_z$—, —(CH$_2$)$_y$—O—(CH$_2$)$_z$—, wherein y and z are each integers independently selected from 0, 1, 2, 3 and 4;

$R^6$ is selected from H, —COOR; optionally substituted $C_5$-$C_{12}$ aryl, optionally substituted $C_2$-$C_{12}$ heteroaryl, optionally substituted $C_1$-$C_6$ alkanolamino, optionally substituted amino acid, or Y and $R^6$ taken together form a group selected from —C(O)—[NR$^7$—C(R$^8$)(R$^9$)—C(O)]$_w$—OR$^{10}$;

—C(O)—[NR$^7$—C(R$^8$)(R$^9$)—C(R$^{11}$)(R$^{12}$)]$_w$—OR$^{10}$ wherein $R^7$, $R^8$, $R^{10}$, $R^{11}$ and $R^{12}$ at each occurrence are H or optionally substituted $C_1$-$C_6$-alkyl; $R^9$ at each occurrence is independently selected from H and an amino acid side chain or a derivative thereof; and w is an integer from 0 to 20;

R and R' are independently H, optionally substituted $C_1$-$C_6$ alkyl.

In another aspect, there is provided compounds of Formula (Ib):

Formula (Ib)

[Chemical structure: naphthoquinone with -(CH$_2$)$_n$-C(O)-N(R)-(CR$^{13}$)$_m$-R$^6$ substituent and R$^5$ substituent]

or a pharmaceutically acceptable salt thereof, wherein:

$R^5$ is selected from H and methyl, $R^6$ is selected from H, —COOR, —OH, optionally substituted $C_5$-$C_{12}$ aryl, optionally substituted $C_2$-$C_{12}$ heteroaryl, R is H or optionally substituted $C_1$-$C_6$ alkyl;

$R^{13}$ at each occurrence is independently selected from H, optionally substituted phenyl, and optionally substituted benzyl, n is an integer selected from 1, 2, 3, 4 and 5, and m is an integer selected from 0, 1, 2, and 3.

In an embodiment, L is any suitable divalent linker group. In one embodiment, L is a bond. In other embodiments, L is a divalent linker group selected from optionally substituted $C_1$-$C_{20}$ alkylene, optionally substituted $C_1$-$C_{20}$ alkenylene, optionally substituted $C_1$-$C_{20}$ alkynylene. In one preferred embodiment, L is $C_2$ alkylene. In another preferred embodiment, L is $C_3$ alkylene. In another preferred embodiment, L is $C_4$ alkylene. In another preferred embodiment, L is $C_5$ alkylene. In another preferred embodiment, L is $C_{10}$ alkylene.

In an embodiment, Y is absent or is any suitable divalent linker group. In one embodiment, Y is absent. In another embodiment, Y is a divalent linker group selected from optionally substituted $C_3$-$C_6$ cycloalkylene, optionally substituted $C_2$-$C_{12}$ heterocyclyl, optionally substituted $C_5$-$C_{12}$ arylene, optionally substituted $C_2$-$C_{12}$ heteroarylene, —C(O)—NR—, —C(O)—NR—(CH$_2$)—, —C(O)—O—, —C(O)—OR—, —C(O)—O—(CH$_2$)$_y$—, —C(O)—, —C(CX$_3$)—NR—, —CRR'X—NR—, —NR—C(O)—NR'—, —O—C(O)O—, —C≡N—O—, —SO$_2$—NR—, —(CH$_2$)$_x$—NR—, —(CH$_2$)$_y$—S—(CH$_2$)$_z$—, —(CH$_2$)$_y$—O—(CH$_2$)$_z$—, wherein y and z are each integers independently selected from 0, 1, 2, 3 and 4; R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl, and X is a halogen. In another preferred embodiment, Y is —C(O)—NH—. In another preferred embodiment, Y is —C(O)—. In a further preferred embodiment, Y is —S—. In a further preferred embodiment, Y is —S—(CH$_2$)$_2$-. In another preferred embodiment Y is —O—. In another preferred embodiment Y is —C(O)—NR—(CH$_2$)$_y$—. In another preferred embodiment Y is —C(O)—NH—(CH$_2$)$_2$—.

In an embodiment, $R^1$, $R^2$, $R^3$ and $R^4$ are independently selected from H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, halogen, optionally substituted $C_1$-$C_6$ alkylhalo; optionally substituted $C_1$-$C_6$ thioalkyl, —SR, —NRR', optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl; wherein R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl. In a preferred embodiment, one or more of $R^1$, $R^2$, $R^3$ and $R^4$ are H. In another preferred embodiment $R^1$ is H. In another preferred embodiment, $R^2$ is H. In another preferred embodiment, $R^3$ is H. In another preferred embodiment, $R^4$ is H.

In an embodiment, $R^5$ is selected from H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, halogen, optionally substituted $C_1$-$C_6$ alkylhalo; optionally substituted $C_1$-$C_6$ thioalkyl, —SR, —NRR', optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl, wherein R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl. In a preferred embodiment, $R^5$ is H. In another preferred embodiment, $R^5$ is methyl.

In an embodiment, $R^6$ is selected from H, —OR, —C(O)OR, C(O)NR, —NRR', —SR, optionally substituted $C_1$-$C_{20}$ alkyl, optionally substituted $C_2$-$C_{20}$ alkenyl, optionally substituted $C_2$-$C_{20}$ alkynyl; optionally substituted $C_3$-$C_7$ cycloalkyl, optionally substituted $C_5$-$C_{12}$ aryl, optionally substituted $C_2$-$C_{12}$ heteroaryl or optionally substituted $C_2$-$C_{12}$ heterocyclyl, optionally substituted $C_1$-$C_6$ alkanolamino, optionally substituted amino acid, optionally substituted dipeptide, optionally substituted tripeptide, and optionally substituted polypeptide, wherein R and R' are independently H, optionally substituted $C_1$-$C_6$ alkyl, optionally substituted $C_3$-$C_7$ cycloalkyl, optionally substituted $C_2$-$C_{12}$ heterocyclyl, optionally substituted $C_5$-$C_{12}$ aryl, and optionally substituted $C_2$-$C_{12}$ heteroaryl. In a preferred embodiment, $R^6$ is H. In other preferred embodiments, $R^6$ is optionally substituted $C_5$-$C_{12}$ aryl. In other preferred embodiments, $R^6$ is optionally substituted $C_6$ aryl. In further preferred embodiments, $R^6$ is a $C_5$-$C_{12}$ aryl substituted by one or more alkoxy groups. In other preferred embodiments, $R^6$ is a $C_5$-$C_{12}$ aryl substituted by one or more methoxy groups. In further preferred embodiments, $R^6$ is a $C_6$ aryl substituted by two methoxy groups. In further preferred embodiments, $R^6$ is a 3,4-dimethoxy phenyl. In other preferred embodiments, $R^6$ is a group derived from an amino acid. In other preferred embodiments, $R^6$ is a group derived from an amino alcohol. In further preferred embodiments, $R^6$ is a group derived from phenyl alanine.

In other embodiments, Y and $R^6$ may be taken together form a group of formula

—C(O)—[NR$^7$—C(R$^8$)(R$^9$)—C(O)]$_w$—OR$^{10}$    a)

—C(O)—[NR$^7$—C(R$^8$)(R$^9$)—C(R$^{11}$)(R$^{12}$)]$_w$—OR$^{10}$    b)

—[NR$^7$—C(R$^8$)(R$^9$)—C(O)]$_w$—OR$^{10}$; or    c)

—[NR$^7$—C(R$^8$)(R$^9$)—C(R$^{11}$)(R$^{12}$)]$_w$—OR$^{10}$    d)

wherein $R^7$, $R^8$, $R^{10}$, $R^{11}$ and $R^{12}$ at each occurrence are H or optionally substituted $C_1$-$C_6$-alkyl; $R^9$ at each occurrence is independently selected from H and an amino acid side chain or a derivative thereof; and w is an integer from 0 to 20. In some embodiments, $R^7$ is H. In some embodiments, R is H. In some embodiments, $R^1$ is H. In some embodiments, $R^{12}$ is H. In some embodiments, $R^{10}$ is selected from H, methyl, ethyl, propyl and t-butyl. In some embodiments, w is an integer from 0 to 10. In some embodiments, w is 1. In some embodiments, w is 2. In some embodiments, w is 3. In some embodiments, $R^9$ is H or an amino acid side chain or a derivative thereof selected from the group consisting of

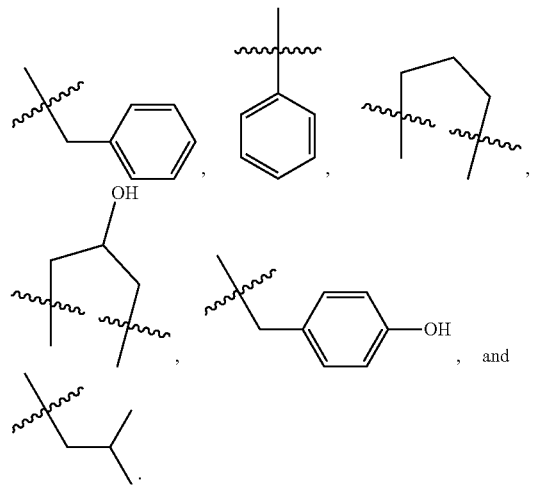

In some embodiments, Y and $R^6$ are taken together form a group of formula —C(O)—[NR$^7$—C(R$^8$)(R$^9$)—C(O)]$_w$—OR$^{10}$ wherein $R^7$, $R^8$ and $R^{10}$ are H, $R^9$ is

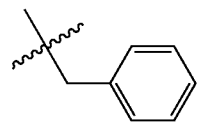 [SMILES: *Cc1ccccc1]

and w is 1.

With respect to Formula (I) compounds disclosed herein the following combinations of any one or more of (i) to (viii) are contemplated:
(i) $R^1$ is H;
(ii) $R^2$ is H;
(iii) $R^3$ is H;
(iv) $R^4$ is H;
(v) $R^5$ is H; or
    $R^5$ is methyl;
(vi) L is a bond; or
    L is $C_2$ alkylene; or
    L is $C_3$ alkylene; or
    L is $C_4$ alkylene; or
    L is $C_5$ alkylene; or
    L is $C_{10}$ alkylene;
(vii) Y is absent; or
    Y is —C(O)—NH—; or
    Y is —C(O)—NH—(CH$_2$)$_y$—; or
    Y is —C(O)—NH—(CH$_2$)$_2$—; or
    Y is —C(O)—O—; or
    Y is —C(O)—; or
    Y is —S—; or
    Y is —S—(CH$_2$)$_2$—; or
    Y—O—;
(viii) $R^6$ is H; or
    $R^6$ is —COOH; or
    $R^6$ is -phenyl; or
    $R^6$ is -3,4-dimethoxy phenyl; or $R^6$ is heteroaryl; or
$R^6$ is an amino acid or a derivative thereof; or
$R^6$ is a an amino alcohol or a derivative thereof; or
Y and $R^6$ taken together form a group of formula —C(O)—[NR$^7$—C(R$^8$)(R$^9$)—C(O)]$_w$—OR$^{10}$  a)

—C(O)—[NR$^7$—C(R$^8$)(R$^9$)—C(R$^{11}$)(R$^{12}$)]$_w$—OR$^{10}$;  b)

—[NR$^7$—C(R$^8$)(R$^9$)—C(O)]$_w$—OR$^{10}$; or  c)

—[NR$^7$—C(R$^8$)(R$^9$)—C(R$^{11}$)(R$^{12}$)]$_w$—OR$^{10}$,  d)

wherein $R^7$, $R^8$, $R^9$, $R^{10}$, $R^{11}$ and $R^{12}$ and w are as previously defined.

Representative compounds of Formula (I) include:

TABLE 3

Representative compounds of Formula (I)

| Designated No. | Structure |
| --- | --- |
| UTA #2 | (2-methyl-3-(11-hydroxyundecyl)-1,4-naphthoquinone structure) |
| UTA #19 | (2-methyl-3-butyl-1,4-naphthoquinone structure) |
| UTA #20 | (2-methyl-3-(3,4-dimethoxybenzyl)-1,4-naphthoquinone structure) |
| UTA #21 | (2-methyl-3-heptyl-1,4-naphthoquinone structure) |
| UTA #22 | (2-methyl-3-(2-cyclopentylethyl)-1,4-naphthoquinone structure) |
| UTA #23 | (2-methyl-3-(3-carboxypropyl)-1,4-naphthoquinone structure) |

TABLE 3-continued

Representative compounds of Formula (I)

| Designated No. | Structure |
| --- | --- |
| UTA #24 | 2-(3-hydroxybutyl)-3-methylnaphthalene-1,4-dione |
| UTA #35 | methyl (S)-2-(4-(3-methyl-1,4-dioxo-1,4-dihydronaphthalen-2-yl)butanamido)-3-phenylpropanoate |
| UTA #37 | (S)-2-(4-(3-methyl-1,4-dioxo-1,4-dihydronaphthalen-2-yl)butanamido)-3-phenylpropanoic acid |
| UTA #42 | tert-butyl (S)-1-(4-(3-methyl-1,4-dioxo-1,4-dihydronaphthalen-2-yl)butanoyl)pyrrolidine-2-carboxylate |
| UTA #43 | (S)-1-(4-(3-methyl-1,4-dioxo-1,4-dihydronaphthalen-2-yl)butanoyl)pyrrolidine-2-carboxylic acid |
| UTA #46 | 3-((3-methyl-1,4-dioxo-1,4-dihydronaphthalen-2-yl)thio)propanoic acid |
| UTA #47 | tert-butyl (4-(3-methyl-1,4-dioxo-1,4-dihydronaphthalen-2-yl)butanoyl)glycinate |

TABLE 3-continued

Representative compounds of Formula (I)

| Designated No. | Structure |
| --- | --- |
| UTA #54 | *naphthoquinone with methyl group, propyl chain linked to amide of L-leucine (carboxylic acid)* |
| UTA #55 | *methylnaphthoquinone with propyl chain linked to amide of L-tyrosine tert-butyl ester* |
| UTA #59 | *naphthoquinone with propyl-carboxylic acid chain* |
| UTA #61 | *methylnaphthoquinone with propyl chain linked to prolinol amide* |
| UTA #62 | *methylnaphthoquinone with propyl chain linked to amide of phenylalaninol* |
| UTA #65 | *methylnaphthoquinone with ethyl chain linked to amide of L-phenylalanine tert-butyl ester* |

TABLE 3-continued
Representative compounds of Formula (I)
Designated No. Structure
UTA #66
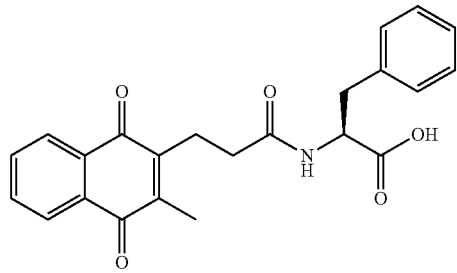 [SMILES: CC1=C(CCC(=O)N[C@@H](Cc2ccccc2)C(=O)O)C(=O)c2ccccc2C1=O]
UTA #67
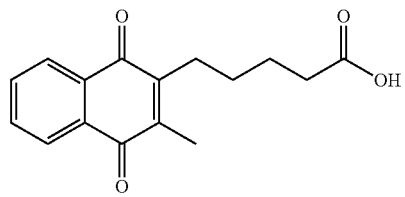 [SMILES: CC1=C(CCCCC(=O)O)C(=O)c2ccccc2C1=O]
UTA #70
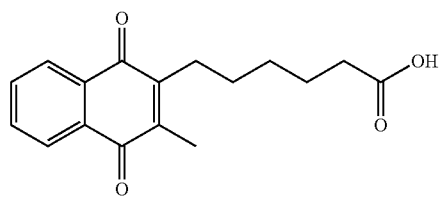 [SMILES: CC1=C(CCCCCC(=O)O)C(=O)c2ccccc2C1=O]
UTA #71
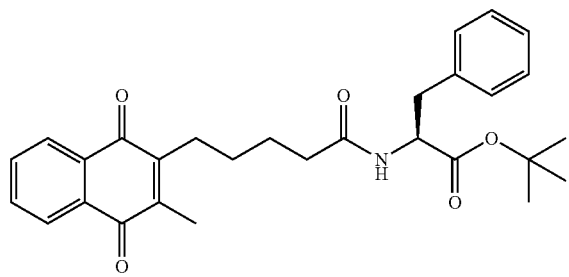 [SMILES: CC1=C(CCCCC(=O)N[C@@H](Cc2ccccc2)C(=O)OC(C)(C)C)C(=O)c2ccccc2C1=O]
UTA #72
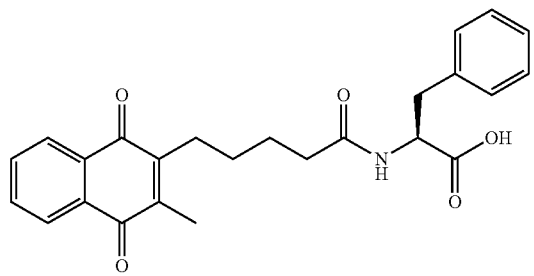 [SMILES: CC1=C(CCCCC(=O)N[C@@H](Cc2ccccc2)C(=O)O)C(=O)c2ccccc2C1=O]
UTA #73
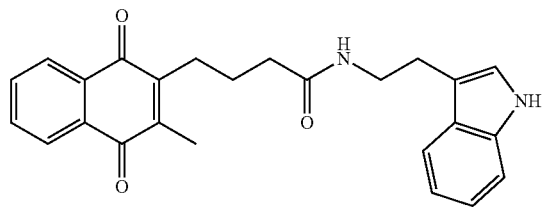 [SMILES: CC1=C(CCCC(=O)NCCc2c[nH]c3ccccc23)C(=O)c2ccccc2C1=O]

TABLE 3-continued

Representative compounds of Formula (I)

| Designated No. | Structure |
| --- | --- |
| UTA #74 | 2-methyl-1,4-naphthoquinone with -(CH2)3-C(=O)-NH-CH2CH2-(4-hydroxyphenyl) |
| UTA #75 | 2-methyl-1,4-naphthoquinone with -(CH2)5-C(=O)-NH-CH(CH2Ph)-C(=O)-O-tBu |
| UTA #76 | 2-methyl-1,4-naphthoquinone with -(CH2)5-C(=O)-NH-CH(CH2Ph)-COOH |
| UTA #77 | 2-methyl-1,4-naphthoquinone with -(CH2)3-C(=O)-NH-CH2CH2-(3,4-dimethoxyphenyl) |
| UTA #78 | 2-methyl-1,4-naphthoquinone with -(CH2)3-C(=O)-NH-CH(CH2Ph)-CH2OH |
| UTA #80 | 2-methyl-1,4-naphthoquinone with -(CH2)3-C(=O)-NH-CH(Ph)-CH2OH |
| UTA #81 | 2-methyl-1,4-naphthoquinone with -(CH2)3-C(=O)-NH-CH(Ph)-CH2OH (enantiomer) |

TABLE 3-continued
Representative compounds of Formula (I)
Designated No. Structure
UTA #84 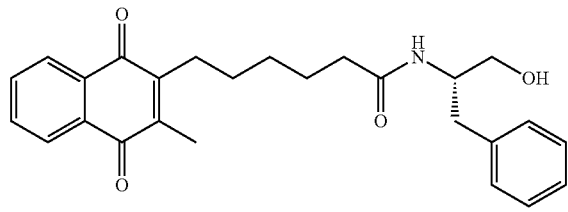 [SMILES: CC1=C(CCCCCC(=O)N[C@H](CO)Cc2ccccc2)C(=O)c2ccccc2C1=O]
UTA #88 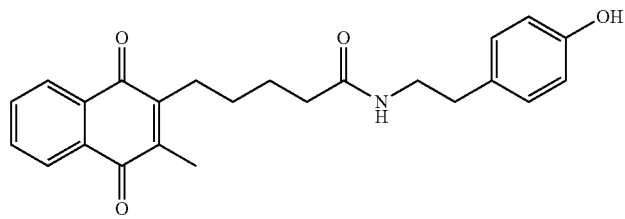 [SMILES: CC1=C(CCCCC(=O)NCCc2ccc(O)cc2)C(=O)c2ccccc2C1=O]
UTA #89 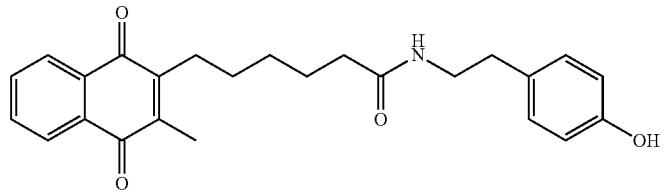 [SMILES: CC1=C(CCCCCC(=O)NCCc2ccc(O)cc2)C(=O)c2ccccc2C1=O]
UTA #91 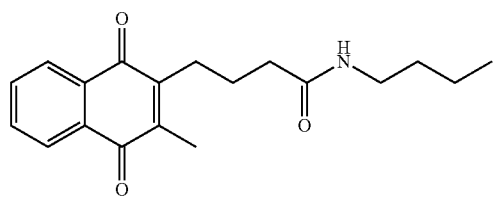 [SMILES: CCCCNC(=O)CCCC1=C(C)C(=O)c2ccccc2C1=O]
UTA #93 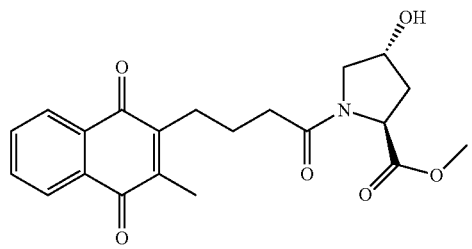 [SMILES: COC(=O)[C@@H]1C[C@@H](O)CN1C(=O)CCCC1=C(C)C(=O)c2ccccc2C1=O]
UTA #94 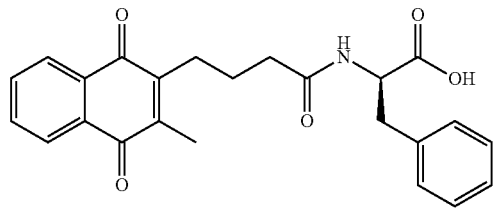 [SMILES: CC1=C(CCCC(=O)N[C@H](Cc2ccccc2)C(=O)O)C(=O)c2ccccc2C1=O]
UTA #95 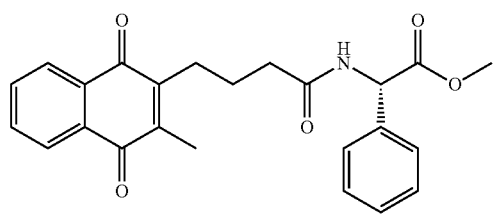 [SMILES: COC(=O)[C@@H](NC(=O)CCCC1=C(C)C(=O)c2ccccc2C1=O)c1ccccc1]

TABLE 3-continued

Representative compounds of Formula (I)

| Designated No. | Structure |
|---|---|
| UTA #97 | 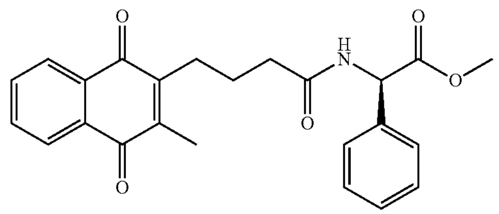 [SMILES: COC(=O)[C@H](NC(=O)CCCC1=C(C)C(=O)c2ccccc2C1=O)c1ccccc1] |
| UTA #113 | 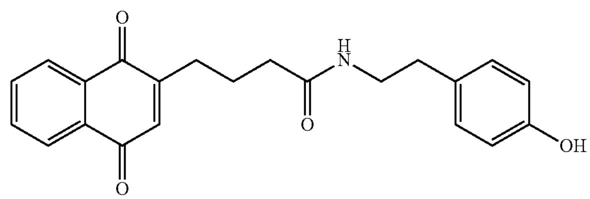 [SMILES: O=C(CCCC1=CC(=O)c2ccccc2C1=O)NCCc1ccc(O)cc1] |
| UTA #115 | 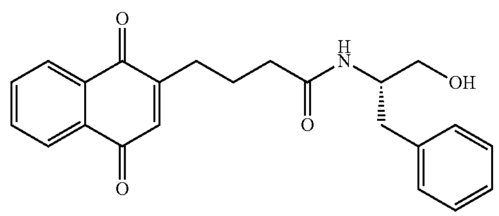 [SMILES: O=C(CCCC1=CC(=O)c2ccccc2C1=O)N[C@H](CO)Cc1ccccc1] |
| UTA #116 | 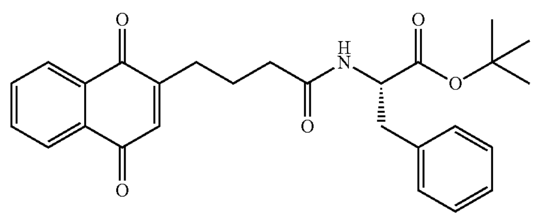 [SMILES: CC(C)(C)OC(=O)[C@H](Cc1ccccc1)NC(=O)CCCC1=CC(=O)c2ccccc2C1=O] |
| UTA #117 | 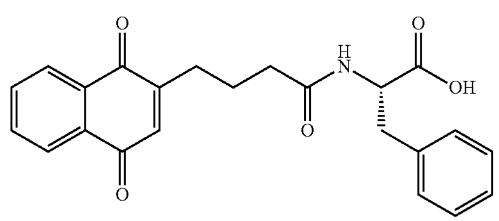 [SMILES: O=C(CCCC1=CC(=O)c2ccccc2C1=O)N[C@@H](Cc1ccccc1)C(=O)O] |

The salts of the compounds of Formula (I), Formula (Ia) and Formula (Ib) or the embodiments mentioned hereinbefore are preferably pharmaceutically acceptable, but it will be appreciated that non-pharmaceutically acceptable salts also fall within the scope of the present invention, since these are useful as intermediates in the preparation of pharmaceutically acceptable salts. The salts may also be cosmetically acceptable insofar as the compounds are used for anti-aging purposes.

It will be appreciated that the compounds of Formula (I), Formula (Ia) and Formula (Ib) or the embodiments mentioned hereinbefore, and the salts thereof, can be presented in the form of pharmaceutically acceptable derivatives. The term "pharmaceutically acceptable derivative" includes pharmaceutically acceptable esters, prodrugs, solvates and hydrates of the compounds of Formula (I), Formula (Ia) or Formula (Ib) or salts thereof. Pharmaceutically acceptable derivatives may include any pharmaceutically acceptable hydrate or any other compound or prodrug which, upon administration to a subject, is capable of providing (directly or indirectly) a compound of Formula (I), or an active metabolite or residue thereof.

The pharmaceutically acceptable salts include acid addition salts, base addition salts, and the salts of quaternary amines and pyridiniums. The acid addition salts are formed from a compound of the subject invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternized with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of Formula (I), Formula (Ia) and Formula (Ib) or embodiments mentioned hereinbefore may be in crystalline form and/or as solvates (e.g. hydrates) and it is intended that both forms be within the scope of the present invention. The term "solvate" is a complex of variable stoichiometry formed by a solute and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the subject invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of Formula (I), Formula (Ia) and Formula (Ib) or the embodiments mentioned hereinbefore is within the scope and spirit of the subject invention.

The term "pharmaceutically acceptable ester" includes biologically acceptable esters of compound of Formula (I), Formula (Ia) and Formula (Ib) or embodiments mentioned hereinbefore, such as sulphonic, phosphonic and carboxylic acid derivatives.

Thus, in another aspect of the present invention, there is provided a prodrug or pharmaceutically acceptable ester of a compound of the subject invention or of salt thereof.

It will be appreciated that the compounds of the subject invention have at least one asymmetric centre, and therefore are capable of existing in more than one stereoisomeric form. The present invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds of Formula (I), Formula (Ia) and Formula (Ib) or embodiments mentioned hereinbefore being included in the present invention.

The present invention also includes where possible a salt or pharmaceutically acceptable derivative such as a pharmaceutically acceptable ester, solvate and/or prodrug of the above mentioned embodiments of the subject invention.

In another aspect of the present invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent. Still a further aspect of the subject invention is a cosmetic composition that comprises a cosmetically effective amount of one or more of the aforementioned compounds or pharmaceutically or cosmetically acceptable salts thereof, including pharmaceutically acceptable derivatives thereof, and optionally a pharmaceutically acceptable carrier or diluent. A cosmetic formulation is useful to ameliorate the effects of aging and may be referred to as an anti-aging formulation.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), ocular, vaginal or parenteral (including intramuscular, sub-cutaneous and intravenous) administration or in a form suitable for administration by inhalation or insufflation.

The compounds of either Formula (I), Formula (Ia) or Formula (Ib) or the embodiments mentioned hereinbefore, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of Formula (I), Formula (Ia) and Formula (Ib) or embodiments mentioned hereinbefore can be administered in a wide variety of oral, topical, ocular and parenteral dosage forms. It will be obvious to those skilled in the art that the following dosage forms may comprise, as the active component, either a compound of Formula (I), Formula (Ia) and Formula (Ib) or a pharmaceutically acceptable salt thereof.

For preparing pharmaceutical compositions from the compounds of Formula (I), Formula (Ia) or Formula (Ib) or the embodiments mentioned hereinbefore, pharmaceutically acceptable carriers can be either solid or liquid. Solid form preparations include powders, tablets, pills, capsules, cachets, suppositories, dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups, elixirs, or sterile ocular solutions. The active ingredient can be dissolved or suspended in a pharmaceutically acceptable carrier, such as sterile water, sterile organic solvent or a mixture of both.

The compounds of Formula (I), Formula (Ia) and Formula (Ib) or the embodiments mentioned hereinbefore may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the subject invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention a compound of Formula (I), Formula (Ia) or Formula (Ib) may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

For ocular administration, the compounds according to the invention may be formulated as a sterile ocular solution or as an ocular delivery device (such as a contact lens and the like facilitating immediate release, timed release, or sustained release). For ocular administration, the composition is preferably in the form of an ophthalmic composition. Ophthalmic compositions are preferably formulated as eyedrop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a surfactant; thickening agents; an anti-oxidant; ethanol and other excipients such as an isotonic agent, buffer, preservative, and/or pH-controlling agent. The pH of the ophthalmic composition is desirably within the range of 4 to 8.

When desired, formulations adapted to give sustained release of the active ingredient may be employed. Furthermore, the formulations may be in a form suitable for cosmetic use to ameliorate the effects of aging.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The present invention also includes compounds of Formula (I), Formula (Ia) and Formula (Ib) or embodiments mentioned hereinbefore in the absence of carrier where the compounds are in unit dosage form.

The amount of the compound of Formula (I), Formula (Ia) and Formula (Ib) or the embodiments mentioned hereinbefore to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds of Formula (I), Formula (Ia) and Formula (Ib) or embodiments mentioned hereinbefore may be co-administered with one or more other active agents in combination therapy. For example the pharmaceutical preparation of the active compound may be co-administered (for example, separately, concurrently or sequentially), with one or more other agents used to treat diseases or disorders associated with mitochondrial dysfunction. For example, pharmaceutical preparations of the compounds of the subject invention may be co-administered with other mitochondrial protective agents or antioxidant compounds or a component which modulates energy metabolism such as precursors or products of cellular respiratory. In some embodiments, a pharmaceutical composition further comprising an anti-diabetic agent as an additional active agent is provided.

Furthermore, pharmaceutical preparations of the active compounds may be co-administered (for example, separately, concurrently or sequentially) treat, prevent, ameliorate or reduce drug-induced or environmental-induced mitochondrial dysfunction. For example, pharmaceutical preparations of the active compounds may be co-administered with other active agents having a negative effect on mitochondrial activity or function, to treat, prevent, ameliorate or reduce the resultant drug- or environmental-induced mitochondrial dysfunction. Examples of other active agents having a negative effect on mitochondrial activity or function include an antiviral; an anti-cancer agent; an antibiotic; a CNS drug; a hypertensiondrug; an anthracyclines; a non-steroidal anti-inflammatory drug (NSAID); an anestetic; a beta-blocker; an anti-arrhythmic; an anti-diabetic; an anti-inflammatory; or another agent. Accordingly, it is envisaged that pharmaceutical preparations of compounds of Formula (I) may be co-administered to treat, prevent, ameliorate or reduce negative effect on mitochondrial activity or function associated with the administration of other active agents.

Examples of antivirals having a negative effect on mitochondrial activity or function include abacavir, didanosine, emtricitabine, entecavir, emtricitabine, lamivudine, nevirapine, telbivudine, tenofovir, tipranavir, stavudine, zalcitabine, and zidovudine. Examples of anti-cancer agents having a negative effect on mitochondrial activity or function include arsenic trioxide, cetuximab, dacarbazine, denileukin, diftitox, flutamide, gemtuzumab, methotrexate, mitoxantrone, pentostatin, and tamoxifen. Examples of antibiotics having a negative effect on mitochondrial activity or function include antimycin A, isoniazid, chloramphenicol, ethambutol, gentamycin, ketoconazole, linezolid, streptozocin, streptomycin, tobramycin, tetracyclines, and trovafloxacin. Examples of CNS drugs having a negative effect on mitochondrial activity or function include amitriptyline, amphetamines, atomoxetin, chlorpromazine, cocaine, dantrolene, desipramine, divalproex, droperidol, felbamate, fluphenazine, imipramine, methamphetamine, naltrexone, nefazodone, pergolide, and valproic acid. Examples of hypertension drugs having a negative effect on mitochondrial activity or function include bosentan. Examples of anthracyclines having a negative effect on mitochondrial activity or function include daunorubicin, doxorubicin, epirubicin, and idarubicin. Examples of non-steroidal anti-inflammatory drugs (NSAIDs) having a negative effect on mitochondrial activity or function include aspirin, celecoxib, diclofenac, diflunisal, etodolac, fenoprofen, ibuprofen, indomethacin, ketoprofen, mefenamic acid, meloxicam, naproxen, nabumetone, oxaprozin, piroxicam, salsalate, sulindac, thioridazine, and tolmetin. Examples of anestetics having a negative effect on mitochondrial activity or function include bupivacaine and isoflurane. Examples of beta-blockers having a negative effect on mitochondrial activity or function include atenolol. Example of anti-arrhythmics having a negative effect on mitochondrial activity or function include amiodarone, disopyramide, dofetilide, and ibutilide. Examples of anti-diabetics having a negative effect on mitochondrial activity or function include pioglitazone and rosiglitazone. Examples of anti-inflammatory agents having a negative effect on mitochondrial activity or function include prednisolone, dexamethasone, hydrocortisone, and triamcilone. Examples of other agents having a negative effect on mitochondrial activity or function include clioquinol, cyanide, hexachlorophene, rotenone, and statins. By way of example, it is envisaged that pharmaceutical preparations of compounds of Formula (I) may be co-administered to treat, prevent, ameliorate or reduce negative effect on mitochondrial activity or function associated with the administration of other active agents.

The term "therapeutically effective amount" refers to that amount which is sufficient to effect treatment, as defined above, when administered to a subject, such as a mammal, including a human in need of such treatment. The therapeutically effective amount will vary depending on the subject and disease state being treated, the severity of the affliction and the manner of administration, and may be determined routinely by one of ordinary skill in the art.

The term "treatment" as used herein covers any treatment of a condition or disease in an animal, preferably a mammal, more preferably a human, and includes: (i) preventing the disease or condition from occurring in a subject which may be predisposed to the disease but has not yet been diagnosed as having it; (ii) inhibiting the disease or condition, i.e. arresting its development; (iii) relieving the disease or condition, i.e. causing regression of By "treatment" also includes cosmetic treatment, which includes non-therapeutic cosmetic treatment to ameliorate the effects of aging.

Enabled herein is a method of treatment of a mammalian subject comprising the administration of a compound Formula (I), Formula (Ia) and Formula (Ib) as defined herein or a pharmaceutically acceptable salt or compositions thereof. It is considered that the compounds of Formula (I) and pharmaceutical compositions thereof enabled herein are useful in the prophylaxis and/or treatment of diseases and disorders associated with mitochondrial dysfunction.

In an embodiment, the diseases and disorders associated with mitochondrial dysfunction are primary mitochondrial diseases including but not limited to Leber's hereditary optic neuropathy (LHON), dominant optic neuropathy (DOA), Leigh syndrome, Friedreich's ataxia, mitochondrial myopathy, encephalomyopathy, lactic acidosis, stroke-like symptoms (MELAS), myoclonic epilepsy with ragged red fibers (MERRF), myoneurogenic gastrointestinal encephalomyopathy (MNGIE), Kearns-Sayre syndrome, CoQ.10 deficiency, or mitochondrial complex deficiencies, neuropathy, ataxia, retinitis pigmentosa, and ptosis (NARP).

In an embodiment, the diseases and disorders associated with mitochondrial dysfunction are neurodegenerative or neuromuscular diseases associated with mitochondrial dysfunction including but not limited to spinocerebellar ataxias, ataxia telangiectasia, ataxia oculomotor apraxia 1 and 2 (AOA1 and 2), epileptic seizures, amyotrophic lateral sclerosis (ALS), motor neuron disease (MND), Parkinson's disease, Alzheimer's disease, Huntington's disease, stroke/reperfusion injury, or dementia, Duchenne muscular dystrophy (DMD), Becker muscular dystrophy (BMD), Limb-Girdle muscular dystrophy (LGMD), X-linked dilated cardiomyopathy (XLDCM), pantothenate kinase-associated neurodegeneration (PKAN,), spinal muscular atrophy (SMA), multiple sclerosis and primary progressive multiple sclerosis (PP-MS), Kugelberg-Welander disease, and Werdnig-Hoffmann disease, diabetes mellitus and deafness (DAD).

In an embodiment, the diseases and disorders associated with mitochondrial dysfunction are metabolic disorders associated with mitochondrial dysfunction including but not limited to Wolfram syndrome, non-alcoholic liver disease (i.e. NAFLD, NASH, cirrhosis), ageing-related physical decline, obesity, overweight, diabetes mellitus, type II diabetes, diabetic retinopathy, and metabolic syndrome.

In an embodiment, the diseases and disorders associated with mitochondrial dysfunction are psychiatric disorder associated with mitochondrial dysfunction including but not limited to schizophrenia, major depressive disorder, bipolar disorder, epilepsy, post-traumatic stress disorder (PTSD), and circadian rhythm disorders.

In an embodiment, the diseases and disorders associated with mitochondrial dysfunction are inflammatory disorders associated with mitochondrial dysfunction including but not limited to Ulcerative colitis (UC), Crohn's disease (CD), arthritis, psoriasis or rheumatoid arthritis, migraine, dry eye syndrome, uveitis, allergic conjunctivitis, post-operative inflammation and acute kidney injury. In an embodiment, the disease or disorder associated with mitochondrial dysfunction is the effects of aging. Hence, the compounds described herein are proposed to have an anti-aging effect by ameliorating mitochondrial dysfunction.

In an embodiment, the disease and disorder is caused by drug-induced or environmental-induced mitochondrial dysfunction. For example, factors having a negative effect on mitochondrial activity or function include drug- or environment-induced mitochondrial dysfunction resulting from an antiviral; an anti-cancer agent; an antibiotic; a CNS drug; a hypertension drug; an anthracyclines; a non-steroidal anti-inflammatory drug (NSAID); an anestetic; a beta-blocker; an anti-arrhythmic; an anti-diabetic; an anti-inflammatory; or another agent.

Examples of antivirals having a negative effect on mitochondrial activity or function include abacavir, didanosine, emtricitabine, entecavir, emtricitabine, lamivudine, nevirapine, telbivudine, tenofovir, tipranavir, stavudine, zalcitabine, and zidovudine. Examples of anti-cancer agents having a negative effect on mitochondrial activity or function include arsenic trioxide, cetuximab, dacarbazine, denileukin, diftitox, flutamide, gemtuzumab, methotrexate, mitoxantrone, pentostatin, and tamoxifen. Examples of antibiotics having a negative effect on mitochondrial activity or function include antimycin A, isoniazid, chloramphenicol, ethambutol, gentamycin, ketoconazole, linezolid, streptozocin, streptomycin, tobramycin, tetracyclines, and trovafloxacin. Examples of CNS drugs having a negative effect on mitochondrial activity or function include amitriptyline, amphetamines, atomoxetin, chlorpromazine, cocaine, dantrolene, desipramine, divalproex, droperidol, felbamate, fluphenazine, imipramine, methamphetamine, naltrexone, nefazodone, pergolide, and valproic acid. Examples of hypertension drugs having a negative effect on mitochondrial activity or function include bosentan. Examples of anthracyclines having a negative effect on mitochondrial activity or function include daunorubicin, doxorubicin, epirubicin, and idarubicin. Examples of non-steroidal anti-inflammatory drugs (NSAIDs) having a negative effect on mitochondrial activity or function include aspirin, celecoxib, diclofenac, diflunisal, etodolac, fenoprofen, ibuprofen, indomethacin, ketoprofen, mefenamic acid, meloxicam, naproxen, nabumetone, oxaprozin, piroxicam, salsalate, sulindac, thioridazine, and tolmetin. Examples of anestetics having a negative effect on mitochondrial activity or function include bupivacaine and isoflurane. Examples of beta-blockers having a negative effect on mitochondrial activity or function include atenolol. Example of anti-arrhythmics having a negative effect on mitochondrial activity or function include amiodarone, disopyramide, dofetilide, and ibutilide. Examples of anti-diabetics having a negative effect on mitochondrial activity or function include pioglitazone and rosiglitazone. Examples of anti-inflammatory agents having a negative effect on mitochondrial activity or function include prednisolone, dexamethasone, hydrocortisone, and triamcilone. Examples of other agents having a negative effect on mitochondrial activity or function include clioquinol, cyanide, hexachlorophene, rotenone, and statins.

In an embodiment, the mammal is a human.

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself. This also applies to amelioration of the effects of aging to reduce the immediate impact of aging.

The terms "administer", "administering" or "administration" in reference to a compound, composition or formulation of either Formula (I), Formula (Ia) or Formula (Ib) or embodiments mentioned hereinbefore, means introducing the compound into the system of the animal in need of treatment. When a compound of the subject invention is provided in combination with one or more other active agents, "administration" and its variants are each understood to include concurrent and/or sequential introduction of the compound and the other active agents.

The compounds of either Formula (I), Formula (Ia) or Formula (Ib) or embodiments mentioned hereinbefore can also be used in research applications, such as in vitro, in vivo, or ex vivo experiments in order to modulate one or more biomarkers in an experimental system. Such experimental systems can be cell samples, tissue samples, cell components or mixtures of cell components, partial organs, whole organs, or organisms. Such research applications can include, but are not limited to, use as assay reagents, elucidation of biochemical pathways, or evaluation of the effects of other agents on the metabolic state of the experimental system in the presence/absence of one or more compounds of the subject invention.

Additionally, the compounds of Formula (I), Formula (Ia) and Formula (Ib) or embodiments mentioned hereinbefore can be used in biochemical tests or assays. Such tests can include incubation of one or more compounds of Formula (I), Formula (Ia) and Formula (Ib) or embodiments mentioned hereinbefore with a tissue or cell sample from a subject to evaluate a subject's potential response (or the response of a specific subset of subjects) to administration of said one or more compounds, or to determine which compound of Formula (I) or Formula (Ia) or embodiments mentioned hereinbefore produces the optimum effect in a specific subject or subset of subjects. Accordingly, enabled herein is an assay or screen for identifying a compound of Formula (I), Formula (Ia) and Formula (Ib) or an embodiment mentioned hereinbefore that modulates the activity of one or more biomarkers, the assay comprising the steps of i) obtaining a cell sample or tissue sample from a subject or set of subjects in which modulation of one or more biomarkers can be assayed; ii) administering one or more compounds of the subject invention to the cell sample(s) or tissue sample(s); and 3) quantifying the effect of the compounds on the modulation of the one or more biomarkers after administration of the one or more compounds, compared to the status of the biomarker prior to administration of the one or more compounds.

Further enabled herein is an assay or screen for identifying a compound of Formula (I), Formula (Ia) and Formula (Ib) or an embodiment mentioned hereinbefore that modulates the activity of one or more biomarkers, the assay comprising the steps of i) obtaining a cell sample or tissue sample from a subject or set of subjects in which modulation of one or more biomarkers can be assayed; ii) administering at least two compounds of the subject invention to the cell sample(s) or tissue sample(s); iii) quantifying the effect of the compounds on the modulation of the one or more biomarkers after administration of the at least two compounds, compared to the status of the biomarker prior to administration of the at least two compounds, and iv) selecting a compound for use in treatment, suppression, or modulation based on the amount of modulation determined in step iii).

In an embodiment, the biomarker is a chemokine, cytokine, growth factor or chemotactic agent. In the method of identifying a compound of Formula (I), Formula (Ia) and Formula (Ib) or an embodiment mentioned hereinbefore which modulates the activity of one or more biomarkers, the compounds may be selected on the basis of one or more physicochemical, pharmacokinetic, biological, and/or physiological properties. Examples of such properties include, but are not limited to, binding affinity, selectivity, toxicity, efficacy, stability, lipophilicity, and/or activity, such as agonism, antagonism and/or inhibition.

The interaction with a biomarker may be detected by any convenient means such as nuclear magnetic resonance (NMR), mass spectrometry (MS), isothermal titration calorimetry (ITC), dynamic light scattering (DLS), surface plasmon resonance (SPR), dual polarization interferometry (DPI), microscale thermophoresis (MST), gel retardation, filter retardation, affinity co-electrophoresis, bioluminescent resonance energy transfer (BRET) assays, fluoresence resonance energy transfer (FRET) assays, fluorescence polarization (FP) assays, scintillation proximity assays or immobilization to biochips or other surfaces including those coupled with mass spectrometric detection.

The latter may be accomplished by first immobilizing a compound to a chip and then adding a sample. Alternatively, a given biomarker may be immobilized to a chip and used to screen for the ability of a compound to bind thereto.

There are, of course, any number of other assays, which may be used to screen for interaction between a compound of Formula (I), Formula (Ia) or Formula (Ib) and biomarker. Another assay is a filter binding assay. In this assay, one of a compound, or a biomarker is labeled with a reporter molecule capable of providing an identifiable signal such as a fluorescent dye and both molecules are allowed to interact in solution. The resulting mixture is then passed through a filter capable of retarding one of components, such as the compound or the biomarker.

Different compounds will interact with different biological regulators, or different regulators will interact with different compounds or both. In addition, different compounds may interact with different biological regulator receptor chains. Accordingly, another assay involves the use of affinity columns carrying immobilized chemokines. The compounds are then passed through the column and the presence of retardation of the compounds determined. A salt gradient is conveniently used to elute bound compounds.

Other examples of assays contemplated by the present invention include functional assays such as whole cell assays. Such functional assays may provide more useful information on the effect of the tested compound than binding assays.

As used herein the expression "pharmaceutically acceptable salt" refers to the salt of a given compound, wherein the salt is suitable for administration as a pharmaceutical. For example, such salts may be formed by the reaction of an acid or a base with an amino or a carboxyl group respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "protecting group" refers to any group which when bound to one or more hydroxyl, thiol, amino or carboxyl groups of the compounds prevents reactions from occurring at these groups and which protecting group can be removed by conventional chemical or enzymatic steps to re-establish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in Greene and Wuts (1991), "Protective Groups in Organic Synthesis" 2$^{nd}$ Ed, John Wiley and Sons, N.Y.

Examples of removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Examples of removable alcohol blocking groups include conventional substituents such as ethers, including methyl ethers, t-butyl ether, silyl ethers; methoxymethyl ether (MOM), allyl ether, benzyl ethers, and esters such as acetic acid esters (AcO—) and benzoic acid esters, which can be removed by conventional conditions compatible with the nature of the product.

Examples of removable carbonyl or acid blocking groups include conventional substituents such as esters, including methyl ester, t-butyl ester, benzyl esters, which can be removed by conventional conditions compatible with the nature of the product.

"Selectivity" or "specificity" in general is a measure of the binding preferences of a ligand for different receptors and/or a measure of the binding preferences of different ligands for a receptor. The selectivity of a ligand with respect to its target receptor relative to another receptor is given by the ratio of the respective values of Kd (i.e., the dissociation constants for each ligand-receptor complex), or in cases where a biological effect is observed below the Kd, selectivity is given by the ratio of the respective EC50 values (i.e. the concentrations that produce 50% of the maximum response for the ligand interacting with the two distinct receptors).

EXAMPLES

General Synthetic Schemes and Description

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), diethyl ether (Et$_2$O), ethyl acetate (EtOAc), triethylamine (TEA), dichloromethane (methylene chloride, DCM), trifluoroacetic acid (TFA), trifluoroethanol (TFE), dimethylformamide (DMF), sodium sulphate (Na$_2$SO$_4$), tetrahydrofuran (THF), meta-chloroperoxybenzoic acid (mCPBA), hexamethyldisilazane sodium salt (NaHMDS), O-(7-azabenzotriazol-1-yl)-N,N,N',N'-tetramethyluronium hexafluorophosphate (HATU), dimethylsulfoxide (DMSO), magnesium sulphate (MgSO$_4$), sodium hydrogen carbonate (NaHCO$_3$), tert-butanol (t-BuOH), 1-ethyl-3-(3-dimethylaminopropyl) carbodiimide hydrochloride salt (EDCl.HCl), tetra-n-butylammonium fluoride (TBAF), tetra-n-butylammonium bromide (TBAB), N,N-diisopropylethylamine (DIPEA), tert-butyldimethylsilyl (TBDMS), 1-hydroxybenzotriazole (HOBt), trans-dichlorobis(triphenylphosphine)palladium(II) (PdCl$_2$(PPh$_3$)$_2$), tetrakis(triphenylphosphine)palladium(0) (Pd(PPh$_3$)$_4$) tris (dibenzylideneacetone) dipalladium(0) (Pd$_2$(dba)$_3$), tri-t-butyl phosphonium tetrafluoroborate (t-Bu$_3$PH.BF$_4$), 4,5-bis (diphenylphosphino)-9,9-dimethylxanthene (Xantphos), triphenylphosphine (PPh$_3$), diisopropyl azodicarboxylate (DIAD), pyridinium chlorochromate (PCC), borane dimethylsulfide (BMS), titanium isopropoxide (TiOiPr$_4$), sodium triacetoxyborohydride (NaBH(OAc)$_3$), sodium cyanoborohydride (NaBH$_3$(CN)), sodium borohydride (NaBH$_4$), ammonium chloride (NH$_4$Cl), chloroform (CHCl$_3$), manganese dioxide (MnO$_2$), potassium carbonate (K$_2$CO$_3$), 1,2-dichloroethane (DCE), sodium azide (NaN$_3$), sodium nitrite (NaNO$_2$) and di-tert-butyl dicarbonate (Boc$_2$O).

General Procedure A: Quinone Acid Synthesis;
Silver Mediated Radical Decarboxylation

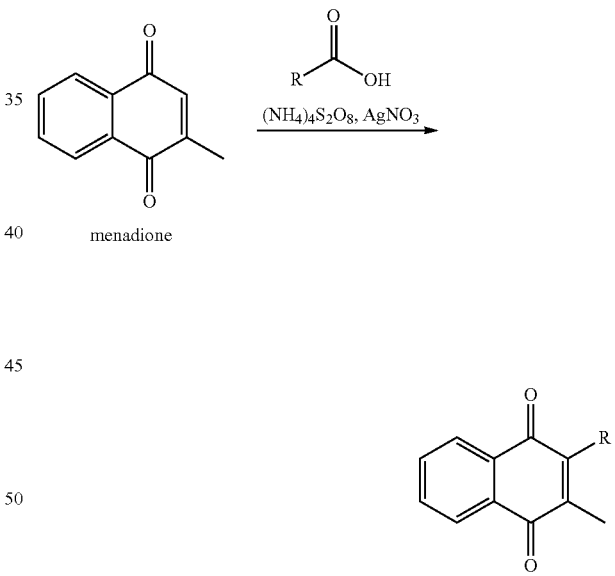

Carboxylic acid (2 equiv.) was added to a solution of menadione (1 equiv.) in CH$_3$CN/H$_2$O (3:1) and the mixture was heated to 75° C. To this solution, AgNO$_3$ (0.1 equiv.) was added followed by the slow addition of (NH$_4$)$_2$S$_2$O$_8$(2.5 equiv.) in H$_2$O (5 mL) over 10 mins. The resulting mixture was stirred for a further 2 h. The mixture was cooled to room temperature, extracted with dichloromethane and the organic extract washed with H$_2$O. The organic layer was dried over MgSO$_4$, filtered and the solvent removed under reduced pressure to give the crude product, which was purified by flash chromatography (silica gel).

General Procedure B: Quinone Amide Coupling

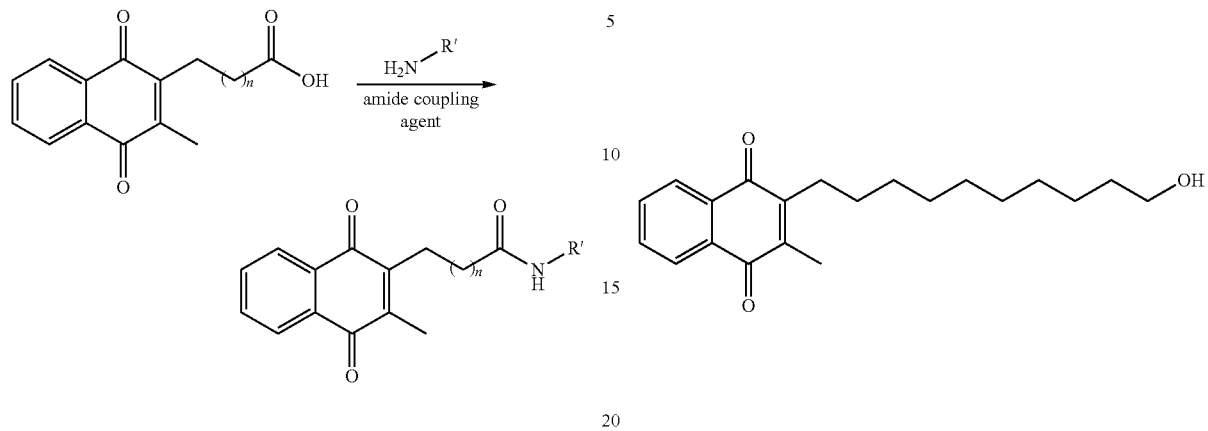

Quinone acid (1 equiv.) was added to anhydrous dichloromethane (5-10 ml) under an atmosphere of $N_2$ and cooled to 0° C. Amine (1 equiv.), dimethylaminopyridine (DMAP, 0.1 equiv.), triethylamine ($Et_3N$, 2.5 equiv.) and a coupling agent (1.4 equiv.) were added consecutively and the reaction mixture warmed slowly to room temperature before leaving overnight. The reaction was quenched with $H_2O$ (20 mL) and the organic layer washed with sat. $KHSO_4$ solution, sat. $NaHCO_3$ solution and $H_2O$. The organic layer was dried with $MgSO_4$, filtered and the solvent removed under reduced pressure to give a crude product, which was purified by flash chromatography (silica gel) to give the pure analogue.

General Procedure C: t-Butyl Ester Deprotection Method

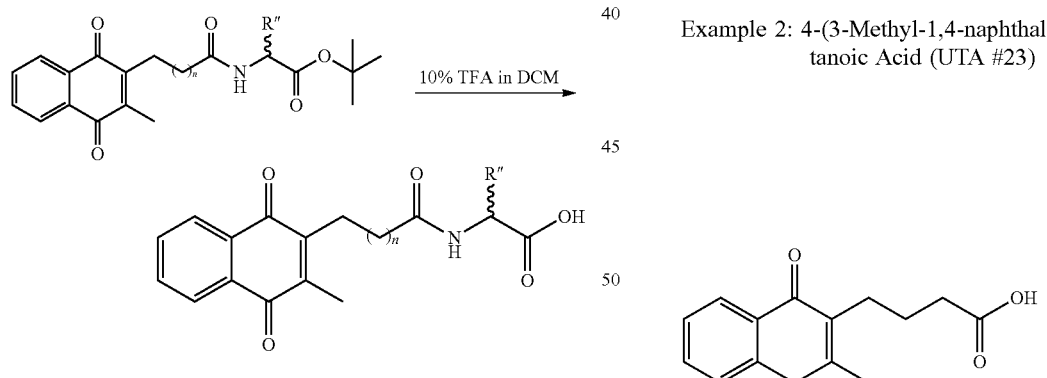

The t-butyl esters were added to 10% TFA in dichloromethane (5.0 mL) and the reaction mixture stirred at room temperature over night before the solvent was removed under reduced pressure. The crude product was obtained and purified by flash chromatography (silica gel) to give the pure analogue.

Representative Examples

Representative examples of compounds of Formula (I) were generated as described under General Procedures A, B and/or C.

Example 1: 2-(10-Hydroxydecyl)-3 methyl-1,4-naphthoquinone (UTA #2)

UTA #2 was prepared according to general procedure A from menadione (201 mg, 1.17 mmol) and 11-hydroxyundecanoic acid (467 mg, 2.30 mmol) and the product purified by flash chromatography (40% ethyl acetate/hexanes) to give UTA #2 as a pale yellow solid in 19% yield (168 mg, 0.511 mmol) with a melting point of 74-75° C.

$^1$H NMR δ ($CDCl_3$, 300 MHz): 1.24-1.57 (m, 16H), 2.17 (s, 3H), 2.61 (t, J=7.0 Hz, 2H), 3.62 (t, J=6.6 Hz, 2H), 7.65-7.69 (m, 2H), 8.04-8.07 (m, 2H); $^{13}$C NMR δ ($CDCl_3$, 75 MHz): 12.8, 25.8, 27.2, 28.9, 29.5, 29.6, 29.7, 30.1, 32.9, 63.2, 126.3, 126.4 132.3, 132.4, 133.4, 133.5, 143.3, 147.7, 184.9, 185.5 (one carbon overlapping); HRMS: For $C_{21}H_{28}O_3$, predicted 328.20384, found 328.20383; MS m/z (EI+): 328 (M+, 62), 310 (5), 211 (10), 187 (100), 174 (12) 158 (18); IR $V_{max}$: 3525, 2917, 2848, 1658, 1618, 1593, 1459, 1738, 1327, 1297, 717

Example 2: 4-(3-Methyl-1,4-naphthalen-2-yl)-butanoic Acid (UTA #23)

UTA #23 was prepared according to general procedure A from menadione (1.953 g, 11.34 mmol) and glutaric acid (3.041 g, 23.01 mmol) and purified by flash chromatography (silica gel, 100% $CH_2Cl_2$ followed by 100% ethyl acetate) to give UTA #23 as a yellow solid in 40% yield (1.169 g, 4.525 mmol) with a melting point of 74-78° C.

$^1$H NMR δ (CDCl$_3$, 400 MHz): 1.82 (quin, J=7.6 Hz, 2H), 2.20 (s, 3H), 2.46 (t, J=7.2 Hz, 2H), 2.69 (t, J=7.9 Hz, 2H), 7.66-7.69 (m, 2H), 8.04-8.06 (m, 2H); $^{13}$C NMR δ (CDCl$_3$, 100 MHz): 12.84, 23.57, 26.41, 33.89, 126.43, 126.50, 132.24, 132.28, 133.61, 133.62, 144.15, 146.27, 179.39, 184.77, 185.36; IR V$_{max}$: 3064, 2938, 2359, 2340, 1706, 1699, 1695, 1658, 1616, 1595, 1412, 1379, 1325, 1295, 1260, 717, 692, 66 Example 3: 25-(3-methyl-1,4-naphthoquinone-2-yl)pentanoic acid (UTA #67)

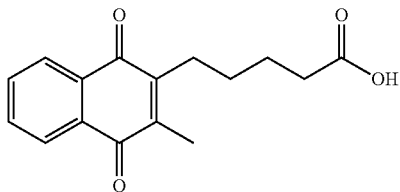 [SMILES: CC1=C(CCCCC(=O)O)C(=O)c2ccccc2C1=O]

UTA #67 was prepared according to general procedure A from menadione (2.1636 g, 12.566 mmol) and adipic acid (3.7242 g, 25.484 mmol) and the product purified by flash chromatography (100% dichloromethane followed by 100% ethyl acetate) to give UTA #67 as a crystalline yellow solid in 78% yield (2.6528 g, 9.7422 mmol) with a melting point of 66-70° C.

$^1$H NMR δ (CDCl$_3$, 400 MHz): 1.49-1.57 (m, 2H), 1.70-1.77 (m, 2H), 2.17 (s, 3H), 2.40 (t, J=7.4 Hz, 2H), 2.64 (t, J=7.9 Hz, 2H), 7.66-7.68 (m, 2H), 8.03-8.05 (m, 2H); $^{13}$C NMR δ (CDCl$_3$, 100 MHz): 12.7, 24.9, 26.7, 28.1, 33.8, 126.3, 126.4, 132.20, 132.21, 133.4, 133.5, 143.5, 146.8, 179.6, 184.7, 185.3; IR V$_{max}$: 2939, 1705, 1658, 1618, 1595, 1379, 1327, 1294, 1261, 715

Example 4: 4-(1,4-naphthoquinone-2-yl)butanoic Acid (UTA #59)

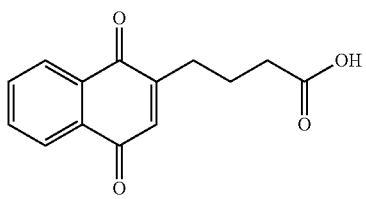 [SMILES: O=C(O)CCCC1=CC(=O)c2ccccc2C1=O]

UTA #59 was prepared according to general procedure A from naphthoquinone (1.9989 g, 12.64 mmol) and glutaric acid (0.8354 mg, 6.323 mmol) and the product purified by a Reveleris (Registered Trade Mark) X2 automated flash chromatography system (Eluent: gradient 0-80% ethyl acetate in hexane, Column: Reveleris (Registered Trade Mark) Silica 24 g, Flow rate: 18 mL/min) to give UTA #59 as a brown solid in 42% yield (0.6546 g, 2.680 mmol) with a melting point of 120-122° C.

$^1$H NMR δ (CD$_3$OD, 400 MHz): 1.90 (quin, J=7.6 Hz, 2H), 2.39 (t, J=7.2 Hz, 2H), 2.62 (td, J=7.6, 1.1 Hz, 2H), 6.85 (t, J=1.2 Hz, 1H), 7.78-7.80 (m, 2H), 8.02-8.04 (m, 1H), 8.07-8.10 (m, 1H); $^{13}$C NMR δ (CD$_3$OD, 100 MHz): 24.4, 30.0, 34.3, 126.8, 127.4, 133.4, 133.7, 134.8, 134.9, 136.0, 152.4, 186.1, 186.3 (one carbon missing or overlapped); IR V$_{max}$: 2956, 1699, 1660, 1620, 1953, 1417, 1327, 1303, 1265, 1143, 783, 661

Example 5: (R)-methyl-2(4-(3-methyl-1,4-naphthoquinone-2-yl)butamido)-3-phenylpropanoate (UTA #35)

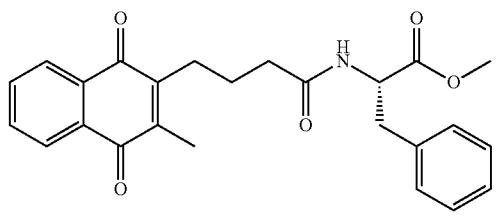 [SMILES: COC(=O)[C@H](Cc1ccccc1)NC(=O)CCCC1=C(C)C(=O)c2ccccc2C1=O]

UTA #35 was prepared according to general procedure B from UTA #23 (107.7 mg, 0.4170 mmol) and (R)-phenylalanine methyl ester (90.4 mg, 0.4193 mmol). The product purified by a Reveleris (Registered Trade Mark) X2 automated flash chromatography system (Eluent: gradient 100% Hexanes—100% ethyl acetate, Column: Reveleris (Registered Trade Mark) Silica 4 g, Flow rate: 18 mL/min) to give UTA #35 as a yellow oil in 29% yield (51.3 mg, 0.1223 mmol).

$^1$H NMR δ (CDCl$_3$, 400 MHz): 1.80 (quin, J=8.2 Hz, 2H), 2.20 (s, 3H), 2.29 (t, J=7.2 Hz, 2H), 2.65 (t, J=7.9 Hz, 2H), 3.15 (qd, J=14.0, 6.0 Hz, 2H), 3.74 (s, 3H), 6.11 (d, J=7.8 Hz, 1H), 4.92 (q, J=6.1 Hz, 1H), 7.12-7.14 (m, 2H), 7.24-7.31 (m, 3H), 7.70-7.72 (m, 2H), 8.07-8.10 (m, 2H); $^{13}$C NMR δ (CDCl$_3$, 100 MHz): 12.9, 24.3, 26.4, 23.9, 38.1, 52.5, 53.2, 126.4, 126.5, 127.3 128.7 (two carbons), 129.4 (two carbons), 132.2, 132.3, 133.5, 133.6, 136.1, 144.2, 146.4, 172.0, 172.3, 184.9, 185.3; HRMS: For C$_{25}$H$_{25}$N$_1$O$_5$, predicted 419.17327, found 419.17403; MS m/z (EI+): 419 (M+, 45), 241 (100), 197 (50), 162 (100), 120 (45); IR V$_{max}$: 3371, 3293, 2951, 1745, 1652, 1596, 1538, 1436, 1378, 1329, 1295, 1215, 717

Example 6: (S)-tert-butyl-2-(4-(3-methyl-1,4-naphthoquinone-2-yl)butanamido)-3-phenylpropanoate (UTA #36)

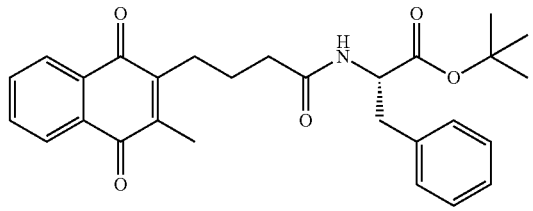 [SMILES: CC1=C(CCCC(=O)N[C@@H](Cc2ccccc2)C(=O)OC(C)(C)C)C(=O)c2ccccc2C1=O]

UTA #36 was prepared according to general procedure B from UTA #23 (504.2 mg, 1.9522 mmol) and L-phenylalanine t-butyl ester.HCl (489.4 mg, 1.9023 mmol) and the product purified by flash chromatography (40% ethyl acetate/hexanes) to give UTA #36 as a yellow oil in 36% yield (317.3 mg, 0.6875 mmol).

$^1$H NMR δ (CDCl$_3$, 400 MHz): 1.40 (s, 9H), 1.78 (quin, J=7.8 Hz, 2H), 2.17 (s, 3H), 2.27 (t, J=7.4 Hz, 2H), 2.62 (t, J=8.0 Hz, 2H), 3.04-3.13 (m, 2H), 4.77 (q, J=6.2 Hz, 1H), 6.09 (d, J=7.8 Hz, 1H), 7.14-7.27 (m, 5H), 7.66-7.69 (m, 2H), 8.04-8.07 (m, 2H)

$^{13}$C NMR δ (CDCl$_3$, 100 MHz): 12.8, 24.3, 26.3, 28.0 (three carbons), 36.1, 38.2, 53.5, 82.4, 126.3, 126.4, 127.0, 128.4 (two carbons), 129.5 (two carbons), 132.21, 132.26, 133.4, 133.5, 136.3, 144.0, 146.4, 170.9, 171.8, 184.8, 185.3; [α]$_D^{20}$: +36.2⁴(c 0.91, CHCl$_3$); IR V$_{max}$: 3420, 2978, 1732, 1658, 1595, 1525, 1367, 1329, 1294, 1257, 1226, 1155, 700

Example 7: (S)-tert-butyl-1-(4-(3-methyl-1,4-naphthoquinone-2-yl)butanoyl)pyrrolidine-2-carboxylate (UTA #42)

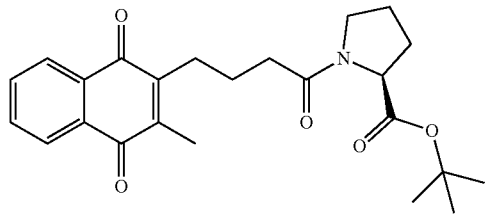 [SMILES: CC1=C(CCCC(=O)N2CCC[C@H]2C(=O)OC(C)(C)C)C(=O)c2ccccc2C1=O]

UTA #42 was prepared according to general procedure B from UTA #23 (196.9 mg, 0.7623 mmol) and L-proline t-butyl ester.HCl (139.5 mg, 0.6716 mmol) and the product purified by flash chromatography (60% ethyl acetate/hexanes) to give UTA #42 as yellow oil in 53% yield (145.8 mg, 0.3543 mmol).

$^1$H NMR δ (CDCl$_3$, 400 MHz): 1.44 (s, 9H), 1.82-1.88 (m, 2H), 1.90-1.96 (m, 2H), 2.04-2.13 (m, 2H), 2.21 (s, 3H), 2.36-2.48 (m, 2H), 2.67-2.71 (m, 2H), 3.47-3.52 (m, 1H), 3.59-3.64 (m, 1H), 4.37 (dd, J=8.5, 3.9 Hz, 1H), 7.66-7.68 (m, 2H), 8.03-8.07 (m, 2H); $^{13}$C NMR δ (CDCl$_3$, 100 MHz): 12.8, 23.7, 24.7, 26.5, 28.0 (three carbons), 29.3, 34.1, 47.1, 59.5, 81.2, 126.2 (two carbons), 132.23, 132.26, 133.3 (two carbons), 144.0, 146.7, 171.0, 171.6, 184.7, 185.3; [α]$_D^{20}$: +48.70° (c 0.97, CHCl$_3$); IR V$_{max}$: 2976, 2935, 1735, 1654, 1618, 1595, 1456, 1425, 1367, 1294, 1153, 719

Example 8: N-(2-(1H-indol-3-yl)ethyl)-4-(3-methyl-1,4-naphthoquinone-2-yl)butanamide (UTA #73)

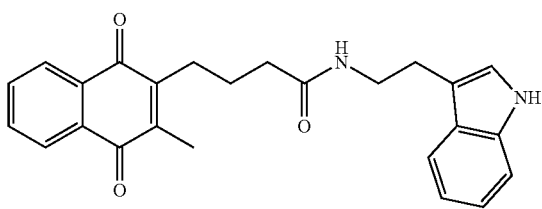 [SMILES: CC1=C(CCCC(=O)NCCc2c[nH]c3ccccc23)C(=O)c2ccccc2C1=O]

UTA #73 was prepared according to general procedure B from UTA #23 (193.9 mg, 0.7507 mmol) and tryptamine (123.5 mg, 0.7708 mmol) and the product purified by flash chromatography (80% ethyl acetate/hexanes) to give UTA #73 as a brown viscous oil in 42% yield (127.3 mg, 0.3178 mmol).

$^1$H NMR δ (CDCl$_3$, 400 MHz): 1.77 (quin, J=7.6 Hz, 2H), 2.14 (s, 3H), 2.22 (t, J=7.3 Hz, 2H), 2.59 (t, J=7.9 Hz, 2H), 2.97 (t, J=6.8 Hz, 2H), 3.61 (q, J=6.2 Hz, 2H), 6.13 (t, J=5.2 Hz, 1H), 7.01 (bs, 1H), 7.04-7.08 (m, 1H), 7.11-7.15 (m, 1H), 7.32 (d, J=8.1 Hz, 1H), 7.56 (d, J=7.9 Hz, 1H), 7.64-7.67 (m, 2H), 7.99-8.04 (m, 2H), 8.69 (bs, 1H); $^{13}$C NMR δ (CDCl$_3$, 100 MHz): 12.7, 24.3, 25.2, 26.3, 36.1, 39.9, 111.4, 112.7, 118.6, 119.3, 122.0, 122.2, 126.2 (two carbons), 127.3, 132.02, 132.09, 133.42, 133.47, 136.4, 143.9, 146.2, 172.6, 184.8, 185.1; IR V$_{max}$: 3392, 3294, 2935, 1705, 1653, 1595, 1527, 1458, 1332, 1296, 740, 715

Example 9: N-(4-hydroxyphenethyl)-4-(3-methyl-1,4-naphthoquinone-2-yl)butanamide (UTA #74)

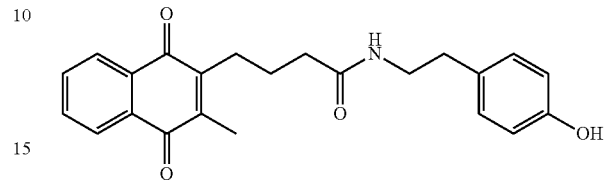

UTA #74 was prepared according to general procedure B from UTA #23 (235.6 mg, 0.9122 mmol) and tyramine (119.0 mg, 0.8675 mmol) and the product purified by flash chromatography (80% ethyl acetate/hexanes) to give UTA #74 as yellow solid in 33% yield (108.9 mg, 0.2885 mmol) with a melting point of 116-118° C.

$^1$H NMR δ (CDCl$_3$, 400 MHz): 1.76 (quin, J=7.5 Hz, 2H), 2.12 (s, 3H), 2.24 (t, J=7.2 Hz, 2H), 2.56-2.60 (m, 2H), 2.71 (t, J=7.0 Hz, 2H), 3.47 (q, J=6.4 Hz, 2H), 6.22 (t, J=5.5 Hz, 1H), 6.75 (d, J=8.4 Hz, 2H), 6.96 (d, J=8.4 Hz, 2H), 7.62-7.65 (m, 2H), 7.97-8.00 (m, 2H); $^{13}$C NMR δ (CDCl$_3$, 100 MHz): 12.7, 24.4, 16.3, 34.7, 36.1, 41.1, 115.7 (two carbons), 126.3 (two carbons), 129.8 (two carbons), 129.9, 132.0, 132.1, 133.53, 133.59, 144.2, 146.2, 155.3, 173.1, 185.0, 185.2; IR V$_{max}$: 3365, 3306, 2935, 1654, 1616, 1595, 1541, 1516, 1375, 1330, 1296, 715

Example 10: N-(3,4-dimethoxyphenethyl)-4-(3-methyl-1,4-naphthoquinone-2-yl)butanamide (UTA #77)

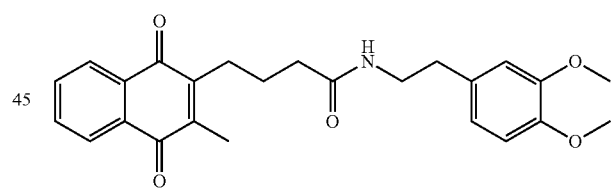

UTA #77 was prepared according to general procedure B from UTA #23 (187.5 mg, 0.7260 mmol) and 3,4-dimethoxyphenylethylamine (146.6 mg, 0.8088 mmol) and the product purified by flash chromatography (90% ethyl acetate/hexanes) to give UTA #77 as pale orange crystalline solid in 38% yield (117.0 mg, 0.2776 mmol) with a melting point of 105-108° C.

$^1$H NMR δ (CDCl$_3$, 400 MHz): 1.77 (quin, J=7.7 Hz, 2H), 2.16 (S, 3H), 2.22 (t, J=7.2 Hz, 2H), 2.60 (t, J=8.0 Hz, 2H), 2.74 (t, J=7.2 Hz, 2H), 3.48 (q, J=6.5 Hz, 2H), 3.79 (s, 3H), 3.81 (s, 3H), 5.94 (t, J=5.6 Hz, 1H), 6.68-6.76 (m, 3H), 7.63-7.66 (m, 2H), 7.98-8.02 (m, 2H); $^{13}$C NMR δ (CDCl$_3$, 100 MHz): 12.7, 24.3, 26.3, 35.2, 36.1, 40.7, 55.8, 55.9, 111.4, 111.9, 120.7, 126.25, 126.29, 131.4, 132.0, 132.1, 133.4, 133.5, 144.0, 146.2, 147.7, 149.0, 172.3, 184.8, 185.1.; IR V$_{max}$: 3377, 3296, 2935, 2656, 1595, 1516, 1462, 1329, 1294, 1261,1236, 1157, 1141, 1028, 717

Example 12: (S)—N-(1-hydroxy-3-phenylpropan-2-yl)-4-(3-methyl-1,4-naphthyoquinone-2-yl)butanamide (UTA #62)

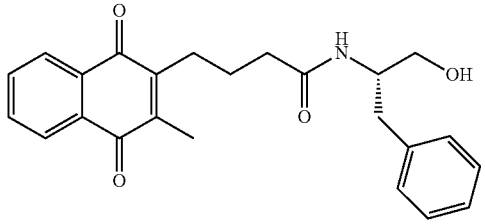 [SMILES: CC1=C(CCCC(=O)N[C@H](CO)Cc2ccccc2)C(=O)c2ccccc2C1=O]

UTA #62 was prepared according to general procedure B from UTA #23 (133.5 mg, 5169 mmol) and L-phenylalaninol (76.4 mg, 0.5053 mmol) and the product purified by flash chromatography (100% ethyl acetate) to give UTA #62 as yellow/orange oil in 49% yield (97.7 mg, 0.2496 mmol).

$^1$H NMR δ (CDCl$_3$, 400 MHz): 1.70-1.78 (m, 2H), 2.15 (s, 3H), 2.25 (t, J=7.2 Hz, 2H), 2.55 (t, J=8.0 Hz, 2H), 2.83-2.94 (m, 2H), 3.03 (bs, 1H), 3.59 (dd, J=11.2, 5.4 Hz, 1H), 3.71 (dd, J=11.2, 3.8 Hz, 1H), 4.21-4.29 (m, 1H), 6.31 (d, J=8.0 Hz, 1H), 7.15-7.27 (m, 5H), 7.64-7.69 (m, 2H), 8.00-8.05 (m, 2H); $^{13}$C NMR δ (CDCl$_3$, 100 MHz): 12.7, 24.3, 26.2, 36.2, 37.0, 52.9, 64.1, 126.35, 126.36, 126.6, 128.6 (two carbons), 129.2 (two carbons), 132.0, 132.1, 133.5, 133.6, 137.9, 144.2, 146.2, 173.1, 185.12, 185.13; [α]$_D^{20}$: −21.33° (c 1.57, CHCl$_3$); IR V$_{max}$: 3369, 3296, 2933, 1658, 1595, 1539, 1456, 1377, 1330, 1296, 1043, 717, 702

Example 13: (S)-2-(4-(2-(hydroxymethyl)pyrrolidin-1-yl)-4-oxobutyl)-3-methyl-1,4-naphthoquinone (UTA #61)

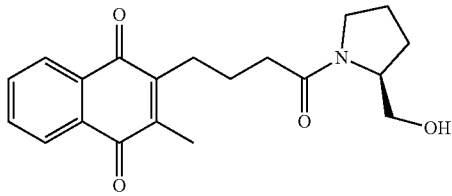 [SMILES: CC1=C(CCCC(=O)N2CCC[C@H]2CO)C(=O)c2ccccc2C1=O]

UTA #61 was prepared according to general procedure B from UTA #23 (116.8 mg, 0.4522 mmol) and L-prolinol (159.1 mg, 0.7587 mmol) and the product purified by flash chromatography (100% ethyl acetate) to give UTA #61 as yellow oil in 36% yield (49.8 mg, 1459 mmol).

$^1$H NMR δ (CDCl$_3$, 400 MHz): 1.60 (quin, J=6.2 Hz, 2H), 1.82-2.02 (m, 6H), 2.21 (s, 3H), 2.39 (t, J=7.2 Hz, 2H), 2.67-2.72 (m, 2H), 3.50-3.55 (m, 1H), 3.66 (dd, J=11.3, 2.8 Hz, 1H), 4.15-4.22 (m, 1H), 7.66-7.68 (m, 2H), 8.03-8.07 (m, 2H); $^{13}$C NMR δ (CDCl$_3$, 100 MHz): 12.8, 23.6, 24.5, 26.4, 28.3, 34.6, 48.1, 61.2, 67.3, 126.33, 126.37, 132.1, 132.2, 133.4, 133.5, 144.1, 146.6, 173.6, 184.9, 185.3; [α]$_D^{20}$: −35.12° (c 0.41, CHCl$_3$); IR V$_{max}$: 3367, 2953, 2877, 1695, 1654, 1616, 1595, 1454, 1329, 1296, 1047, 732, 719

Example 14: (S)-tert-butyl 2-(4-(1,4-naphthoquinone-2-yl)butanamido)-3-phenylpropanoate (UTA #116)

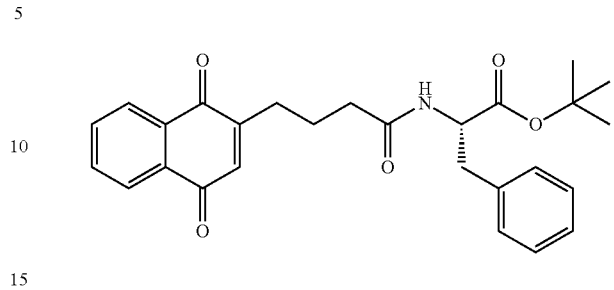

UTA #116 was prepared according to general procedure B from UTA #59 (29.5 mg, 0.1208 mmol) and L-phenyl alanine t-butyl ester.HCl (34.8 mg, 0.1353 mmol) and the product purified by a Reveleris (Registered Trade Mark) X2 automated flash chromatography system (Eluent: gradient 100% Hexanes—80% ethyl acetate, Column: Reveleris® Silica 4 g, Flow rate: 18 mL/min) to give UTA #116 as brown oil in 20% yield (10.9 mg, 0.0243 mmol).

$^1$H NMR δ (CDCl$_3$, 400 MHz): 1.43 (s, 9H), 1.91 (quin, J=7.6 Hz, 2H), 2.29 (td, J=7.5, 2.9 Hz, 2H), 2.56-2.60 (m, 2H), 3.10-3.14 (M, 2H), 4.76-4.81 (M, 1H), 6.03 (d, J=7.3 Hz, 1H), 7.16-6 7.31 (m, 5H), 7.74-7.76 (m, 2H), 8.07-8.12 (m, 2H); $^{13}$C NMR δ (CDCl$_3$, 100 MHz): 23.9, 28.1 (three carbons), 29.1, 35.8, 38.2, 53.5, 82.5, 126.2, 126.7, 127.1, 128.5 (two carbons), 129.6 (two carbons), 132.2, 132.3, 133.7, 133.8, 135.3, 136.3, 150.9, 170.9, 172.5, 185.1, 185.2; [c]$_D^{20}$: +38.46° (c 0.39, CHCl$_3$); IR V$_{max}$: 3309,2978, 2931, 1732, 1662, 1595, 1525, 1367, 1301, 1259, 1153, 700. UTA #116 may optionally be methylated at the 3 position (R5).

Example 15: (S)-2-(4-(3-methyl-1,4-naphthoquinone-2-yl)butanamido)-3-phenylpropanoic Acid (UTA #37)

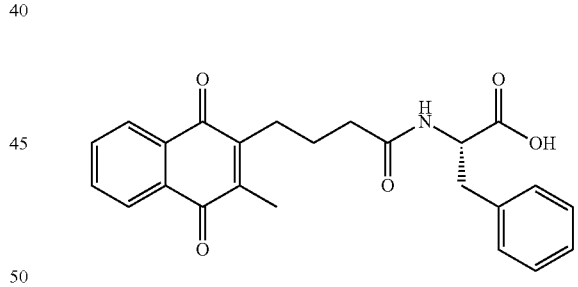

UTA #37 was prepared from the deprotection of UTA #36 (317.3 mg, 0.6875 mmol), using general procedure C. The product was purified by flash chromatography (5% methanol/ethyl acetate) to give UTA #37 as brown viscous oil in 79% yield (219.6 mg, 0.5416 mmol).

$^1$H NMR δ (CDCl$_3$, 400 MHz): 1.72-1.79 (m, 2H), 2.14 (s, 3H), 2.29 (t, J=7.2 Hz, 2H), 2.58 (t, J=7.8 Hz, 2H), 3.12 (dd, J=14.0, 7.0 Hz, 1H), 3.26 (dd, J=14.1, 5.4 Hz, 1H), 4.90 (m, 1H), 6.54 (d, J=7.7 Hz, 1H), 7.17-7.28 (m, 5H), 7.66-7.69 (m, 2H), 8.02-8.05 (m, 2H), 8.92 (bs, 1H); $^{13}$C NMR δ (CDCl$_3$, 100 MHz): 12.8, 24.2, 26.2, 35.8, 37.3, 53.4, 126.4 (two carbons), 127.2, 128.7 (two carbons), 129.4 (two carbons), 132.0, 132.2, 133.5, 133.6, 135.9, 144.3, 146.2, 173.5, 174.7, 185.1, 185.2; [α]$_D^{20}$: +35.83° (c 0.24, CHCl$_3$); IR V$_{max}$: 3491, 2931, 1716, 1660, 1616, 1595, 1521, 1456, 1332, 1296, 1267, 1217, 702

Example 16: (S)-1-(4-(3-methyl-1,4-naphthoquinone-2-yl)butanoyl)pyrrolidine-2-carboxylic Acid (UTA #43)

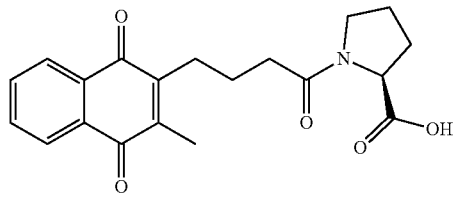 [SMILES: CC1=C(CCCC(=O)N2CCC[C@H]2C(=O)O)C(=O)c2ccccc2C1=O]

UTA #43 was prepared from the deprotection of UTA #42 (113.8 mg, 0.2766 mmol), using general procedure C. The product was purified by flash chromatography (3% methanol/ethyl acetate) to give UTA #43 as brown viscous oil in 65% yield (63.9 mg, 0.1798 mmol).

$^1$H NMR δ (CDCl$_3$, 400 MHz): 1.82-1.90 (m, 2H), 2.02-2.08 (m, 2H), 2.21 (s, 3H), 2.13-2.33 (m, 2H), 2.45-2/50 (m, 2H), 0.68-2.72 (m, 2H), 3.49-3.53 (m, 1H), 3.60-3.63 (m, 1H), 4.55-4.58 (m, 1H), 7.53 bs, 1H), 7.68-7.07 (m, 2H), 8.04-8.08 (m, 2H); $^{13}$C NMR δ (CDCl$_3$, 100 MHz): 12.8, 23.3, 24.8, 26.4, 28.0, 34.1, 47.8, 59.7, 126.34, 126.38, 132.1, 132.2, 133.51, 133.56, 144.2, 146.3, 173.4, 173.9, 184.8, 185.3; [α]$_D^{20}$: -65.80° (c 1.69, CHCl$_3$); IR V$_{max}$: 2976, 2956, 1732, 1658, 1616, 1595, 1456, 1329, 1294, 1188, 717

Example 17: 3-((3-methyl-1,4-naphthoquinone-2-yl)thio)propanoic Acid (UTA #46)

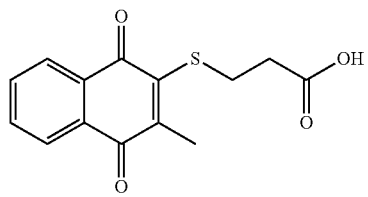 [SMILES: CC1=C(SCCC(=O)O)C(=O)c2ccccc2C1=O]

3-Mercaptopropanoic acid (1.4 mL, 10.829 mmol) was added to a solution of menadione (535.8 mg, 3.1119 mmol) in methanol (50 mL) and 2-propanol (40 mL) and the reaction mixture stirred at room temperature for 24 h. The solvent was removed under reduced pressure and re-dissolved in dichloromethane and washed with 10% copper sulfate solution (2×25 mL) and H$_2$O (3×25 mL) The organic layer was dried with MgSO$_4$, filtered and the solvent removed under reduced pressure to give a crude product which was purified by flash chromatography (30% ethyl acetate/hexanes) to give UTA #46 as a red solid oil in 48% yield (387.4 mg, 1.4021 mmol). Spectral data consistent with that reported in the literature [9]. 1H NMR δ (CDCl$_3$, 400 MHz): 2.34 (s, 3H), 2.75 (t, J=7.0 Hz, 2H), 3.42 (t, J=7.0 Hz, 2H), 7.69-7.71 (m, 2H), 8.06-8.09 (m, 2H); $^{13}$C NMR δ (CDCl$_3$, 100 MHz): 15.4, 28.9, 35.4, 126.7, 126.9, 132.1, 132.9, 133.5, 133.8, 145.8, 147.6, 176.2, 181.3, 182.2

Pharmacokinetic/Biological Examples

Example 18: Acute ATP Rescue Assay (Under Conditions of Impaired Mitochondrial Function)

Mitochondrial disorders are characterized by impaired mitochondrial function, which is usually displayed as lower mitochondrial synthesis of ATP. This energy crisis is seen as a major contributor for cellular impairment and ultimately cell death. Thus, improving the aberrant energy status that is associated with impaired mitochondrial function is necessary to normalize cellular and tissue function.

HepG2 cells were seeded at a density of 5000 cells per well in a 96-well plate and incubated for 24 hours in DMEM with 0.3 g/l glucose, 10% FBS and Penicillin-Streptomycin-Glutamine. Cells were treated with 1 μM quinones in presence or absence of rotenone (10 μM), for 60 minutes in glucose-free DMEM ATP levels were quantified using luminescence from the ATP-dependent enzymatic oxidation of luciferin by luciferase. Cells were lysed in a volume of 40 μl (4 mM EDTA, 0.2% Triton X-100) for five minutes at room temperature (RT) on an orbital shaker at 200 rpm. In 96-well plates, 100 μl of ATP measurement buffer (25 mM HEPES pH 7.25, 300 M D-luciferin, 5 μg/ml firefly luciferase, 75 μM DTT, 6.25 mM MgCL$_2$, 625 μM EDTA and 1 mg/ml BSA) was combined with 10 μl lysate to start the reaction. Luminescence was quantified immediately using a multimode plate reader (Fluoroscan Ascent, Thermo Scientific). ATP levels were standardized to protein levels using a commercial BCA assay (Protein DC; BioRad) and changes were calculated as percentage relative to levels of DMSO-treated control cells. Data is expressed as % ATP compared to the untreated (no-rotenone) control. The data represents the mean±S.D. of 3 independent experiments with 6 replicate wells (n=6) each.

The extent of ATP rescue of representative compounds of Formula (I) shown below in Table 4. Vitamin K, menadione and idebenone were used as comparative controls. DMSO was used as a control.

TABLE 4

| ATP Rescue Assay | |
|---|---|
| Cpd number (ie. UTA #) | ATP rescue [%] |
| Vehicle control (DMSO only) | 4.6 |
| Vitamin K | 3.5 |
| Menadione | 30.6 |
| idebenone | 81.0 |
| 55 | 94.8 |
| 62 | 91.2 |
| 65 | 91.1 |
| 67 | 97.1 |
| 70 | 91.8 |
| 71 | 92.2 |
| 72 | 84.8 |
| 73 | 96.1 |
| 74 | 100.7 |
| 75 | 95.4 |
| 77 | 99.1 |
| 84 | 90.4 |

Altered mitochondrial function, such as in mitochondrial disorders, may lead to depleted cellular ATP levels. As highlighted in Table 4, the representative compounds of Formula (I) significantly rescue ATP levels under conditions of impaired mitochondrial function, while the comparative compounds Vitamin K and Menadione exhibited no or minor effects.

Example 19: Rescue of Cell Viability in the Presence of a Mitochondrial Inhibitor Mitochondrial dysfunction, via the reduction of ATP production and an increased production of reactive oxygen species leads to significantly reduced cell survival. Thus, improved energy supply, as seen with the compounds of Formula (I) or Formula (Ia) or embodiments mentioned hereinbefore, should protect cell viability against mitochondrial dysfunction.

Cytoprotection of HepG2 cells by naphthoquinones was quantified in the presence of the mitochondrial toxin, rotenone. Briefly, HepG2 cells were seeded in 96-well plates at 5000 cells/well in in DMEM with 0.3 g/l glucose, 10% FBS and Penicillin-Streptomycin-Glutamine. After overnight incubation under standard conditions, cells were treated with the test compounds (10 µM) for 2 days before cells were challenged with 1 µM rotenone in the presence of 10 µM test compounds in Hank's balanced salt solution (HBSS) for 6 hours. This was followed by post-incubation for an additional 18 hours with only 10 µM test compounds in HBSS. For measurement of cell viability, cells were washed with 100 µL PBS twice and then lysed using 40 µL lysis solution (4 mM EDTA, 0.2% Triton X-100) for 5 min at room temperature (RT) on an orbital shaker at 200 rpm. Then 10 µL of the lysate was mixed with 90 µL of enzyme-substrate mixture (as described above) in a white 96 well plate and luminescence was measured immediately using a platereader (Fluoroscan Ascent, Thermo Scientific). The data is expressed as % viability compared to the untreated (no-rotenone) control. The data represents the mean±S.D. of 3 independent experiments with 6 replicate wells (n=6) each.

The extent of protection of cellular viability against a rotenone challenge of representative compounds of Formula (I) is shown below in Table 5. Vitamin K, Menadione and Idebenone were used as comparative controls. DMSO was used as a control.

TABLE 5

Cell Viability Assay

| Compound number | Viability [%] |
|---|---|
| Vehicle control (DMSO only) | 6.6 |
| Vitamin K | 14.5 |
| Menadione | 64.0 |
| Idebenone | 66.2 |
| 37 | 100.3 |
| 43 | 92.7 |
| 46 | 80.5 |
| 54 | 98.7 |
| 61 | 100.7 |
| 62 | 93.1 |
| 72 | 90.7 |
| 73 | 86.2 |
| 74 | 91.7 |
| 77 | 95.9 |
| 80 | 87.6 |
| 81 | 83.8 |
| 88 | 91.8 |
| 89 | 85.2 |
| 91 | 82 |
| 95 | 86.1 |
| 97 | 84.8 |
| 115 | 80.8 |
| 117 | 80.3 |

As highlighted in Table 5, under conditions of impaired mitochondrial function the representative compounds of Formula (I) significantly improve protection of cell viability, especially when compared against the comparative compounds Menadione and Idebenone. Comparative compound vitamin K exhibited no protective effect.

Example 20: Cell Viability in the Presence of a Mitochondrial Inhibitor

The cytoprotective effects of representative compounds of Formula (I) were further examined in vitro in response to rotenone toxicity at (10 µM). Representative compounds were assessed in HepG2 cells in the presence of the mitochondrial toxin, rotenone, under similar conditions to Example 19. Cells were treated with the representative compounds of Formula (I) compounds (10 µM) for 2 days before cells were challenged with 10 µM rotenone.

As highlighted in FIG. 1, under conditions of impaired mitochondrial function the representative compounds of Formula (I) significantly improve cell viability. Representative naphthoquinone compounds of Formula (I) (labelled N) were compared with the corresponding benzoquinone (B) or a plastoquinone (C) derivative. Despite comprising identical substituents at L, Y, $R^5$, $R^6$, the equivalent benzoquinone (B) or plastoquinone (P) derivatives exhibited overall lower cytoprotective activity than the corresponding naphthoquinone of Formula (I).

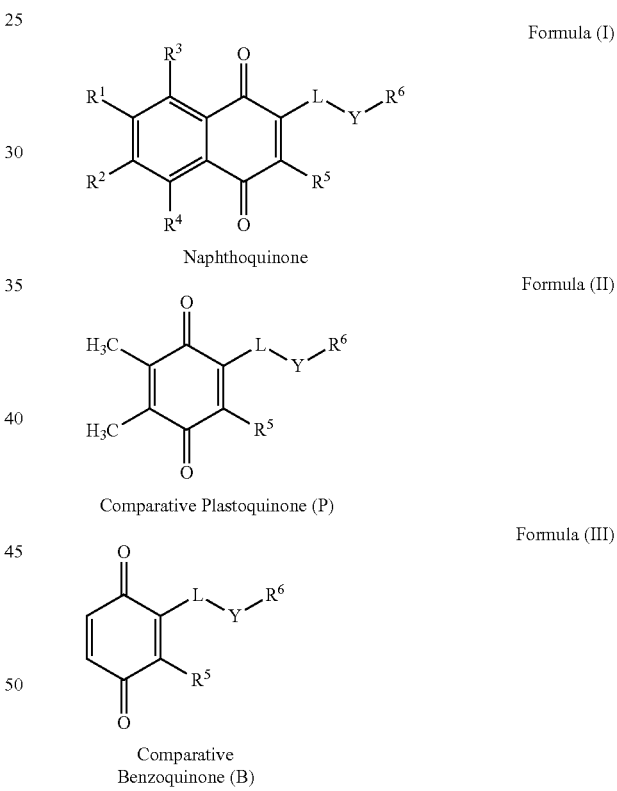

Formula (I)

Naphthoquinone

Formula (II)

Comparative Plastoquinone (P)

Formula (III)

Comparative Benzoquinone (B)

Figure 2:
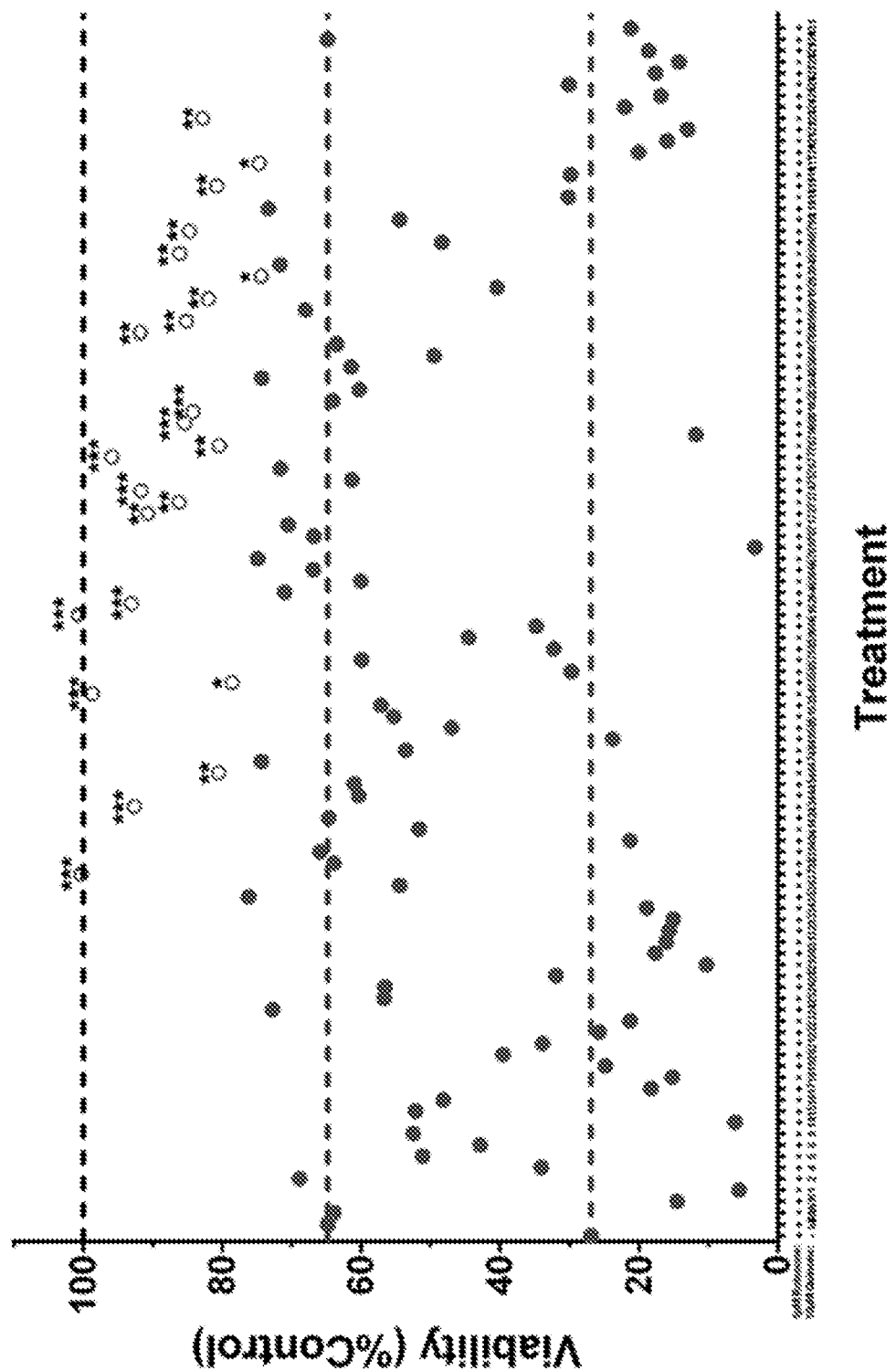
FIG. 2: Cytoprotective effects of compounds of Formula (I) (10 μM) in vitro against rotenone toxicity. 23 compounds (white circles) demonstrated significantly improved cytoprotective activity compared to idebenone (dotted line, −65% viability). In cells exposed to rotenone only, viability dropped from 100% (black dotted line, 100% viability) to below 30% (dotted line, <30% viability).

As highlighted in FIG. 2; 23 compounds (white circles) demonstrated significantly improved cytoprotective activity compared to idebenone (dotted line, ~65% viability). In cells exposed to rotenone only, viability dropped from 100% (black dotted line, 100% viability) to below 30% (dotted line, <30% viability).

Cellular viability against a rotenone challenge of representative compounds of Formula (I) is summarised below in Table 6, corresponding to data in FIG. 2. Vitamin K, Menadione and Idebenone were used as comparative controls.

TABLE 6

Cell Viability [%] [10 uM] HepG2

| COMPOUND NO. | CELL VIABILITY [%] | SD | n |
|---|---|---|---|
| Idebenone | 66.2 | 13.9 | 11 |
| Vitamin K | 14.5 | 7.6 | 3 |
| Menadione | 64.0 | 18.3 | 3 |
| 2 | 68.9 | 12.4 | 5 |
| 24 | 72.8 | 12.7 | 5 |
| 35 | 76.2 | 17.3 | 5 |
| 37 | 100.3 | 16.7 | 8 |
| 42 | 64.7 | 6.5 | 4 |
| 43 | 92.7 | 7.6 | 4 |
| 46 | 80.5 | 11.5 | 3 |
| 47 | 74.4 | 5.6 | 3 |
| 54 | 98.7 | 10.9 | 3 |
| 55 | 78.6 | 14.1 | 3 |
| 61 | 100.7 | 2.1 | 3 |
| 62 | 93.1 | 9.6 | 8 |
| 65 | 60.1 | 13.5 | 3 |
| 66 | 66.9 | 3.9 | 3 |
| 67 | 74.9 | 18.5 | 3 |
| 70 | 66.8 | 6 | 3 |
| 71 | 70.5 | 19.5 | 3 |
| 72 | 90.7 | 15.6 | 3 |
| 73 | 86.2 | 9.4 | 3 |
| 74 | 91.7 | 22.8 | 3 |
| 75 | 61.4 | 7.3 | 3 |
| 76 | 68.1 | 14.3 | 4 |
| 77 | 95.9 | 25.2 | 3 |
| 78 | 80.0 | 21.0 | 7 |
| 80 | 87.6 | 19.6 | 7 |
| 81 | 83.8 | 19.9 | 7 |
| 84 | 74.4 | 3.8 | 3 |
| 85 | 61.4 | 9.6 | 3 |
| 88 | 91.8 | 8.8 | 3 |
| 89 | 85.2 | 10.1 | 3 |
| 91 | 82.0 | 7.1 | 3 |
| 93 | 74.4 | 4.3 | 3 |
| 94 | 71.7 | 7.4 | 3 |
| 95 | 86.1 | 4.9 | 3 |
| 97 | 84.8 | 6.6 | 3 |
| 113 | 73.4 | 6.5 | 3 |
| 115 | 80.8 | 4.6 | 3 |
| 117 | 80.3 | 11.4 | 3 |

TABLE 7

% ATP rescue [10 uM] HepG2

| COMPOUND NO. | % ATP RESCUE | SD | n |
|---|---|---|---|
| idebenone | 81.0 | 10.0 | 13 |
| Vitamin K1 | 3.5 | 5.1 | 1 |
| Menadione | 30.6 | 0.6 | 1 |
| 20 | 44.46 | 5.6 | 1 |
| 22 | 33.0 | 11.2 | 1 |
| 24 | 47.4 | 14.2 | 1 |
| 35 | 76.7 | 7.6 | 4 |
| 37 | 64.2 | 1.6 | 6 |
| 42 | 79.1 | 9.3 | 3 |
| 46 | 53.7 | 7.1 | 3 |
| 47 | 76.4 | 5.2 | 3 |
| 54 | 66.1 | 12.6 | 3 |
| 55 | 94.8 | 4.1 | 3 |
| 59 | 79.9 | 20.2 | 3 |
| 61 | 78.6 | 5.1 | 3 |
| 62 | 91.2 | 6.6 | 7 |
| 65 | 91.1 | 11.7 | 3 |
| 66 | 73.3 | 17.3 | 3 |
| 67 | 97.1 | 12.2 | 3 |
| 70 | 91.8 | 12.8 | 3 |
| 71 | 92.2 | 3.1 | 3 |
| 72 | 84.8 | 17.6 | 3 |
| 73 | 96.1 | 1.4 | 3 |
| 74 | 100.7 | 3.9 | 3 |
| 75 | 95.4 | 9.5 | 3 |
| 76 | 51.4 | 6.9 | 3 |
| 77 | 99.1 | 7.6 | 3 |
| 78 | 84.2 | 10.1 | 6 |
| 80 | 89.1 | 12.2 | 6 |
| 81 | 89.9 | 13.1 | 6 |
| 83 | 73.5 | 5.0 | 3 |
| 84 | 90.4 | 4.5 | 3 |
| 88 | 80.2 | 20.8 | 3 |
| 89 | 90.0 | 15.5 | 3 |
| 91 | 77.4 | 10.2 | 3 |
| 93 | 82.7 | 9.0 | 3 |
| 94 | 65.3 | 3.8 | 3 |
| 95 | 83.7 | 5.3 | 3 |
| 97 | 81.1 | 8.2 | 3 |
| 113 | 65.6 | 8.8 | 3 |
| 115 | 67.2 | 3.5 | 3 |
| 117 | 40.4 | 3.1 | 3 |

Example 21: ATP Rescue in the Presence of a Mitochondrial Inhibitor

The extent of ATP rescue of representative compounds of Formula (I) were further examined in vitro in response to rotenone toxicity at (10 µM). Representative compounds were assessed in HepG2 cells in the presence of the mitochondrial toxin, rotenone, under similar conditions to Example 18. Cells were treated with the representative compounds of Formula (I) compounds (10 µM) for 2 days before cells were challenged with 10 µM rotenone.

Figure 3:
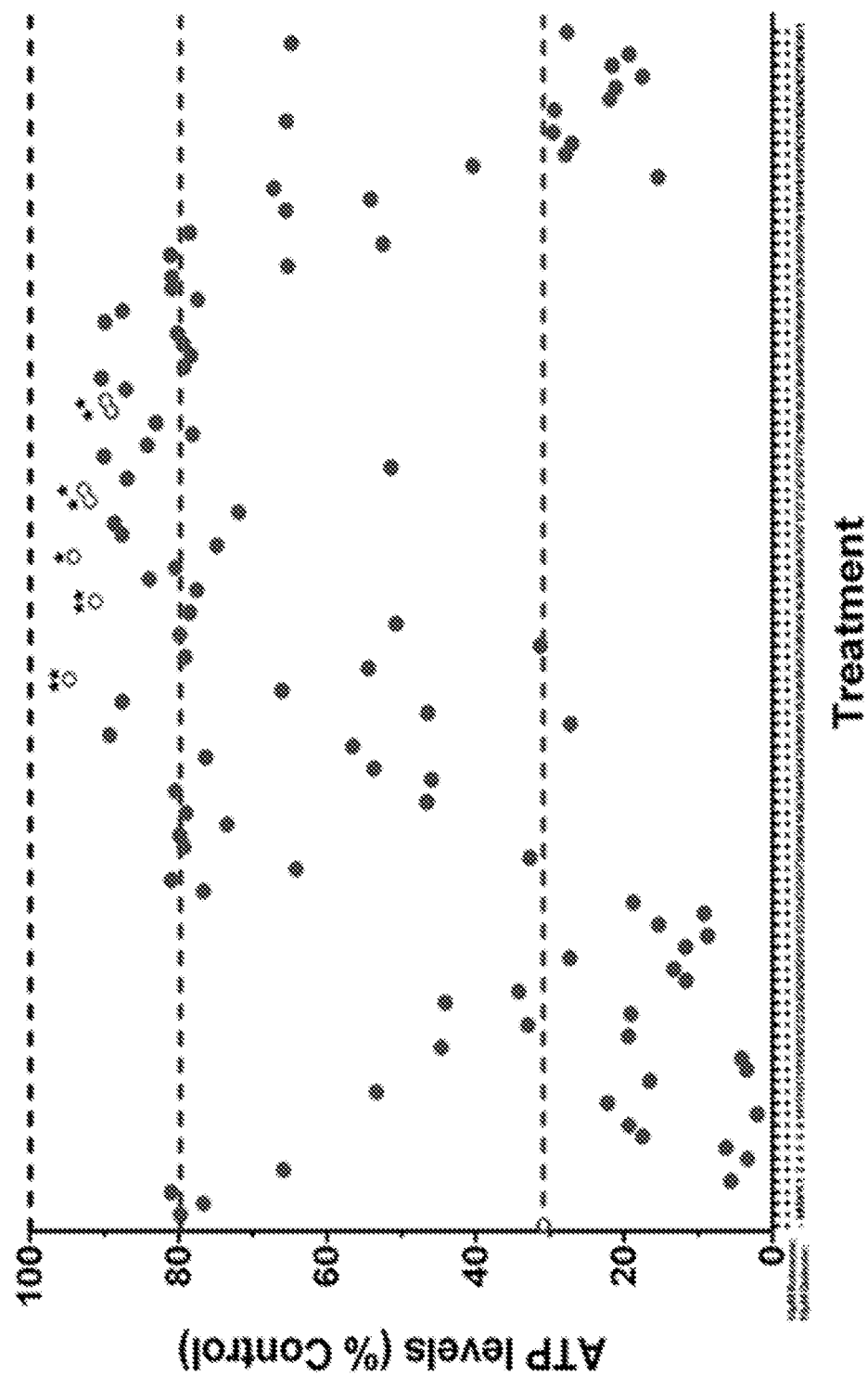
FIG. 3: Comparative ATP levels in vitro following treatment with compounds of Formula (I) (10 μM) against rotenone toxicity. 7 compounds (white circles) significantly increased cellular ATP levels compared to idebenone (dotted line, ~80% viability) in the presence of rotenone. In cells exposed to rotenone only, viability dropped from 100% (black dotted line, 100% viability) to below 30% (dotted line, <30% viability). All compounds were tested at 10 µM.
Figure 4:
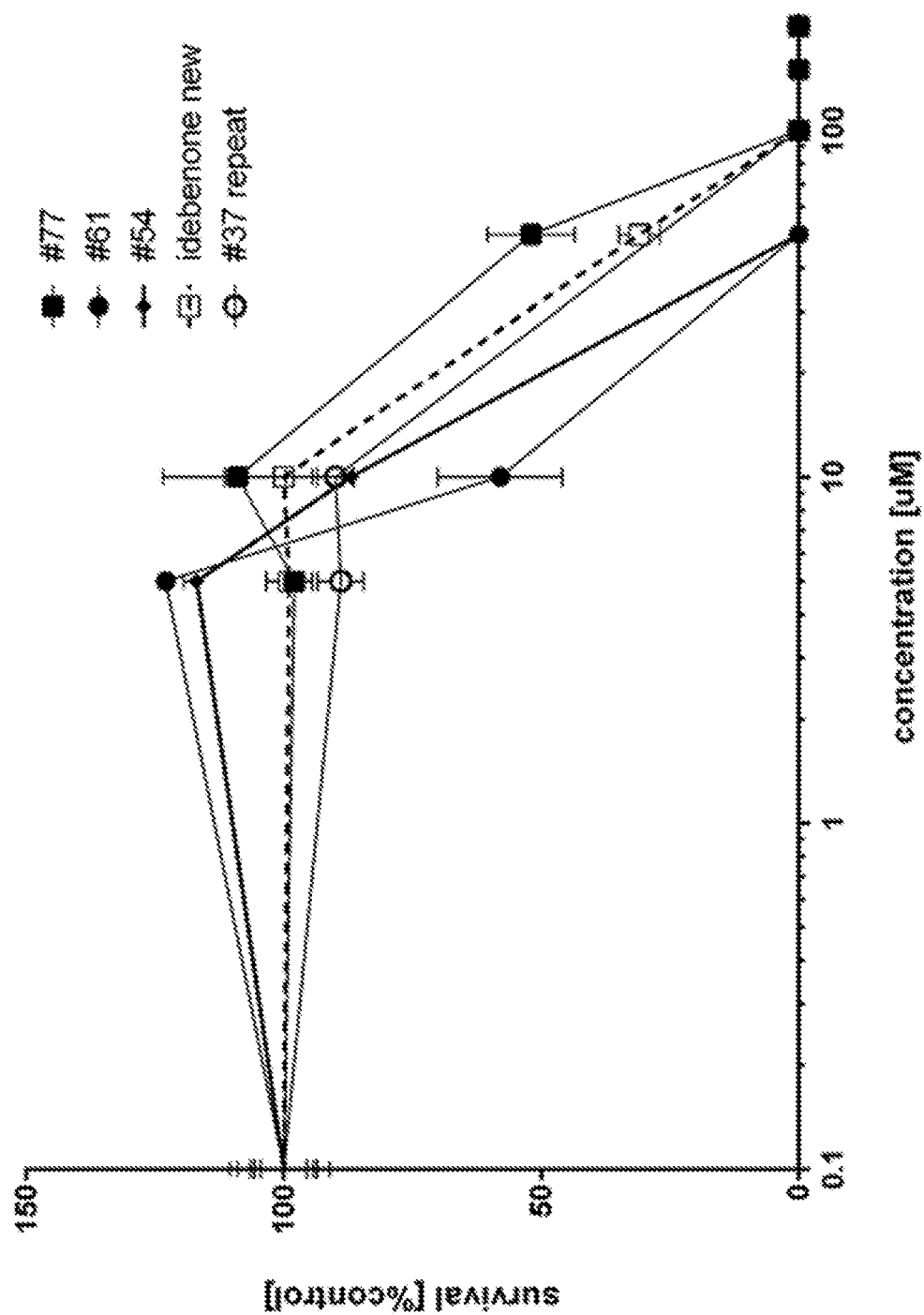
FIG. 4: Toxicity in vitro of representative compounds of Formula (I) (10 µM) compared to idebenone in liver cells. Long term toxicity assessed using colony formation assays in HepG2 cells over a period of 14 days for representative compounds. Representative compounds exhibited similar in vitro toxicity to idebenone.

As highlighted in FIG. 3, 7 compounds (white circles) significantly increased cellular ATP levels compared to idebenone (violet dotted line) in the presence of rotenone. In cells exposed to rotenone only, viability dropped from 100% (black dotted line, 100% viability) to below 30% (dotted line, <30% viability). All compounds were tested at 10 µM.

ATP rescue against a rotenone challenge of representative compounds of Formula (I) is summarised below in Table 7, corresponding to data in FIG. 2. Vitamin K, Menadione and Idebenone were used as comparative controls.

Example 22: Effects on Extracellular Lactate Levels

Mitochondrial dysfunction, and the subsequent reduced ATP production is typically compensated by the cell via an increased glycolysis to maintain ATP levels. However, this is typically also associated with an increase in the glycolysis by-product lactate. Lactate at higher concentrations acidifies the media and becomes toxic in vitro and in vivo (called lactic acidosis). Hence reduction of lactate levels by test compounds is indicative of improved mitochondrial function.

Lactate concentrations in culture medium were determined by an enzyme-linked colorimetric assay. Briefly, 150,000 HepG2 cells were seeded in normal growth media (DMEM, 10% FCS, Pen/Strep) in each well of a 6-well plate (Life Science, USA) and incubated for 24 h. The media was replaced with growth media containing (25 mM glucose,) with and without test compounds. Three untreated wells containing only cells were considered the experimental baseline control and all compounds were tested in three different wells simultaneously. Supernatants were collected after 48 h and transferred into 96-well format. After the addition of 90 µl of reaction buffer (10 mM KH2PO4 pH 7.8, 1 mg/ml BSA, 0.5 mM PMS, 2 mM EDTA, 0.6 mM DCPIP, 0.8 mM NAD+, 5 U/ml glutamate-pyruvate-transaminase, 1.5 mM glutamate, 12.5 U/ml lactate dehydrogenase) the plate was incubated at 30° C. inside a multimode plate reader (Multiscan Go, Thermo Scientific) and absorbance was measured at 600 nm over a period of 100 minutes. A standard curve was generated using media spiked with known lactate concentrations. Finally, protein levels were quantified and the lactate concentration of each well was standardized to its protein content and was then expressed as % of control.

The extent of lactate reduction in the cell culture media by the test compounds of the subject invention and the Comparative Compounds vitamin K, menadione and idebenone is shown below in Table 6.

TABLE 8

Effect on lactate levels

| Compound No. | Extracellular lactate [% control] |
| --- | --- |
| Vehicle control (DMSO only) | 100 |
| Vitamin K | 92.0 |
| Menadione | 163.3 |
| idebenone | 111.9 |
| 19 | 65.3 |
| 20 | 78.6 |
| 21 | 75.6 |
| 22 | 73 |
| 54 | 79.1 |
| 66 | 66 |
| 67 | 67.6 |
| 70 | 73.3 |

As highlighted in Table 6, representative compounds of Formula (I) significantly reduced lactate production, which is indicative of improved mitochondrial function. Comparative compounds menadione and idebenone in contrast were found to increase lactate concentrations. Comparative compound vitamin K exhibited only a slight but non-significant effect.

Example 23: Toxicity In Vivo

Figure 5:
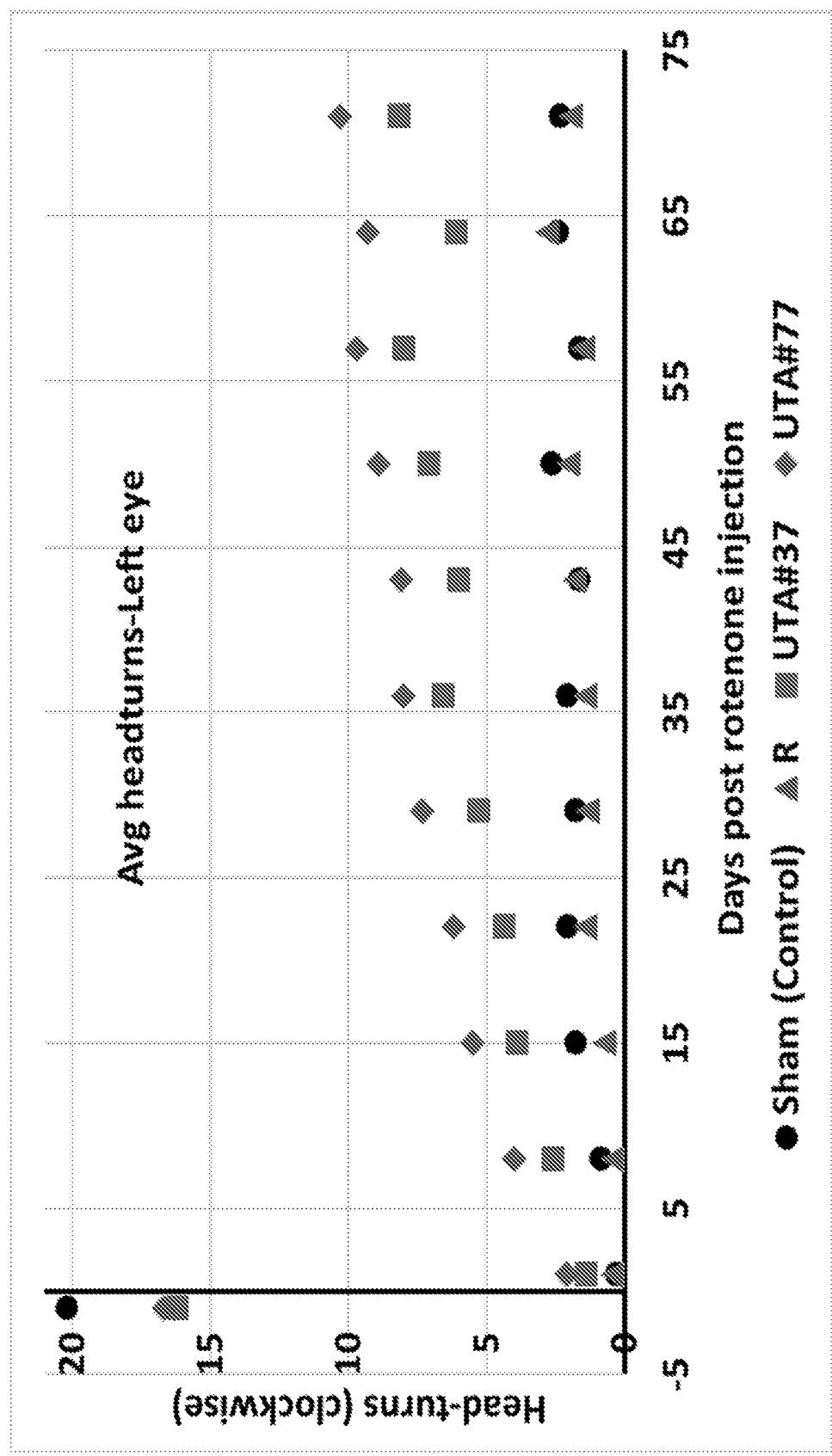
FIG. 5: Efficacy of representative compounds of Formula (I) in leber's hereditary optic neuropathy (LHON) mouse model. LHON induced by rotenone injection in the left eye (5 µM) in C57BL/6 mouse model (Refer to Heitz, F. D et al. (2012). *PLoS One.*, 7(9), e45182). Treatment with representative compounds resulted in increased in vivo protection of vision compared to idebenone control. Representative compounds (UTA 37 and UTA 77) and idebenone administered at 200 mg/kg over the observation period. Statistically significant protection of visual acuity was observed with the representative compounds UTA 37 and UTA 77 but not with idebenone (labelled as R in FIG. 5) at this concentration.

The toxicity of representative compounds of Formula (I) in vivo was in liver cells. Specifically, long term toxicity assessed using colony formation assays in HepG2 cells was assessed over a period of 14 days for representative compounds of Formula (I) at 10 µM. Idebenone was used as a comparative control (10 µM). As highlighted in FIG. 5; the representative compounds of the invention exhibited similar in vitro toxicity to idebenone.

Example 24: Activity in Leber's Hereditary Optic Neuropathy (LHON) Model

The efficacy of representative compounds of Formula (I) was assessed in Leber's hereditary optic neuropathy (LHON) mouse model. LHON is a rare inherited mitochondrial disorder characterized by rapid loss of visual acuity and colour contrast sensitivity leading to blindness. LHON is caused by mitochondrial DNA (mtDNA) mutations, among which three so called primary mtDNA mutations account for more than 95% of all LHON cases.

LHON model was induced by intravitreal injection of rotenone into the left eye in C57BL/6 mouse model as described by Heitz et al. 2012. Representative compounds (UTA 37 and UTA 77) and idebenone administered at 200 mg/kg over the observation period. Vision loss was measured by assessing number of head turns.

C57BL/6 mice (male, 8-11 weeks of age, average body weight≈25 g) were used in accordance with the Australian code for the use of animals for scientific purposes and under the required animal ethics approval from the University of Tasmania (UTAS) Animal Ethics Committee (Approval number A0016080). Animals were given at least seven days to acclimatise to the animal facility to reduce stress induced by transportation before being used for behavioural testing. All mice were supplied orally with test compounds by mixing test compounds into individual daily food portions as described previously (Heitz, F. D. et al. (2012). *PLoS One.*, 7(9), e45182). To control drug intake, mice were individually caged and were provided with enriched environment including housing and bedding material, small toys, autoclaved toilet rolls, small wooden sticks for gnawing and glass marbles to provide the opportunity for natural behaviour. All mice (n=10-11 per group) were pre-treated with the test compounds at 200 mg/kg body weight for 7 days prior to intraocular injection of the mitochondrial toxin, rotenone and subsequently for the remainder of the study period. Test compounds were formulated with food powder to produce individual portions that were placed into the cage once a day. Briefly, test compounds (20 mg/ml) were stirred overnight at 4° C. in 500 ml 0.5% carboxymethylcellulose (CMC) solution. To 37.5 ml of the CMC solution, 41.25 g sucrose, 371.25 g food powder and 0.5% CMC solution were mixed to prepare a food mash, which was aliquoted (5.5 g portions) in weighting trays and individually stored at ~20° C. Ad libitum supply of additional food pellets and water was ensured throughout the study. To induce mitochondrial dysfunction-induced vision loss, mice were anesthetized by 5% isoflurane (600 ml/min oxygen) which was reduced to 2% isoflurane (300 ml/min oxygen) for the duration of surgery. Prior-to and after intraocular injection, cotton buds soaked with sterile saline were used to clean the area around the eyes. For intravitreal injection, a 31-gauge needle was used to puncture the sclera and the eye was gently massaged to remove a small amount of vitreous to prevent subsequent increases in intraocular pressure. Then, a 33-gauge needle adapted to a 10 µl Hamilton syringe (Intraocular injection kit, World Precision Instruments, USA) was used to inject 1 µl of rotenone (5 mM in dimethyl sulphoxide) into the vitreous chamber of the left eye. The right eye served as internal control. The needle tip was inserted into the superior hemisphere of the eye, at the level of the pars plana and at a 450 angle through the sclera into the vitreous body. This route of administration avoids retinal detachment or injury to eye structures, including the lens and the iris. The mice were then allowed to recover on a heating pad and then returned to their home cages. The injected eye was carefully checked once a day for 7 days post-surgery for signs of inflammation. Visual acuity of the mice was repeatedly tested every week using the optomotor response, as described previously (Heitz et al. 2012). Mice were placed on a small platform surrounded by a motorized drum (30 cm diameter) with vertical black and white stripes (1 cm thickness). After a 10 min adaptation period to the system, visual acuity testing was performed by rotating the stripes clockwise and counter-clock-wise at two revolutions/min for two minutes in each direction and with an interval of 30 seconds between the two rotations. The behaviour of the mice was recorded with a digital video camera for subsequent scoring of head tracking movements. All analysis of video material was done in an investigator blinded manner. At the end of the observation period all mice were terminally anaesthetised with intraperitoneal sodium pentobarbital (110 mg/kg body wt.).

Treatment with representative compounds of Formula (I) resulted in increased in vivo protection of vision compared to idebenone control. As highlighted in FIG. 5 significant protection of visual acuity was observed with the representative compounds UTA 37 and UTA 77 but not with idebenone (labelled as R in FIG. 5) at this concentration.

Example 25: Activity in Diabetic Retinopathy Model

Diabetic retinopathy (DR) is a complications associated with chronic hyperglycemia in patients with diabetes mellitus. The activity of compounds of the invention was assessed in a chemically-induced diabetic retinopathy rat model, wherein streptozotocin (STZ) administration induces disease development in Long Evans rats. Blood glucose response and visual acuity was each examined following treatment with representative compounds of Formula (I).

Male Long-Evans rats at 30 weeks of age; average body weight—400 g were used. Rats were housed in groups of three at 21±2° C. with a 12 hr-12 hr light-dark cycle. Food and water was be provided ad libitum throughout the study. Type 2 diabetes was induced as described previously (Premilovac D, et al. (2017) *Sci Rep.* 7(1) pp. 14158) that combines a high fat diet (HFD; causes obesity associated insulin resistance) with osmotic mini-pump delivered streptozotocin (STZ) to reduce the number of insulin producing beta cells. This combination imparts control over the resulting level of hyperglycaemia while retaining an obese, insulin resistant phenotype, typical of human type 2 diabetes.

Over the first 4 weeks, bodyweight, blood glucose levels, water intake and visual acuity were monitored, before an osmotic mini pump was surgically implanted. As soon as blood glucose levels reached 20 mM, the pumps were removed. Within 5 weeks after the initial surgery, a significant loss of visual acuity was detected. For visual acuity testing the optokinetic response (OKR) was determined. Rats were placed on a small platform surrounded by a motorized drum (70 cm diameter) with vertical black and white stripes (6.11 cm thickness). After a 10 min adaptation period to the system, visual acuity testing was performed by rotating the stripes clock-wise and counter-clock-wise at 2.61 revolutions/min for two minutes in each direction and with an interval of 30 seconds between the two rotations to assess visual acuity for the left and right eye. The behaviour of rats was recorded with a digital video camera for subsequent scoring of head tracking movements. All analysis of video material was done in an investigator-blinded manner.

Diabetic rats (n=3-10) were divided randomly into 4 different study arms
  1. no intervention;
  2. treatment with idebenone;
  3. treatment with UTA 37,
  4. treatment with UTA 77.

Test compounds were dissolved in eye drop solution (5% tyloxapol, 5% mineral oil in 66 mM citrate buffer pH 7.4) at 10 mg/ml for idebenone, 4.6 mg/ml for UTA 37 and 7.36 mg/ml for UTA 77. From week 14, the right eyes of the diabetic rats were treated with test-compound-containing eye drop solution once a day (applied volume of approx. 50 μl). The left (untreated eye) served as internal control. At the end of the observation period (week 21) all animals were euthanized and tissues were collected.

Figure 6:
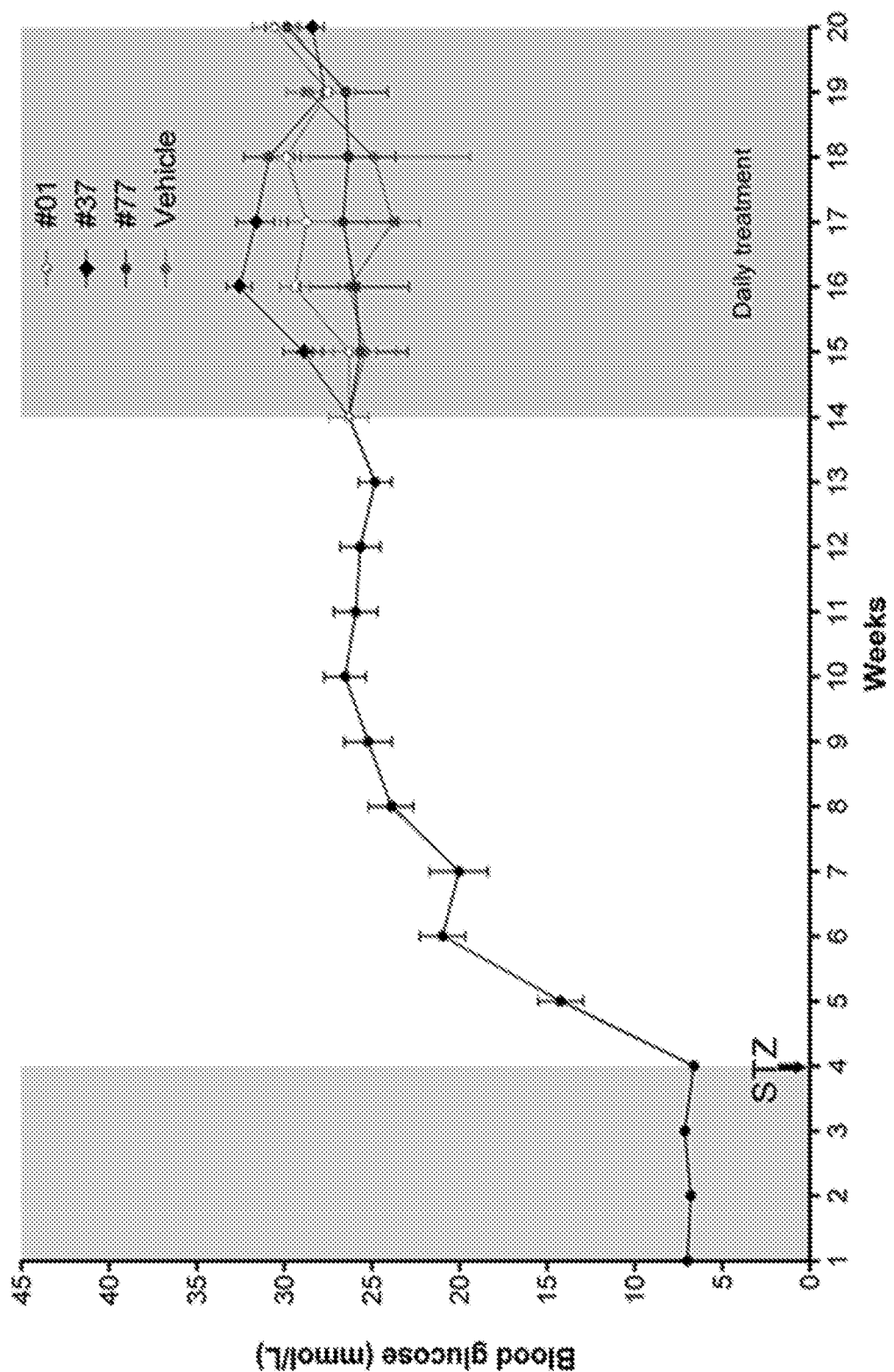
FIG. 6: Blood glucose response in diabetic retinopathy rat model following treatment with representative compounds of Formula (I). Long Evans rats were implanted with streptozotocin (STZ) (125 mg/kg) osmolarity pumps at week 4 upon which blood glucose levels rapidly increased over time. At week 14, eye drops were administered once daily with representative compounds of formula (I) (UTA37 4.6 mg/ml; UTA77 7.36 mg/ml), idebenone (labelled #1; 10 mg/ml) or vehicle control. n=23 eyes/group for untreated eyes (week 1-14), n=10 eyes/group (week 14-18 & n=7 eyes/group week 18-20) for #01 treated eyes, n=4 eyes/group and 7 eyes/group for UTA37 and UTA77 respectively (from week 14-20), n=2 eyes/group for vehicle treatment.

As highlighted in FIG. 6, implantation of streptozotocin (STZ) (125 mg/kg) osmolarity pump at week 4 upon resulted in rapidly increased blood glucose levels in Long Evans rats. Once daily administration of eye drops comprising any one of idebenone, UTA37 and UTA 77 did not significantly alter systemic blood glucose levels compared to control rats.

Figure 7:
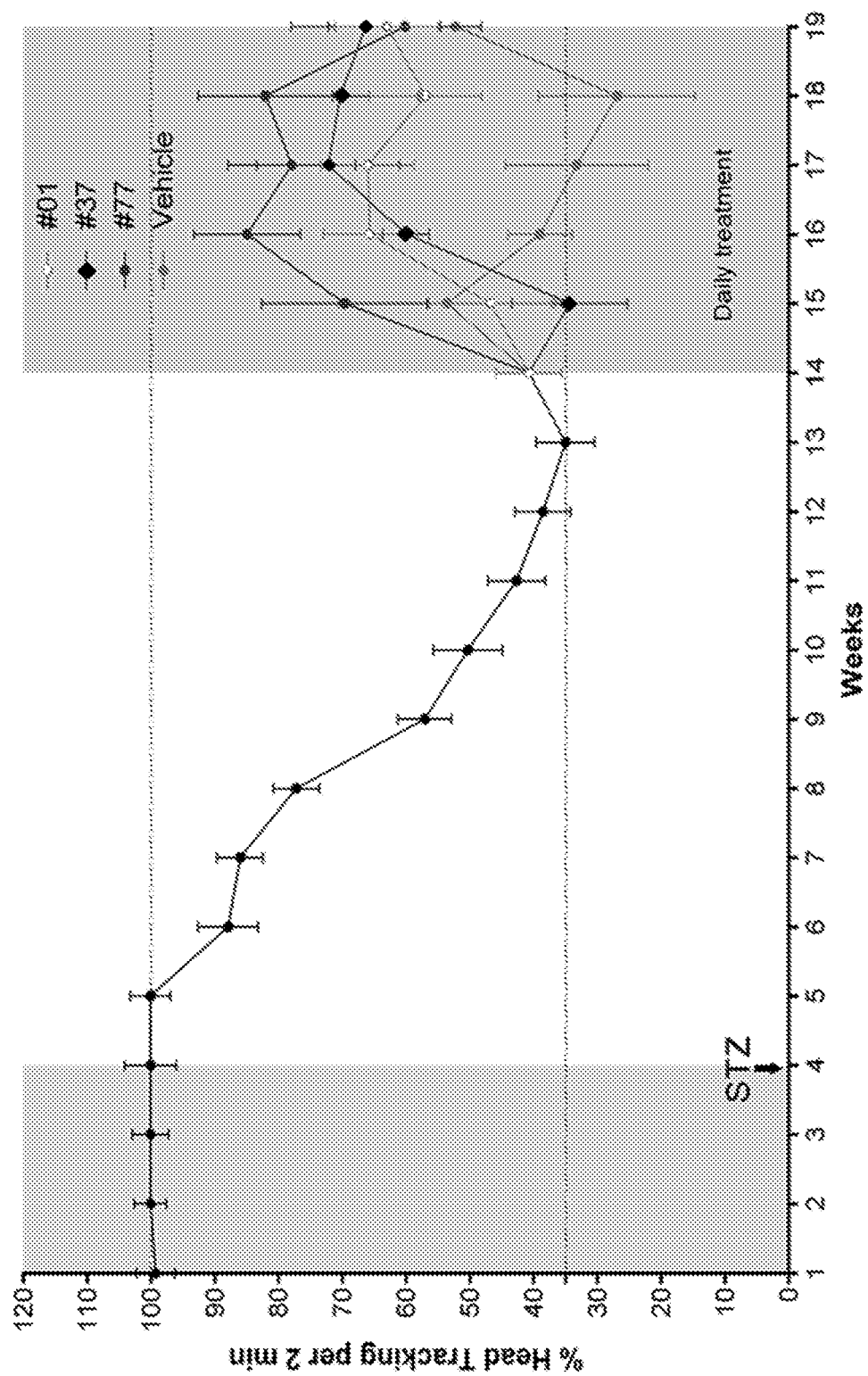
FIG. 7: Visual acuity in diabetic retinopathy rat model following treatment with representative compounds of Formula (I). Visual acuity was measured using optokinetic response for both left and right eyes of Long Evans rats over a period of 19 weeks. Streptozotocin (STZ) administration (week 4) significant impaired reflex head movement by week 9. At week 14, eye drops were administered once daily with representative compounds of formula (I) (UTA37 4.6 mg/ml; UTA77 7.36 mg/ml), idebenone (#1; 10 mg/ml) or vehicle control. n=23 eyes/group for untreated eyes (week 1-14), n=10 eyes/group (week 14-18 & n=7 eyes/group week 18-19) for idebenone (#1) treated eyes, n=4 eyes/group and 7 eyes/group for UTA37 and UTA77 respectively (from week 14-19). While n=2 eyes/group for vehicle control treatment. Error bars=SEM

As highlighted in FIG. 7, visual acuity was assessed using optokinetic response for both left and right eyes of Long Evans rats over a period of 19 weeks. Streptozotocin (STZ) administration at week 4 significant impaired reflex head movement by week 9. At week 14, eye drops were administered once daily with representative compounds of formula (I). Compounds of formula (I) were efficacious in the diabetic retinopathy model. Specifically, once daily administration of representative compounds of Formula (I) partially restored visual acuity following impairment with STZ, as measured by optokinetic response, suggesting such compounds may be effective for the treatment of secondary complications associated with diabetes, including ocular implications associated with diabetes.

Example 26: Activity in Colitis Model

Ulcerative colitis (UC) is a form of chronic inflammation of the gastrointestinal tract, typically in the colon and rectum. Symptoms include the development of bloody diarrhoea with or without mucus, rectal urgency, tenesmus, abdominal pain, weight loss, fatigue and extraintestinal manifestations. A dextran sulfate sodium (DSS) induced colitis model is accepted as a relevant mouse model for ulcerative colitis in humans.

Figure 9:
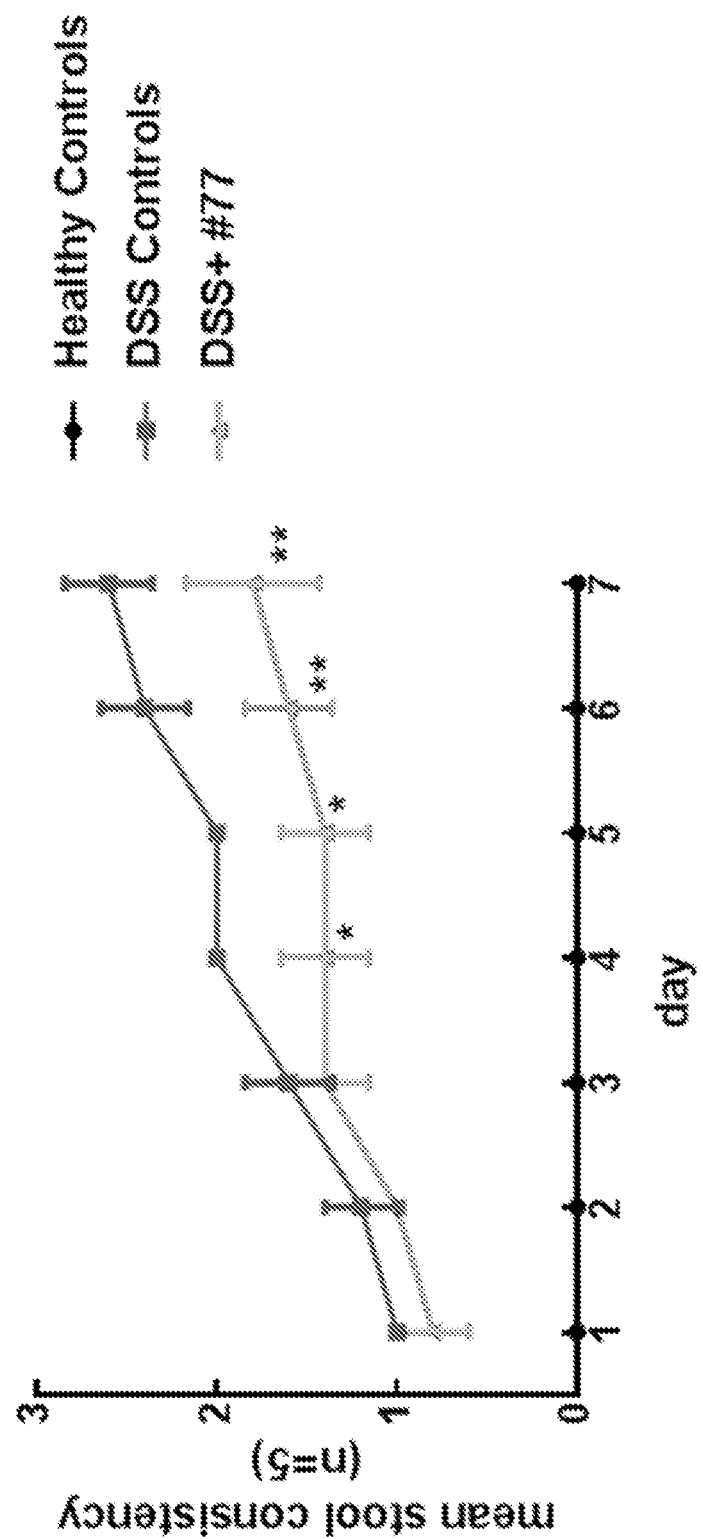
Figure 10:
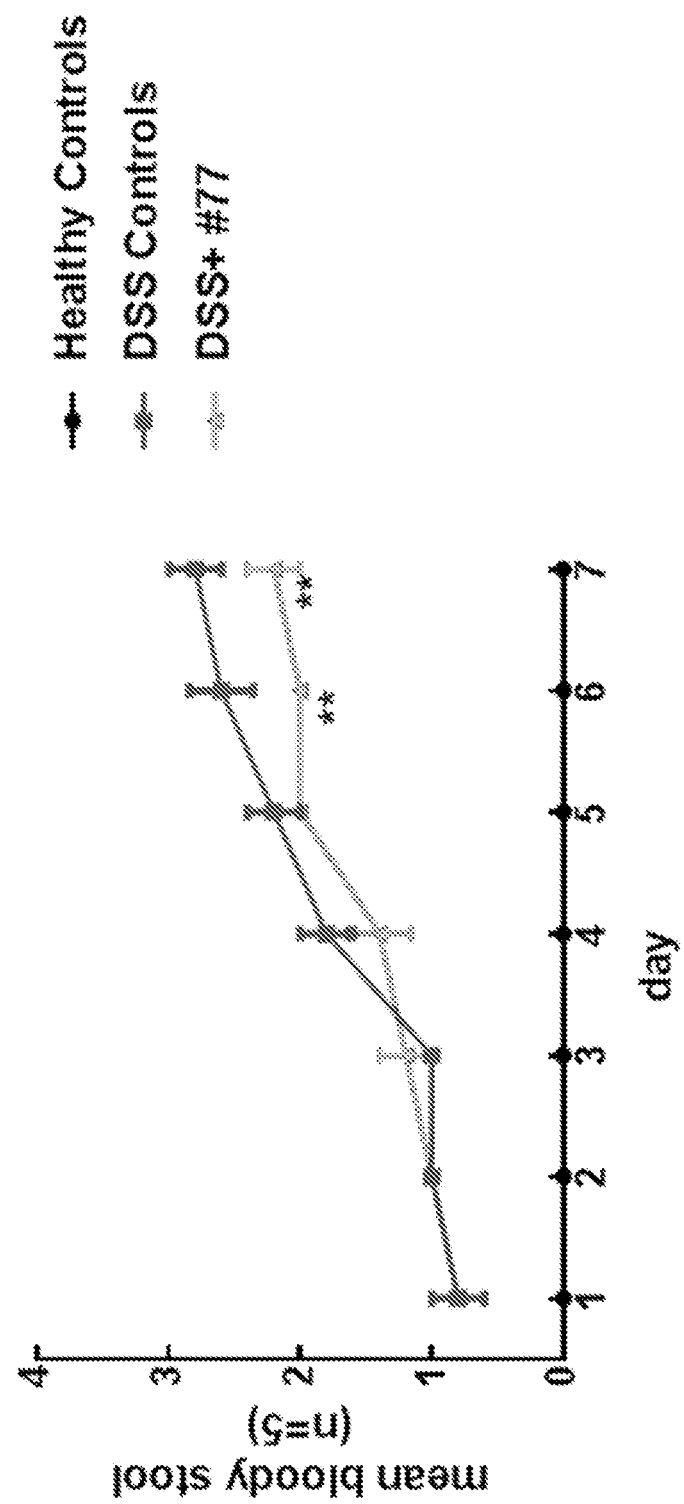
Figure 11:
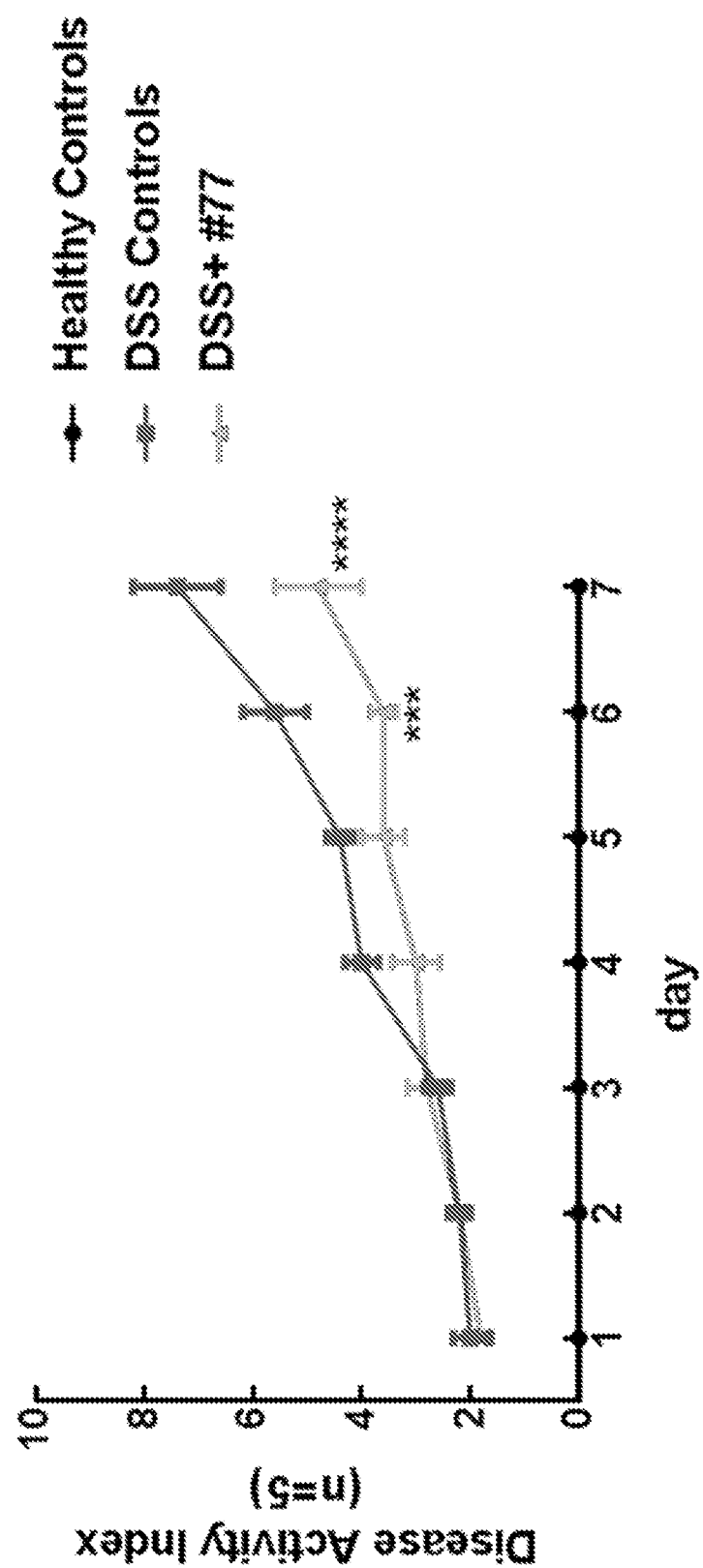

Colitis was chemically induced in mice by administration of 2.5% dextran sulfate sodium (DSS). Body weight (refer to FIG. 8), stool consistency (refer to FIG. 9), blood content of stools (refer to FIG. 10), and general disease activity index (refer to FIG. 11) were all assessed following treatment with representative compound of Formula (I), UTA77.

Female C57BL/6 mice were used at 7-8 weeks of age having an average body weight≈17 g. Mice were divided randomly into three different groups:
  1. a healthy control group without DSS,
  2. a control group with DSS,
  3. a group treated with DSS and test compound (n=5 per group).

Figure 8:
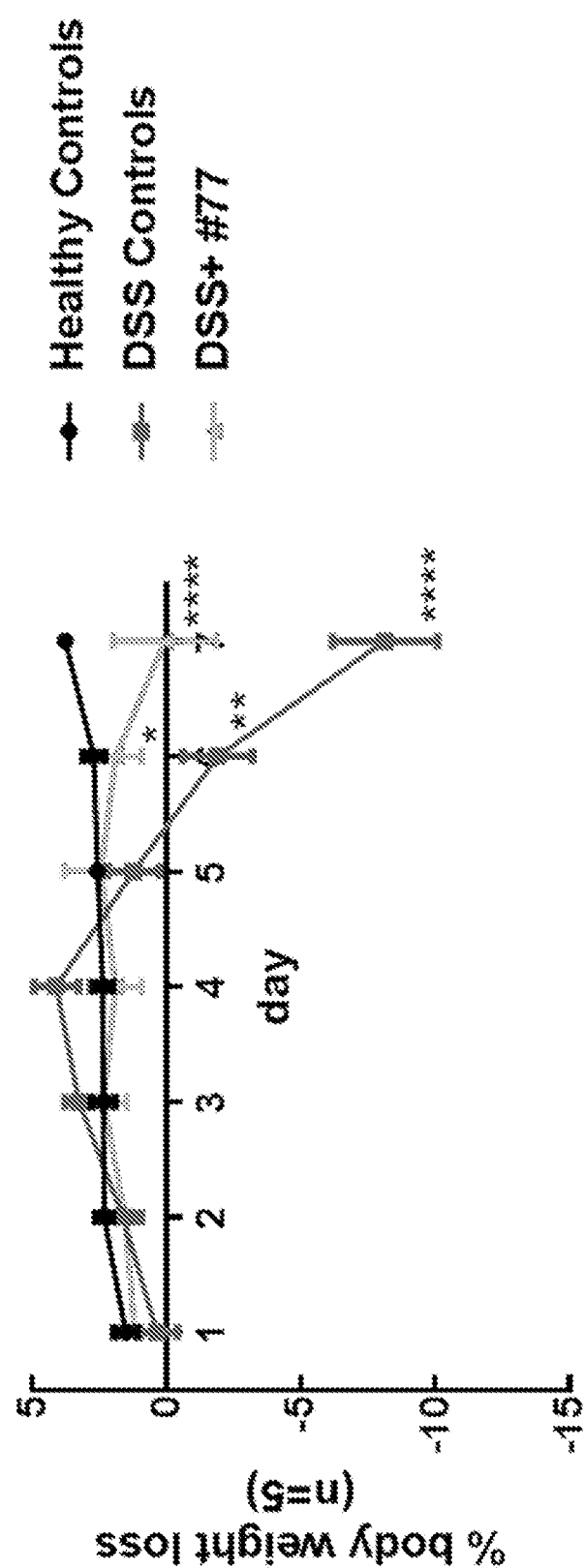
FIGS. 8-11: Ulcerative Colitis mouse model following treatment with representative compound of Formula (I) (UTA77)

Body weight of mice were assessed daily over an initial acclimation period of one week (FIG. 8). All mice were non-fasting and had access to food and drinking water (autoclaved tap water) ad libitum. Representative compounds of Formula (I) were formulated with food powder (200 mg/kg of body weight) to produce individual portions that were placed into the cage once a day. Representative compounds of Formula (I) (20 mg/ml) were stirred overnight at 4° C. in 500 ml 0.5% carboxymethylcellulose (CMC) solution. To 37.5 ml of the CMC solution, 41.25 g sucrose, 371.25 g food powder and 0.5% CMC solution were mixed to prepare a food mash, which was aliquoted (2.2 g portions) in weighting trays and individually stored at −20° C. Colitis was induced by supplementing 2.5% w/v of dextran sulphate sodium (DSS, MW=36,000-50,000, colitis grade, MP Biomedicals, USA) in the drinking water of mice from day 0 to day 7 (day of termination). On day 0, all mice were weighed and checked for stool consistency and occult blood before they were exposed to DSS and test compounds. Control animals were only supplied with autoclaved drinking water without DSS, and normal chow pellets, while 2.5% DSS in tap water was provided to the DSS-treated groups from day 0 to day 7. All controls groups were also supplied with 2.2 g of food mash without test compounds. The animals of the drug-treated groups received 200 mg/kg of test compounds in food mash with 2.5% of DSS in water from day 0 to day 7. Body weight (refer to FIG. 8), stool consistency (refer to FIG. 9), blood content of stools (refer to FIG. 10) were recorded daily. The Disease Activity Index (DAI) (FIG. 11) was calculated according to scoring Table 9 below. Each parameter was scored independently and all three parameters were added to calculate the DAI.

TABLE 9

| Parameters score for Disease Activity Index (DAI) Calculation | | | |
| --- | --- | --- | --- |
| Score | Stool consistency | Blood in Stool | Weight loss |
| 0 | Normal Pellet | hemoccult negative | 0 |
| 1 | Soft but formed | hemoccult positive | 1-5% |
| 2 | Loose/v. soft stool | blood visually present | 6-10% |
| 3 | Watery Stool | gross bleeding | 11-15% |

Mice treated with UTA77 exhibited reduced disease activity, improved stools and a reduction in bloody stools when compared to DSS controls. Furthermore, mice treated with UTA77 exhibited less weight loss than DSS controls over the treatment period.

The invention claimed is:

1. A compound of Formula (Ib):

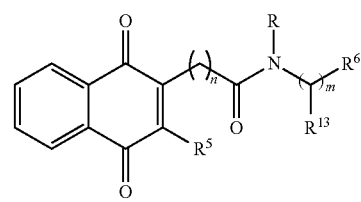

Formula (Ib)

or a pharmaceutically acceptable salt thereof, wherein:
$R^5$ is selected from H and methyl,
$R^6$ is optionally substituted $C_5$-$C_{12}$ aryl,
R is H or optionally substituted $C_1$-$C_6$ alkyl;
$R^{13}$ at each occurrence is independently selected from H, optionally substituted phenyl, and optionally substituted benzyl,
n is an integer selected from 1, 2, 3, 4 and 5, and
m is an integer selected from 1, 2, and 3.

2. A compound according to claim 1 wherein $R^6$ is optionally substituted $C_6$ aryl.

3. A compound according to claim 1, wherein $R^6$ is dimethoxy phenyl, preferably 3,4-dimethoxy phenyl.

4. A compound according to claim 1 wherein $R^5$ is H.

5. A compound according to claim 1 wherein $R^5$ is methyl.

6. A compound selected from the group consisting of:

| Designated No. | Structure |
| --- | --- |
| UTA #35 | 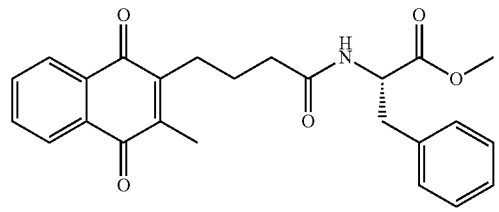 [SMILES: COC(=O)[C@H](Cc1ccccc1)NC(=O)CCCC1=C(C)C(=O)c2ccccc2C1=O] |
| UTA #37 | 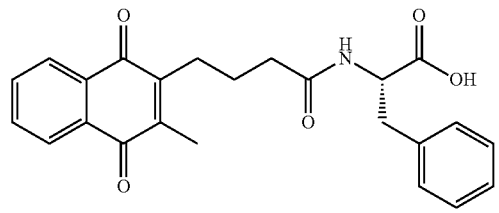 [SMILES: CC1=C(CCCC(=O)N[C@@H](Cc2ccccc2)C(=O)O)C(=O)c2ccccc2C1=O] |
| UTA #47 | 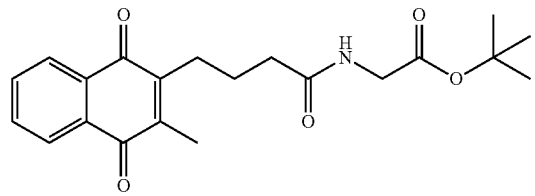 [SMILES: CC1=C(CCCC(=O)NCC(=O)OC(C)(C)C)C(=O)c2ccccc2C1=O] |
| UTA #54 | 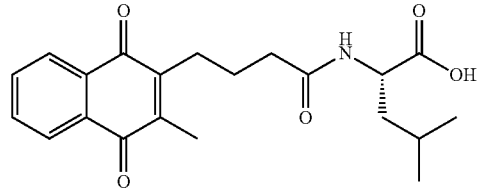 [SMILES: CC1=C(CCCC(=O)N[C@@H](CC(C)C)C(=O)O)C(=O)c2ccccc2C1=O] |

-continued
| Designated No. | Structure |
|---|---|
| UTA #55 | 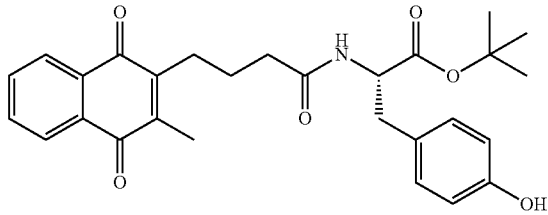 [SMILES: CC1=C(CCCC(=O)N[C@@H](Cc2ccc(O)cc2)C(=O)OC(C)(C)C)C(=O)c2ccccc2C1=O] |
| UTA #62 | 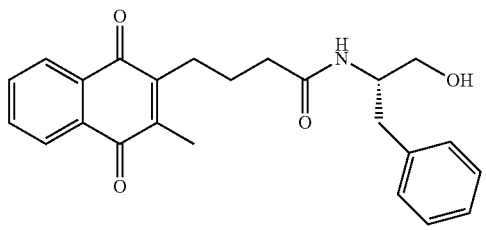 [SMILES: CC1=C(CCCC(=O)N[C@H](CO)Cc2ccccc2)C(=O)c2ccccc2C1=O] |
| UTA #65 | 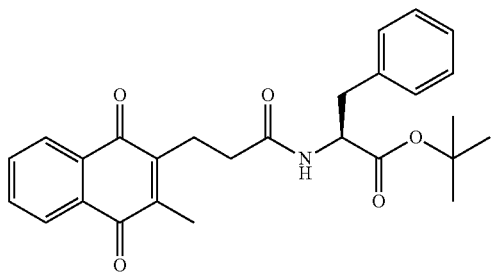 [SMILES: CC1=C(CCC(=O)N[C@@H](Cc2ccccc2)C(=O)OC(C)(C)C)C(=O)c2ccccc2C1=O] |
| UTA #66 | 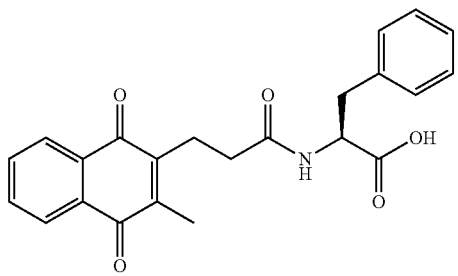 [SMILES: CC1=C(CCC(=O)N[C@@H](Cc2ccccc2)C(=O)O)C(=O)c2ccccc2C1=O] |
| UTA #72 | 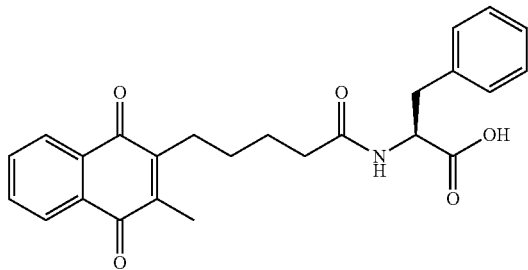 [SMILES: CC1=C(CCCCC(=O)N[C@@H](Cc2ccccc2)C(=O)O)C(=O)c2ccccc2C1=O] |
| UTA #73 | 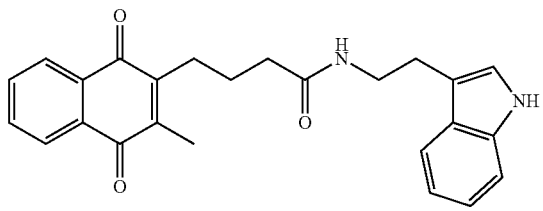 [SMILES: CC1=C(CCCC(=O)NCCc2c[nH]c3ccccc23)C(=O)c2ccccc2C1=O] |

| Designated No. | Structure |
|---|---|
| UTA #74 | 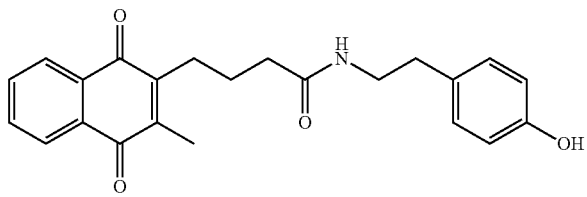 [SMILES: CC1=C(CCCC(=O)NCCc2ccc(O)cc2)C(=O)c2ccccc2C1=O] |
| UTA #75 | 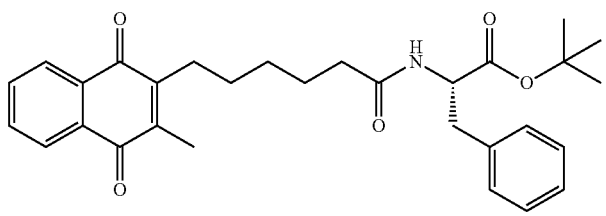 [SMILES: CC1=C(CCCCCC(=O)N[C@@H](Cc2ccccc2)C(=O)OC(C)(C)C)C(=O)c2ccccc2C1=O] |
| UTA #76 | 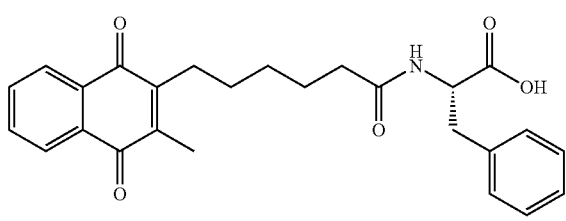 [SMILES: CC1=C(CCCCCC(=O)N[C@@H](Cc2ccccc2)C(=O)O)C(=O)c2ccccc2C1=O] |
| UTA #77 | 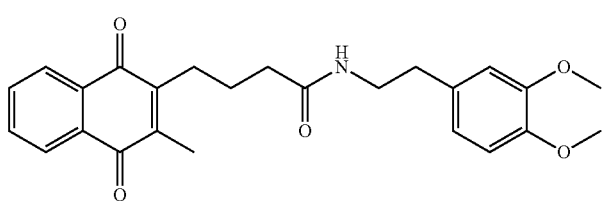 [SMILES: COc1ccc(CCNC(=O)CCCC2=C(C)C(=O)c3ccccc3C2=O)cc1OC] |
| UTA #78 | 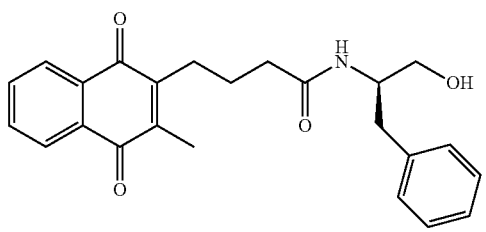 [SMILES: CC1=C(CCCC(=O)N[C@@H](CO)Cc2ccccc2)C(=O)c2ccccc2C1=O] |
| UTA #80 | 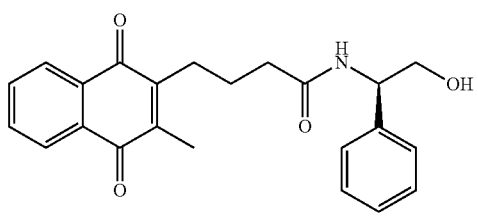 [SMILES: CC1=C(CCCC(=O)N[C@@H](CO)c2ccccc2)C(=O)c2ccccc2C1=O] |
| UTA #81 | 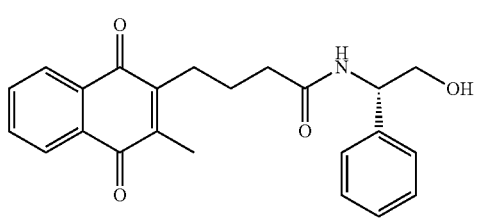 [SMILES: CC1=C(CCCC(=O)N[C@H](CO)c2ccccc2)C(=O)c2ccccc2C1=O] |

-continued
| Designated No. | Structure |
|---|---|
| UTA #84 | 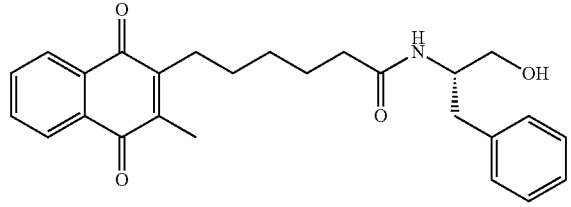 [SMILES: CC1=C(CCCCCC(=O)N[C@H](CO)Cc2ccccc2)C(=O)c2ccccc2C1=O] |
| UTA #88 | 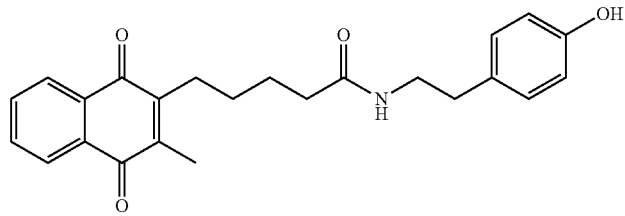 [SMILES: CC1=C(CCCCC(=O)NCCc2ccc(O)cc2)C(=O)c2ccccc2C1=O] |
| UTA #89 | 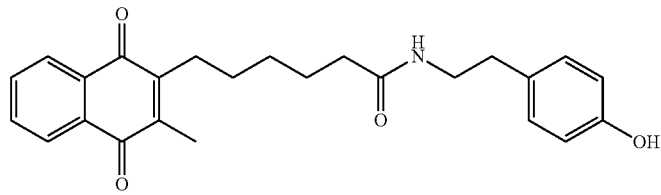 [SMILES: CC1=C(CCCCCC(=O)NCCc2ccc(O)cc2)C(=O)c2ccccc2C1=O] |
| UTA #91 | 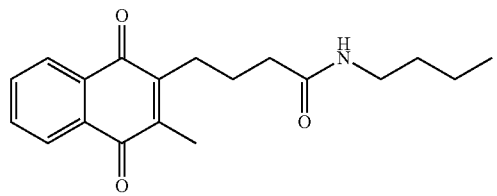 [SMILES: CCCCNC(=O)CCCC1=C(C)C(=O)c2ccccc2C1=O] |
| UTA #94 | 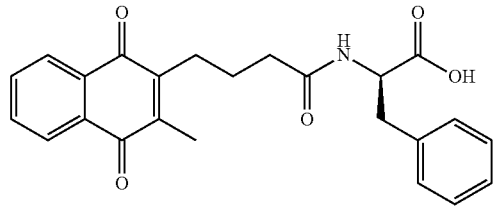 [SMILES: CC1=C(CCCC(=O)N[C@H](Cc2ccccc2)C(=O)O)C(=O)c2ccccc2C1=O] |
| UTA #95 | 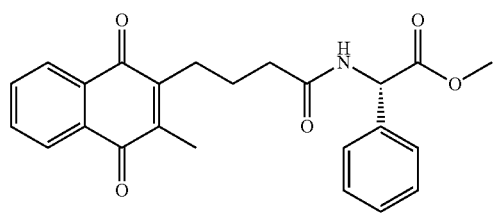 [SMILES: COC(=O)[C@@H](NC(=O)CCCC1=C(C)C(=O)c2ccccc2C1=O)c1ccccc1] |
| UTA #97 | 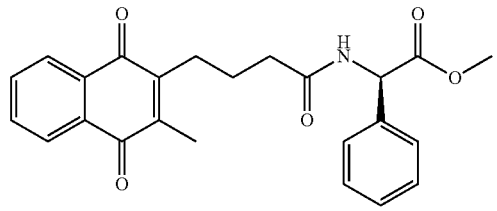 [SMILES: COC(=O)[C@H](NC(=O)CCCC1=C(C)C(=O)c2ccccc2C1=O)c1ccccc1] |

-continued

| Designated No. | Structure |
|---|---|
| UTA #113 | 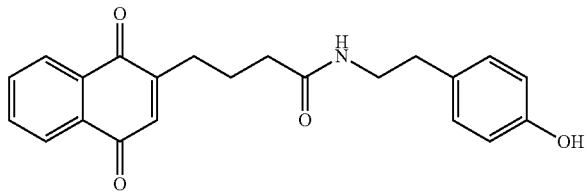 [SMILES: O=C(CCCC1=CC(=O)c2ccccc2C1=O)NCCc1ccc(O)cc1] |
| UTA #115 | 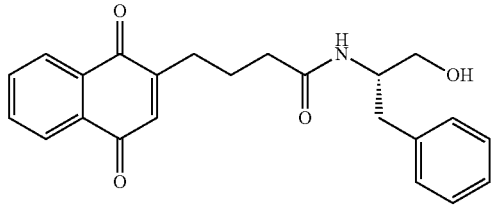 [SMILES: O=C(CCCC1=CC(=O)c2ccccc2C1=O)N[C@H](CO)Cc1ccccc1] |
| UTA #116 | 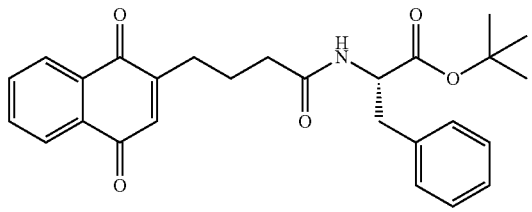 [SMILES: CC(C)(C)OC(=O)[C@H](Cc1ccccc1)NC(=O)CCCC1=CC(=O)c2ccccc2C1=O] |
| UTA #117 | 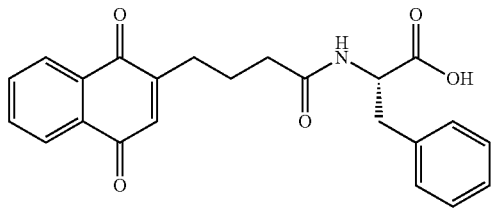 [SMILES: O=C(CCCC1=CC(=O)c2ccccc2C1=O)N[C@@H](Cc1ccccc1)C(=O)O] | or a pharmaceutically acceptable salt thereof.

7. A pharmaceutical composition comprising a compound according to any one of the preceding Claims.

8. A pharmaceutical composition according to claim 7 further comprising an additional active agent.

9. A pharmaceutical composition according to claim 8 wherein the additional active agent is an anti-diabetic agent.

10. A method of treating or preventing a disease or disorder associated with mitochondrial dysfunction, comprising administering to a person in need thereof, a therapeutically effective amount of a compound according to claim 1 or a pharmaceutical composition according to claim 7,
wherein the disease or disorder associated with mitochondrial dysfunction is selected from the group consisting of Leber's hereditary optic neuropathy (LHON), and ulcerative colitis (UC).

11. A method for the manufacture of a cosmetic product, the method comprising admixing a cosmetically effective amount of a compound according to claim 1, or a pharmaceutical composition according to claim 7, and an excipient.

* * * * *

UNITED STATES PATENT AND TRADEMARK OFFICE
CERTIFICATE OF CORRECTION

PATENT NO. : 10,934,253 B2
APPLICATION NO. : 16/606842
DATED : March 2, 2021
INVENTOR(S) : Nuri Guven et al.

Page 1 of 1

It is certified that error appears in the above-identified patent and that said Letters Patent is hereby corrected as shown below:

In the Claims

Claim 5, Column 74, Lines 44-45, "Leber's hereditary optic neuropathy (LHON), and ulcerative colitis (UC)." should read --Leber's hereditary optic neuropathy (LHON), diabetic retinopathy, and ulcerative colitis (UC).--.

Signed and Sealed this
Fifth Day of March, 2024

Katherine Kelly Vidal
*Director of the United States Patent and Trademark Office*